US011680103B2

(12) United States Patent
Orentas et al.

(10) Patent No.: US 11,680,103 B2
(45) Date of Patent: Jun. 20, 2023

(54) COMPOSITIONS AND METHODS FOR TREATING CANCER WITH ANTI-CD19/CD20 IMMUNOTHERAPY

(71) Applicant: Lentigen Technology, Inc., Gaithersburg, MD (US)

(72) Inventors: Rimas J. Orentas, Seattle, WA (US); Boro Dropulic, Ellicott City, MD (US); Dina Schneider, Potomac, MD (US)

(73) Assignee: LENTIGEN TECHNOLOGY, INC., Gaithersburg, MD (US)

( * ) Notice: Subject to any disclaimer, the term of this patent is extended or adjusted under 35 U.S.C. 154(b) by 780 days.

(21) Appl. No.: 16/599,473

(22) Filed: Oct. 11, 2019

(65) Prior Publication Data

US 2020/0109210 A1    Apr. 9, 2020

Related U.S. Application Data

(62) Division of application No. 16/050,754, filed on Jul. 31, 2018, now Pat. No. 10,442,867.

(60) Provisional application No. 62/539,483, filed on Jul. 31, 2017.

(51) Int. Cl.
| | | |
|---|---|---|
| *A61K 35/17* | (2015.01) | |
| *A61K 48/00* | (2006.01) | |
| *A61K 39/395* | (2006.01) | |
| *C07K 16/28* | (2006.01) | |
| *C07K 14/705* | (2006.01) | |
| *A61P 35/02* | (2006.01) | |
| *C07K 14/725* | (2006.01) | |

(52) U.S. Cl.
CPC ........ *C07K 16/2887* (2013.01); *A61K 35/17* (2013.01); *A61P 35/02* (2018.01); *C07K 14/705* (2013.01); *C07K 14/7051* (2013.01); *C07K 14/70517* (2013.01); *C07K 14/70521* (2013.01); *C07K 14/70578* (2013.01); *C07K 16/2803* (2013.01); *C07K 2317/31* (2013.01); *C07K 2317/56* (2013.01); *C07K 2317/622* (2013.01); *C07K 2317/73* (2013.01); *C07K 2319/02* (2013.01); *C07K 2319/03* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 6,410,319 B1 | 6/2002 | Raubitschek et al. | |
| 8,399,645 B2 | 3/2013 | Campana et al. | |
| 8,906,682 B2 | 12/2014 | June et al. | |
| 8,911,993 B2 | 12/2014 | June et al. | |
| 9,101,584 B2 | 8/2015 | June et al. | |
| 9,102,761 B2 | 8/2015 | June et al. | |
| 9,464,140 B2 | 10/2016 | June et al. | |
| 9,481,728 B2 | 11/2016 | June et al. | |
| 9,499,629 B2 | 11/2016 | June et al. | |
| 9,518,123 B2 | 12/2016 | June et al. | |
| 9,605,049 B2 | 3/2017 | Campana et al. | |
| 9,540,445 B2 | 6/2017 | June et al. | |
| 9,856,322 B2 | 6/2018 | Campana et al. | |
| 9,987,308 B2 | 6/2018 | Riddell et al. | |
| 2017/0107285 A1 | 4/2017 | Jensen | |
| 2017/0283775 A1 | 10/2017 | June et al. | |
| 2017/0368098 A1 | 12/2017 | Chen et al. | |
| 2018/0258391 A1 | 9/2018 | June et al. | |

FOREIGN PATENT DOCUMENTS

| | | |
|---|---|---|
| CN | 106535925 | 3/2017 |
| WO | WO 2005044996 | 5/2005 |
| WO | WO 2012079000 | 6/2012 |
| WO | WO 2013123061 | 8/2013 |
| WO | WO 2016100232 | 6/2016 |
| WO | WO 2017025038 | 2/2017 |
| WO | WO 2017222593 | 12/2017 |
| WO | WO 2018045325 | 3/2018 |

OTHER PUBLICATIONS

Brenner and Okur, "Overview of gene therapy clinical progress including cancer treatment with gene-modified T cells," Hematology Am. Soc. Hematol. Educ. Program, 2009, pp. 675-681.
Fumoto, et al., Targeted Gene Delivery: Importance of Administration Routes, Chapter 1, Intech, 2013, pp. 3-31.
Schneider, et al., "A tandem CD19/CD20 CAR lentiviral vector drives on-target and off-target antigen modulation in leukemia cell lines," Journal for Immunotherapy of Cancer, 2017, 5(1):1-17.
Schneider, et al., "Abstract 2297: Tandem anti-CD20 and -CD19 scFV-based chimeric antigen receptors (CARs) mitigate tumor escape in hematologic malignancies," Cancer Research, 2016, 76(14).
Schneider, et al., "Leukemia Cell Surface Antigen Modulation Induced by Dual CD19/CD20 Chimeric Antigen Receptor (CAR)-T Cells," Biology of Blood and Marrow Transplantation, 2017, 23(3):S250-S251.
Xiong, et al., "Mitigating tumor escape: Tandem Anti-CD20- and CD19 SCFV-Based Chimeric Antigen Receptors (CARs) in Leukemia/Lymphoma," Molecular Therapy, 2016, 24(S1).
Zah, et al., "T Cells Expressing CD19/CD20 Bispecific Chimeric Antigen Receptors Prevent Antigen Escape by Malignant B Cells," Cancer Immunol Res, 2016, 4:498-508.
Zhu, et al., "CAR-T Cell Production Using the Clinimacs Prodigy System," Blood, 2016, 128(22):5724.

(Continued)

*Primary Examiner* — Maria Marvich
(74) *Attorney, Agent, or Firm* — Serge Sira, Esq.; Gregory J. Hwa, Esq.; Fish & Richardson P.C.

(57) ABSTRACT

Chimeric antigen receptors containing CD19/CD20 or CD20/CD19 antigen binding domains are disclosed. Nucleic acids, recombinant expression vectors, host cells, antigen binding fragments, and pharmaceutical compositions, relating to the chimeric antigen receptors are also disclosed. Methods of treating or preventing cancer in a subject, and methods of making chimeric antigen receptor T cells are also disclosed.

6 Claims, 20 Drawing Sheets

Specification includes a Sequence Listing.

(56) References Cited

OTHER PUBLICATIONS

Zhu, et al., "Closed-system manufacturing of CD19 and dual-targeted CD20/19 chimeric antigen receptor T cells using the CliniMACS Prodigy device at an academic medical center," Cytotherapy, 2017, 20:394-406.

GenBank Accession No. HM852952.1, "Synthetic construct FMC63-28Z receptor protein gene, complete cds," dated Jun. 11, 2012, 2 pages.

GenBank Accession No. NP_001759.3, "T-cell surface glycoprotein CD8 alpha chain isoform 1 precursor [*Homo sapiens*]," dated Jun. 24, 2018, 3 pages.

GenBank No. NP_000725, "T-cell surface glycoprotein CD3 zeta chain isoform 2 precursor [*Homo sapiens*]," 4 pages.

UniProt No. Q07011.1, "Tumor necrosis factor receptor superfamily member 9," May 10, 2017, 5 pages.

Wu et al., "Multimerization of a chimeric anti-CD20 single-chain Fv-Fc fusion protein is mediated through variable domain exchange," Protein Engineering, Dec. 1, 2001, 14(12):1025-33.

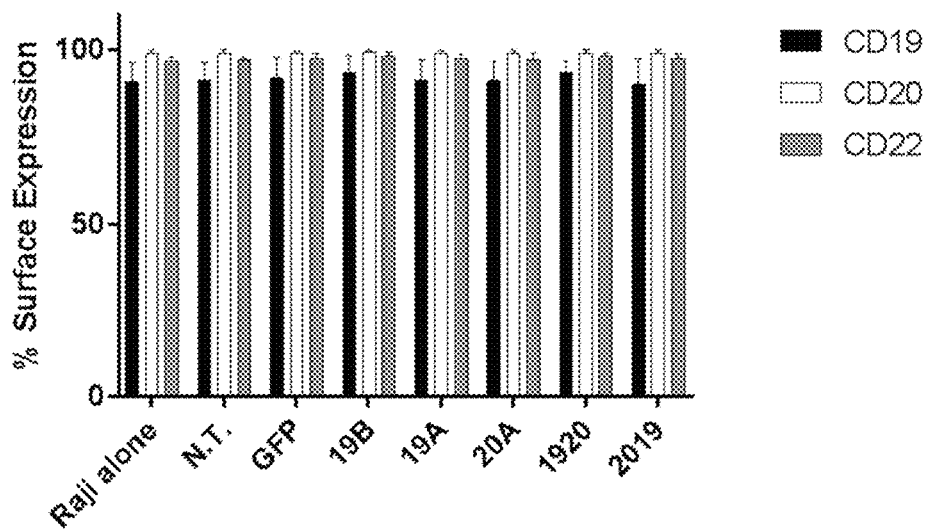
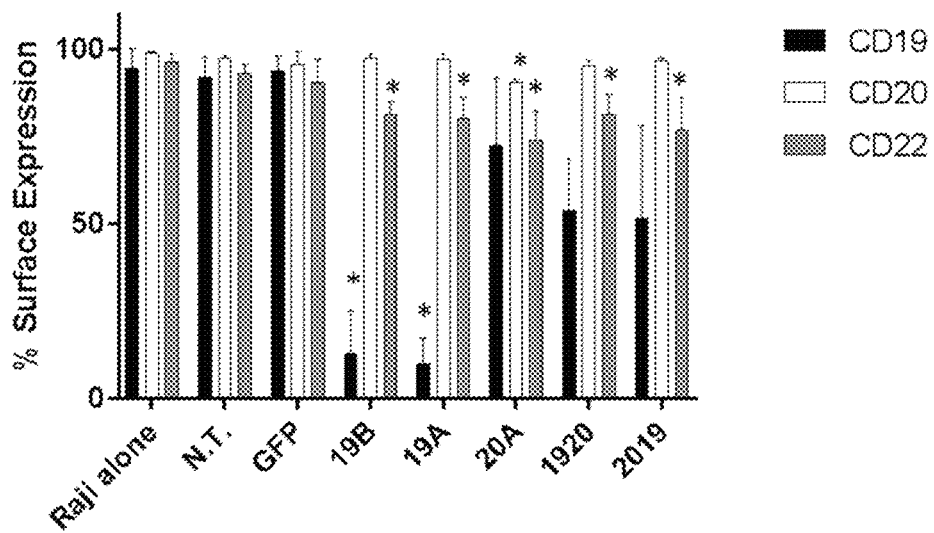
FIGURE 7

Leader-CD19 VL-Whitlow linker CD19 VH (GGGGS)-5 CD20 VH (GGGGS)-3 CD20 VL CD8 hinge+TM-4-1BB- CD3z (Construct 1920) nucleic acid sequence (SEQ ID NO: 1)

ATGCTCCTTCTCGTGACCTCCCTGCTTCTCTGCGAACTGCCCCATCCTGCCTTC
CTGCTG

ATTCCCGACATTCAGATGACTCAGACCACCTCCTCCCTGTCCGCCTCCCTGGG
CGACCGC

GTGACCATCTCATGCCGCGCCAGCCAGGACATCTCGAAGTACCTCAACTGGT
ACCAGCAG

AAGCCCGACGGAACCGTGAAGCTCCTGATCTACCACACCTCCCGGCTGCACA
GCGGAGTG

CCGTCTAGATTCTCGGGTTCGGGGTCGGGAACTGACTACTCCCTTACTATTTC
CAACCTG

GAGCAGGAGGATATTGCCACCTACTTCTGCCAACAAGGAAACACCCTGCCGT
ACACTTTT

GGCGGGGGAACCAAGCTGGAAATCACTGGCAGCACATCCGGTTCCGGGAAG
CCCGGCTCC

GGAGAGGGCAGCACCAAGGGGGAAGTCAAGCTGCAGGAATCAGGACCTGGC
CTGGTGGCC

CCGAGCCAGTCACTGTCCGTGACTTGTACTGTGTCCGGAGTGTCGCTCCCGGA
TTACGGA

GTGTCCTGGATCAGGCAGCCACCTCGGAAAGGATTGGAATGGCTCGGAGTCA
TCTGGGGT

TCCGAAACCACCTATTACAACTCGGCACTGAAATCCAGGCTCACCATTATCA
AGGATAAC

TCCAAGTCACAAGTGTTCCTGAAGATGAATAGCCTGCAGACTGACGACACGG
CGATCTAC

TATTGCGCCAAGCACTACTACTACGGCGGATCCTACGCTATGGACTACTGGG
GCCAGGGG

ACCAGCGTGACCGTGTCATCCGGAGGCGGCGGCAGCGGCGGGGGAGGGTCC
GGAGGGGGT

FIGURE 10A

GGTTCTGGTGGAGGAGGATCGGGAGGCGGTGGCAGCGAGGTGCAGTTGCAACAGTCAGGA

GCTGAACTGGTCAAGCCAGGAGCCAGCGTGAAGATGAGCTGCAAGGCCTCCGGTTACACC

TTCACCTCCTACAACATGCACTGGGTGAAACAGACCCCGGGACAAGGGCTCGAATGGATT

GGCGCCATCTACCCCGGGAATGGCGATACTTCGTACAACCAGAAGTTCAAGGGAAAGGCC

ACCCTGACCGCCGACAAGAGCTCCTCCACCGCGTATATGCAGTTGAGCTCCCTGACCTCC

GAGGACTCCGCCGACTACTACTGCGCACGGTCCAACTACTATGGAAGCTCGTACTGGTTC

TTCGATGTCTGGGGGGCCGGCACCACTGTGACCGTCAGCTCCGGGGGCGGAGGATCCGGT

GGAGGCGGAAGCGGGGGTGGAGGATCCGACATTGTGCTGACTCAGTCCCCGGCAATCCTG

TCGGCCTCACCGGGCGAAAAGGTCACGATGACTTGTAGAGCGTCGTCCAGCGTGAACTAC

ATGGATTGGTACCAAAAGAAGCCTGGATCGTCACCCAAGCCTTGGATCTACGCTACATCT

AACCTGGCCTCCGGCGTGCCAGCGCGGTTCAGCGGGTCCGGCTCGGGCACCTCATACTCG

CTGACCATCTCCCGCGTGGAGGCTGAGGACGCCGCGACCTACTACTGCCAGCAGTGGTCC

TTCAACCCGCCGACTTTTGGAGGCGGTACTAAGCTGGAGATCAAAGCGGCCGCAACTACC

ACCCCTGCCCCTCGGCCGCCGACTCCGGCCCCAACCATCGCAAGCCAACCCCTCTCCTTG

FIGURE 10A Contd.

CGCCCCGAAGCTTGCCGCCCGGCCGCGGGTGGAGCCGTGCATACCCGGGGGCTGGACTTT

GCCTGCGATATCTACATTTGGGCCCCGCTGGCCGGCACTTGCGGCGTGCTCCTGCTGTCG

CTGGTCATCACCCTTTACTGCAAGAGGGGCCGGAAGAAGCTGCTTTACATCTTCAAGCAG

CCGTTCATGCGGCCCGTGCAGACGACTCAGGAAGAGGACGGATGCTCGTGCAGATTCCCT

GAGGAGGAAGAGGGGGGATGCGAACTGCGCGTCAAGTTCTCACGGTCCGCCGACGCCCCC

GCATATCAACAGGGCCAGAATCAGCTCTACAACGAGCTGAACCTGGGAAGGAGAGAGGAG

TACGACGTGCTGGACAAGCGACGCGGACGCGACCCGGAGATGGGGGGGAAACCACGGCGG

AAAAACCCTCAGGAAGGACTGTACAACGAACTCCAGAAAGACAAGATGGCGGAAGCCTAC

TCAGAAATCGGGATGAAGGGAGAGCGGAGGAGGGGAAAGGGTCACGACGGGCTGTACCAG

GGACTGAGCACCGCCACTAAGGATACCTACGATGCCTTGCATATGCAAGCACTCCCACCC

CGG

FIGURE 10A Contd.

amino acid sequence of Leader-CD19 VL-Whitlow linker CD19 VH (GGGGS)-5 CD20 VH (GGGGS)-3 CD20 VL CD8 hinge+TM-4-1BB- CD3z (Construct CAR 1920) (SEQ ID NO: 2)

MLLLVTSLLLCELPHPAFLLIPDIQMTQTTSSLSASLGDRVTISCRASQDISKYLNWYQ
QKPDGTVKLLIYHTSRLHSGVPSRFSGSGSGTDYSLTISNLEQEDIATYFCQQGNTLPYTFGG
GTKLEITGSTSGSGKPGSGEGSTKGEVKLQESGPGLVAPSQSLSVTCTVSGVSLPDYGVSWIR
QPPRKGLEWLGVIWGSETTYYNSALKSRLTIIKDNSKSQVFLKMNSLQTDDTAIYYCAKHYY
YGGSYAMDYWGQGTSVTVSSGGGGSGGGGSGGGGSGGGGSGGGGSEVQLQQSGAELVKP
GASVKMSCKASGYTFTSYNMHWVKQTPGQGLEWIGAIYPGNGDTSYNQKFKGKATLTADK
SSSTAYMQLSSLTSEDSADYYCARSNYYGSSYWFFDVWGAGTTVTVSSGGGGSGGGGSGG
GGSDIVLTQSPAILSASPGEKVTMTCRASSSVNYMDWYQKKPGSSPKPWIYATSNLASGVPA
RFSGSGSGTSYSLTISRVEAEDAATYYCQQWSFNPPTFGGGTKLEIKAAATTTPAPRPPTPAPT
IASQPLSLRPEACRPAAGGAVHTRGLDFACDIYIWAPLAGTCGVLLLSLVITLYCKRGRKKLL
YIFKQPFMRPVQTTQEEDGCSCRFPEEEEGGCELRVKFSRSADAPAYQQGQNQLYNELNLGR
REEYDVLDKRRGRDPEMGGKPRRKNPQEGLYNELQKDKMAEAYSEIGMKGERRRGKGHD
GLYQGLSTATKDTYDALHMQALPPR

FIGURE 10A Contd.

Leader-CD20 VH (GGGGS)3 - CD20 VL -(GGGGS)5 -CD19 VL-Whitlow linker- CD19 VH CD8 hinge+TM-4-1BB- CD3z (Construct 2019) nucleic acid sequence (SEQ ID NO: 3)

ATGCTCCTTCTCGTGACCTCCCTGCTTCTCTGCGAACTGCCCCATCCTGCCTTC
CTGCTG

ATTCCCGAGGTGCAGTTGCAACAGTCAGGAGCTGAACTGGTCAAGCCAGGAG
CCAGCGTG

AAGATGAGCTGCAAGGCCTCCGGTTACACCTTCACCTCCTACAACATGCACT
GGGTGAAA

CAGACCCCGGGACAAGGGCTCGAATGGATTGGCGCCATCTACCCCGGGAATG
GCGATACT

TCGTACAACCAGAAGTTCAAGGGAAAGGCCACCCTGACCGCCGACAAGAGC
TCCTCCACC

GCGTATATGCAGTTGAGCTCCCTGACCTCCGAGGACTCCGCCGACTACTACTG
CGCACGG

TCCAACTACTATGGAAGCTCGTACTGGTTCTTCGATGTCTGGGGGGCCGGCAC
CACTGTG

ACCGTCAGCTCCGGGGGCGGAGGATCCGGTGGAGGCGGAAGCGGGGGTGGA
GGATCCGAC

ATTGTGCTGACTCAGTCCCCGGCAATCCTGTCGGCCTCACCGGGCGAAAAGG
TCACGATG

ACTTGTAGAGCGTCGTCCAGCGTGAACTACATGGATTGGTACCAAAAGAAGC
CTGGATCG

TCACCCAAGCCTTGGATCTACGCTACATCTAACCTGGCCTCCGGCGTGCCAGC
GCGGTTC

AGCGGGTCCGGCTCGGGCACCTCATACTCGCTGACCATCTCCCGCGTGGAGG
CTGAGGAC

GCCGCGACCTACTACTGCCAGCAGTGGTCCTTCAACCCGCCGACTTTTGGAG
GCGGTACT

FIGURE 10B

AAGCTGGAGATCAAAGGAGGCGGCGGCAGCGGCGGGGGAGGGTCCGGAGGGGGTGGTTCT

GGTGGAGGAGGATCGGGAGGCGGTGGCAGCGACATTCAGATGACTCAGACCACCTCCTCC

CTGTCCGCCTCCCTGGGCGACCGCGTGACCATCTCATGCCGCGCCAGCCAGGACATCTCG

AAGTACCTCAACTGGTACCAGCAGAAGCCCGACGGAACCGTGAAGCTCCTGATCTACCAC

ACCTCCCGGCTGCACAGCGGAGTGCCGTCTAGATTCTCGGGTTCGGGGTCGGGAACTGAC

TACTCCCTTACTATTTCCAACCTGGAGCAGGAGGATATTGCCACCTACTTCTGCCAACAA

GGAAACACCCTGCCGTACACTTTTGGCGGGGGAACCAAGCTGGAAATCACTGGCAGCACA

TCCGGTTCCGGGAAGCCCGGCTCCGGAGAGGGCAGCACCAAGGGGGAAGTCAAGCTGCAG

GAATCAGGACCTGGCCTGGTGGCCCCGAGCCAGTCACTGTCCGTGACTTGTACTGTGTCC

GGAGTGTCGCTCCCGGATTACGGAGTGTCCTGGATCAGGCAGCCACCTCGGAAGGATTG

GAATGGCTCGGAGTCATCTGGGGTTCCGAAACCACCTATTACAACTCGGCACTGAAATCC

AGGCTCACCATTATCAAGGATAACTCCAAGTCACAAGTGTTCCTGAAGATGAATAGCCTG

CAGACTGACGACACGGCGATCTACTATTGCGCCAAGCACTACTACTACGGCGGATCCTAC

GCTATGGACTACTGGGGCCAGGGGACCAGCGTGACCGTGTCATCCGCGGCCGCAACTACC

ACCCCTGCCCCTCGGCCGCCGACTCCGGCCCCAACCATCGCAAGCCAACCCCTCTCCTTG

FIGURE 10B Contd.

CGCCCCGAAGCTTGCCGCCCGGCCGCGGGTGGAGCCGTGCATACCCGGGGGCTGGACTTT

GCCTGCGATATCTACATTTGGGCCCCGCTGGCCGGCACTTGCGGCGTGCTCCTGCTGTCG

CTGGTCATCACCCTTTACTGCAAGAGGGGCCGGAAGAAGCTGCTTTACATCTTCAAGCAG

CCGTTCATGCGGCCCGTGCAGACGACTCAGGAAGAGGACGGATGCTCGTGCAGATTCCCT

GAGGAGGAAGAGGGGGGATGCGAACTGCGCGTCAAGTTCTCACGGTCCGCCGACGCCCCC

GCATATCAACAGGGCCAGAATCAGCTCTACAACGAGCTGAACCTGGGAAGGAGAGAGGAG

TACGACGTGCTGGACAAGCGACGCGGACGCGACCCGGAGATGGGGGGGAAACCACGGCGG

AAAAACCCTCAGGAAGGACTGTACAACGAACTCCAGAAAGACAAGATGGCGGAAGCCTAC

TCAGAAATCGGGATGAAGGGAGAGCGGAGGAGGGGAAAGGGTCACGACGGGCTGTACCAG

GGACTGAGCACCGCCACTAAGGATACCTACGATGCCTTGCATATGCAAGCACTCCCACCC

CGG

FIGURE 10B Contd.

Leader-CD20 VH (GGGGS)3 - CD20 VL -(GGGGS)5 -CD19 VL-Whitlow linker- CD19 VH CD8 hinge+TM-4-1BB- CD3z amino acid sequence (Construct CAR 2019) (SEQ ID NO: 4)

MLLLVTSLLLCELPHPAFLLIPEVQLQQSGAELVKPGASVKMSCKASGYTFTSYN
MHWVKQTPGQGLEWIGAIYPGNGDTSYNQKFKGKATLTADKSSSTAYMQLSSL
TSEDSADYYCARSNYYGSSYWFFDVWGAGTTVTVSSGGGGSGGGGSGGGGSDI
VLTQSPAILSASPGEKVTMTCRASSSVNYMDWYQKKPGSSPKPWIYATSNLASG
VPARFSGSGSGTSYSLTISRVEAEDAATYYCQQWSFNPPTFGGGTKLEIKGGGGS
GGGGSGGGGSGGGGSGGGGSDIQMTQTTSSLSASLGDRVTISCRASQDISKYLN
WYQQKPDGTVKLLIYHTSRLHSGVPSRFSGSGSGTDYSLTISNLEQEDIATYFCQ
QGNTLPYTFGGGTKLEITGSTSGSGKPGSGEGSTKGEVKLQESGPGLVAPSQSLS
VTCTVSGVSLPDYGVSWIRQPPRKGLEWLGVIWGSETTYYNSALKSRLTIIKDNS
KSQVFLKMNSLQTDDTAIYYCAKHYYYGGSYAMDYWGQGTSVTVSSAAATTT
PAPRPPTPAPTIASQPLSLRPEACRPAAGGAVHTRGLDFACDIYIWAPLAGTCGVL
LLSLVITLYCKRGRKKLLYIFKQPFMRPVQTTQEEDGCSCRFPEEEEGGCELRVKF
SRSADAPAYQQGQNQLYNELNLGRREEYDVLDKRRGRDPEMGGKPRRKNPQE
GLYNELQKDKMAEAYSEIGMKGERRRGKGHDGLYQGLSTATKDTYDALHMQA
LPPR

FIGURE 10B Contd.

COMPOSITIONS AND METHODS FOR TREATING CANCER WITH ANTI-CD19/CD20 IMMUNOTHERAPY

CROSS REFERENCE TO RELATED APPLICATIONS

This application is a divisional of U.S. application Ser. No. 16/050,754 filed Jul. 13, 2018 now U.S. Pat. No. 10,442,867 which claims the benefit of priority to U.S. Provisional Patent Application 62/539,483 filed Jul. 31, 2017, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Oct. 31, 2022, is named 42449-0015002_ST25.txt and is 61,206 bytes in size.

FIELD OF THE DISCLOSURE

This application relates to the field of cancer, particularly to CD19/CD20 antigen binding domains and chimeric antigen receptors (CARs) containing such CD19/CD20 antigen binding domains and methods of use thereof.

BACKGROUND

Cancer is one of the most deadly threats to human health. In the U.S. alone, cancer affects nearly 1.3 million new patients each year, and is the second leading cause of death after cardiovascular disease, accounting for approximately 1 in 4 deaths. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making treatment extremely difficult.

CD19 is a 85-95 kDa transmembrane cell surface glycoprotein receptor. CD19 is a member of immunoglobulin (Ig) superfamily of proteins, and contains two extracellular Ig-like domains, a transmembrane, and an intracellular signaling domain (Tedder T F, Isaacs, C M, 1989, J Immunol 143:712-171). CD19 modifies B cell receptor signaling, lowering the triggering threshold for the B cell receptor for antigen (Carter, R H, and Fearon, D T, 1992, Science, 256:105-107), and co-ordinates with CD81 and CD21 to regulate this essential B cell signaling complex (Bradbury, L E, Kansas G S, Levy S, Evans R L, Tedder T F, 1992, J Immunol, 149:2841-50). During B cell ontogeny CD19 is able to signal at the pro-B, pre-pre-B cell, pre-B, early B cell stages independent of antigen receptor, and is associated with Src family protein tyrosine kinases, is tyrosine phosphorylated, inducing both intracellular calcium mobilization and inositol phospholipid signaling (Uckun F M, Burkhardt A L, Jarvis L, Jun X, Stealy B, Dibirdik I, Myers D E, Tuel-Ahlgren L, Bolen J B, 1983, J Biol Chem 268:21172-84). The key point of relevance for treatment of B cell malignancies is that CD19 is expressed in a tightly regulated manner on normal B cells, being restricted to early B cell precursors at the stage of IgH gene rearrangement, mature B cells, but not expressed on hematopoietic stem cells, or mature plasma cells (Anderson, K C, Bates, M P, Slaughenhout B L, Pinkus G S, Schlossman S F, Nadler L M, 1984, Blood 63:1424-1433).

CD20 (also termed LEU-16, MS4A1) is a membrane-spanning 4A family protein that is expressed on the surface of B cells from pro-B phase to mature B cell phase, and plays a role in B cell development and differentiation. CD20 antigen is also expressed on a variety of hematological tumors, and a variety of monoclonal anti-CD20 antibodies have been applied over the years for the treatment of CD20-positive malignancies (Reviewed in Lim, Sean H. et al. "Anti-CD20 Monoclonal Antibodies: Historical and Future Perspectives." *Haematologica* 95.1 (2010): 135-143. PMC. Web. 31 Jul. 2017.) The anti CD20 monoclonal antibody Rituximab (Rituxan®) is widely used in treatment of B-cell lymphomas, such as follicular lymphoma (FL), and diffuse large B cell lymphoma (DLBCL), and chronic lymphocytic leukemia (CLL) (Rituxan prescribing information).

The traditional treatment approaches for B-lineage leukemias and lymphomas may involve chemotherapy, radiotherapy and stem cells transplant (see the world wide web at mayclinic.org). High toxicity associated with these treatments, as well as the risk of complications, such as relapse, secondary malignancy, or GVHD, motivate the search for better therapeutic alternatives. The expression of CD19 on both adult and pediatric (pre-B-ALL) B cell malignancies has led to exploiting this target for both antibody and chimeric antigen receptor (CAR)-T cell-based therapy (Kochenderfer J N, Wilson W H, Janik J E, Dudley M E, Stetler-Stevenson M, Feldman S A, Maric I, Raffeld M, Nathan D A, Lanier B J, Morgan R A, Rosenberg S A, 2010, Blood 116:4099-102; Lee D W, Kochenderfer J N, Stetler-Stevenson M, Cui Y K, Delbrook C, Feldman S A, Orentas R, Sabatino M, Shah N N, Steinberg S M, Stroncek D, Tschernia N, Yuan C, Zhang H, Zhang L, Rosenberg S A, Wayne A S, Mackall C L, 2015, Lancet 385:517-28). Moreover, the presence of CD20 antigen on lymphomas (DLBCL, FL), and leukemias (CLL) make it an attractive additional target for efficient tumor elimination and for the prevention of tumor antigen escape.

The present standard of care for B-lineage leukemias may consists of remission induction treatment by high dose of chemotherapy or radiation, followed by consolidation, and may feature stem cell transplantation and additional courses of chemotherapy as needed (see the world wide web at cancer.gov). High toxicity associated with these treatments, as well as the risk of complications, such as relapse, secondary malignancy, or GVHD, motivate the search for better therapeutic alternatives. The expression of CD19 on both adult and pediatric (pre-B-ALL) B cell malignancies has led to exploiting this target for both antibody and chimeric antigen receptor (CAR)-T cell-based therapy (Kochenderfer J N, Wilson W H, Janik J E, Dudley M E, Stetler-Stevenson M, Feldman S A, Maric I, Raffeld M, Nathan D A, Lanier B J, Morgan R A, Rosenberg S A, 2010, Blood 116:4099-102; Lee D W, Kochenderfer J N, Stetler-Stevenson M, Cui Y K, Delbrook C, Feldman S A, Orentas R, Sabatino M, Shah N N, Steinberg S M, Stroncek D, Tschernia N, Yuan C, Zhang H, Zhang L, Rosenberg S A, Wayne A S, Mackall C L, 2015, Lancet 385:517-28).

A number of novel approaches to treat B cell leukemia and lymphoma have been developed, including bi-specific antibodies that link an anti-CD19 or anti-CD20 binding motif to a T cell binding motif (i.e. Blinatumomab, Blincyto® indicated for the treatment of Philadelphia chromosome-negative relapsed or refractory B-cell precursor acute lymphoblastic leukemia (ALL). To date, many of the binding moieties for CD19 or CD20 employed in CAR constructs utilize a domain derived from murine antibodies. A number of these products are currently being considered for approval including those developed by Novartis and Kite Pharmaceuticals. In April of 2017 Novartis announced that CTL019 (tisagenlecleucel) received FDA breakthrough designation for treatment of adult patients with refractory or recurrent (r/r) DLBCL (diffuse large B cell lymphoma) who failed two or more prior therapies, adding this designation to that for r/r B-cell acute lymphoblastic leukemia (ALL). These indications were based on the Phase II JULIET study (NCT02445248) and the ELIANA study (NCT02435849), respectively. The JULIET trial showed and overall response rate (ORR) of 45%, with a 37% complete response (CR), and an 8% partial response (PR) at three months. In the ELIANA study, 82% of patients infused with the product achieved CR or CR with incomplete count recovery, and the relapse free survival rate at 6 months was 60%. The CAR-T product from Kite Pharmaceuticals (KTE-C19, axicabtagene ciloleucel) was granted breakthrough designation for diffuse large B-cell lymphoma (DLBLC), transformed follicular lymphoma (TFL), and primary mediastinal B-cell lymphoma (PMBCL). In the Kite ZUMA-3 phase II trial of KTE-C19 in r/r ALL, a 73% CR was reported (at 2 months or greater). Whether antibody of CAR-T therapies are utilized, there are still a significant number of patients who are not helped by these therapies, and there is considerable room for improved therapeutic approaches.

Chimeric Antigen Receptors (CARs) are hybrid molecules comprising three essential units: (1) an extracellular antigen-binding motif, (2) linking/transmembrane motifs, and (3) intracellular T-cell signaling motifs (Long A H, Haso W M, Orentas R J. Lessons learned from a highly-active CD22-specific chimeric antigen receptor. Oncoimmunology. 2013; 2 (4):e23621). The antigen-binding motif of a CAR is commonly fashioned after an single chain Fragment variable (ScFv), the minimal binding domain of an immunoglobulin (Ig) molecule. Alternate antigen-binding motifs, such as receptor ligands (i.e., IL-13 has been engineered to bind tumor expressed IL-13 receptor), intact immune receptors, library-derived peptides, and innate immune system effector molecules (such as NKG2D) also have been engineered. Alternate cell targets for CAR expression (such as NK or gamma-delta T cells) are also under development (Brown C E et al Clin Cancer Res. 2012; 18(8):2199-209; Lehner M et al. PLoS One. 2012; 7 (2):e31210). There remains significant work to be done with regard to defining the most active T-cell population to transduce with CAR vectors, determining the optimal culture and expansion techniques, and defining the molecular details of the CAR protein structure itself.

The linking motifs of a CAR can be a relatively stable structural domain, such as the constant domain of IgG, or designed to be an extended flexible linker. Structural motifs, such as those derived from IgG constant domains, can be used to extend the ScFv binding domain away from the T-cell plasma membrane surface. This may be important for some tumor targets where the binding domain is particularly close to the tumor cell surface membrane (such as for the disialoganglioside GD2; Orentas et al., unpublished observations). To date, the signaling motifs used in CARs always include the CD3-ζ chain because this core motif is the key signal for T cell activation. The first reported second-generation CARs featured CD28 signaling domains and the CD28 transmembrane sequence. This motif was used in third-generation CARs containing CD137 (4-1BB) signaling motifs as well (Zhao Y et al J Immunol. 2009; 183 (9): 5563-74). With the advent of new technology, the activation of T cells with beads linked to anti-CD3 and anti-CD28 antibody, and the presence of the canonical "signal 2" from CD28 was no longer required to be encoded by the CAR itself. Using bead activation, third-generation vectors were found to be not superior to second-generation vectors in in vitro assays, and they provided no clear benefit over second-generation vectors in mouse models of leukemia (Haso W, Lee D W, Shah N N, Stetler-Stevenson M, Yuan C M, Pastan I H, Dimitrov D S, Morgan R A, FitzGerald D J, Barrett D M, Wayne A S, Mackall C L, Orentas R J. Anti-CD22-chimeric antigen receptors targeting B cell precursor acute lymphoblastic leukemia, Blood. 2013; 121 (7):1165-74; Kochenderfer J N et al. Blood. 2012; 119 (12):2709-20). This is borne out by the clinical success of CD19-specific CARs that are in a second generation CD28/CD3- (Lee D W et al. American Society of Hematology Annual Meeting. New Orleans, La.; Dec. 7-10, 2013) and a CD137/CD3-ζ signaling format (Porter D L et al. N Engl J Med. 2011; 365 (8): 725-33). In addition to CD137, other tumor necrosis factor receptor superfamily members such as OX40 also are able to provide important persistence signals in CAR-transduced T cells (Yvon E et al. Clin Cancer Res. 2009; 15(18):5852-60). Equally important are the culture conditions under which the CAR T-cell populations were cultured, for example the inclusion of the cytokines IL-2, IL-7, and/or IL-15 (Kaiser A D et al. Cancer Gene Ther. 2015; 22(2):72-78).

Current challenges in the more widespread and effective adaptation of CAR therapy for cancer relate to a paucity of compelling targets. Creating binders to cell surface antigens is now readily achievable, but discovering a cell surface antigen that is specific for tumor while sparing normal tissues remains a formidable challenge. One potential way to imbue greater target cell specificity to CAR-expressing T cells is to use combinatorial CAR approaches. In one system, the CD3-ζ and CD28 signal units are split between two different CAR constructs expressed in the same cell; in another, two CARs are expressed in the same T cell, but one has a lower affinity and thus requires the alternate CAR to be engaged first for full activity of the second (Lanitis E et al. Cancer Immunol Res. 2013; 1(1):43-53; Kloss C C et al. Nat Biotechnol. 2013; 31(1):71-5). A second challenge for the generation of a single ScFv-based CAR as an immunotherapeutic agent is tumor cell heterogeneity. At least one group has developed a CAR strategy for glioblastoma whereby the effector cell population targets multiple antigens (HER2, IL-13Ra, EphA2) at the same time in the hope of avoiding the outgrowth of target antigen-negative populations. (Hegde M et al. Mol Ther. 2013; 21(11):2087-101).

T-cell-based immunotherapy has become a new frontier in synthetic biology; multiple promoters and gene products are envisioned to steer these highly potent cells to the tumor microenvironment, where T cells can both evade negative regulatory signals and mediate effective tumor killing. The elimination of unwanted T cells through the drug-induced dimerization of inducible caspase 9 constructs with chemical-based dimerizers, such as AP1903, demonstrates one way in which a powerful switch that can control T-cell populations can be initiated pharmacologically (Di Stasi A et al. N Engl J Med. 2011; 365(18):1673-83). The creation of effector T-cell populations that are immune to the negative regulatory effects of transforming growth factor-β by the expression of a decoy receptor further demonstrates the degree to which effector T cells can be engineered for optimal antitumor activity (Foster A E et al. J Immunother. 2008; 31(5):500-5). Thus, while it appears that CARs can trigger T-cell activation in a manner similar to an endogenous T-cell receptor, a major impediment to the clinical application of this technology to date has been limited in vivo expansion of CAR+ T cells, rapid disappearance of the cells after infusion, and disappointing clinical activity. This may be due in part to the murine origin of some of the CAR sequences employed.

The use of Blinotumomab (bi-specific anti-CD19 and anti-CD3 antibody) has shown impressive results for the gravely ill patients who have received this therapy. Nevertheless the durable remission rate is less than 40%, and at best only 50% of responders can be salvaged to hematopoietic stem cell transplant (HSCT) (see Gore et al., 2014, NCT01471782 and Von Stackelberg, et al., 2014, NCT01471782, summarized in: Benjamin, J E, Stein A S, 2016, Therapeutic Advances in Hematology 7:142-156). The requirement of patients who have received either bi-specific antibody or CAR-T therapy to subsequently undergo HSCT in order to maintain durable responses remains an area of active debate. Although high responses are reported for CD19 CAR-T trials, some even greater than 90%, if the trials are re-cast as "intent to treat" trials the number may be closer to 70% (Davis K L, Mackall C L, 2016, Blood Advances 1:265-268). The best results at 12 months post-CAR19 treatment reported show a RFS of 55% and OS of 79% in patients who were able to receive the T cell product at the University of Pennsylvania (Maude S L, Teachey D T, Rheingold S R, Shaw P A, Aplenc R, Barrett D M, Barker C S, Callahan C, Frey N V, Farzana N, Lacey S F, Zheng A, Levine B, Melenhorst J J, Motley L, Prter D L, June C H, Grupp S A, 2016, J Clin Oncol 34, no15 suppl (May 2016) 3011-3011).

Accordingly, there is an urgent and long felt need in the art for discovering novel compositions and methods for treatment of B-ALL and other CD19 and/or CD20-expressing B cell malignancies using an approach that can exhibit specific and efficacious anti-tumor effect without the aforementioned short comings.

The present invention addresses these needs by providing CAR compositions and therapeutic methods that can be used to treat cancers and other diseases and/or conditions. In particular, the present invention as disclosed and described herein provides CARs that may be used for the treatment of diseases, disorders or conditions associated with dysregulated expression of CD19 and/or CD20 and which CARs contain tandem CD19/CD20 antigen binding domains that exhibit a high surface expression on transduced T cells, exhibit a high degree of cytolysis of CD19-expressing cells, and in which the transduced T cells demonstrate in vivo expansion and persistence.

SUMMARY

Novel tandem CD19 and CD20-targeting antibodies or antigen binding domains thereof in which the CD19 targeting moiety is positioned either before or after the CD20 targeting moiety in the amino acid sequence (hereinafter termed "CD19/CD20"), and chimeric antigen receptors (tandem CARs) that contain such CD19 and/or CD20 antigen binding domains are provided herein, as well as host cells (e.g., T cells) expressing the receptors, and nucleic acid molecules encoding the receptors. The CARs exhibit a high surface expression on transduced T cells, with a high degree of cytolysis, and with transduced T cell expansion and persistence in vivo. Methods of using the disclosed CARs, host cells, and nucleic acid molecules are also provided, for example, to treat a cancer in a subject.

In one aspect, an isolated nucleic acid molecule encoding a tandem CD19/CD20 chimeric antigen receptor (CAR) is provided comprising, from N-terminus to C-terminus, at least one CD19/CD20 antigen binding domain, at least one transmembrane domain, and at least one intracellular signaling domain, wherein the tandem CD19/CD20 CAR comprises a nucleic acid sequence selected from the group consisting of SEQ ID NOs: 1 and 3.

In one aspect, an isolated nucleic acid molecule encoding a tandem CD19/CD20 chimeric antigen receptor (CAR) is provided comprising, from N-terminus to C-terminus, at least one CD19/CD20 antigen binding domain, at least one transmembrane domain, and at least one intracellular signaling domain, wherein the tandem CD19/CD20 CAR encoded by the nucleic acid sequence selected from the group consisting of SEQ ID NOs: 1 and 3 encodes a tandem CD19/CD20 CAR comprising the amino acid sequence selected from the group consisting of SEQ ID NO. 2 and 4.

In one embodiment, an isolated nucleic acid molecule encoding the CAR is provided wherein the encoded extracellular CD19/CD20 antigen binding domain comprises at least one single chain variable fragment of an antibody that binds to CD19/CD20.

In another embodiment, an isolated nucleic acid molecule encoding the CAR is provided wherein the encoded extracellular CD19/CD20 antigen binding domain comprises at least one heavy chain variable region of an antibody that binds to CD19/CD20.

In yet another embodiment, an isolated nucleic acid molecule encoding the CAR is provided wherein the encoded CAR extracellular CD19/CD20 antigen binding domain further comprises at least one lipocalin-based antigen binding antigen (anticalins) that binds to CD19/CD20.

In one embodiment, an isolated nucleic acid molecule is provided wherein the encoded extracellular CD19/CD20 antigen binding domain is connected to the transmembrane domain by a linker domain.

In another embodiment, an isolated nucleic acid molecule encoding the CAR is provided wherein the encoded CD19/CD20 extracellular antigen binding domain is preceded by a sequence encoding a leader or signal peptide.

In yet another embodiment, an isolated nucleic acid molecule encoding the CAR is provided comprising at least one CD19/CD20 antigen binding domain encoded by a nucleotide sequence comprising a CD19/CD20 nucleotide sequence contained within SEQ ID Nos: 1 and 3, respectively, and wherein the CAR additionally encodes an extracellular antigen binding domain targets an antigen that includes, but is not limited to, CD22, ROR1, mesothelin, CD33, CD38, CD123 (IL3RA), CD138, BCMA (CD269), GPC2, GPC3, FGFR4, c-Met, PSMA, Glycolipid F77, EGFRvIII, GD-2, TSLPR, NY-ESO-1 TCR, MAGE A3 TCR, or any combination thereof.

In certain embodiments, an isolated nucleic acid molecule encoding the CAR is provided wherein the additionally encoded extracellular antigen binding domain comprises an anti-CD22 ScFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-BCMA (CD269) ScFv antigen binding domain, an anti-GPC2 ScFv antigen binding domain, an anti-GPC3 ScFv antigen binding domain, an anti-FGFR4 ScFv antigen binding domain, an anti-TSLPR ScFv antigen binding domain an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESO-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In one aspect, the CARs provided herein further comprise a linker or spacer domain.

In one embodiment, an isolated nucleic acid molecule encoding the CAR is provided wherein the extracellular CD19/CD20 antigen binding domain, the intracellular signaling domain, or both are connected to the transmembrane domain by a linker or spacer domain.

In one embodiment, an isolated nucleic acid molecule encoding the CAR is provided wherein the encoded linker domain is derived from the extracellular domain of CD8 or CD28, and is linked to a transmembrane domain.

In another embodiment, an isolated nucleic acid molecule encoding the CAR is provided wherein the encoded CAR further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD83, CD86, CD134, CD137 and CD154, or a combination thereof.

In yet another embodiment, an isolated nucleic acid molecule encoding the CAR is provided wherein the encoded intracellular signaling domain further comprises a CD3 zeta intracellular domain.

In one embodiment, an isolated nucleic acid molecule encoding the CAR is provided wherein the encoded intracellular signaling domain is arranged on a C-terminal side relative to the CD3 zeta intracellular domain.

In another embodiment, an isolated nucleic acid molecule encoding the CAR is provided wherein the encoded at least one intracellular signaling domain comprises a costimulatory domain, a primary signaling domain, or a combination thereof.

In further embodiments, an isolated nucleic acid molecule encoding the CAR is provided wherein the encoded at least one costimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, an isolated nucleic acid molecule encoding the CAR is provided that further contains a leader sequence or signal peptide wherein the leader or signal peptide nucleotide sequence comprises the nucleotide sequence of SEQ ID NO: 11.

In yet another embodiment, an isolated nucleic acid molecule encoding the CAR is provided wherein the encoded leader sequence comprises the amino acid sequence of SEQ ID NO: 12.

In one aspect, a chimeric antigen receptor (CAR) is provided herein comprising, from N-terminus to C-terminus, at least one CD19/CD20 antigen binding domain, at least one transmembrane domain, and at least one intracellular signaling domain.

In one embodiment, a CAR is provided wherein the extracellular CD19/CD20 antigen binding domain comprises at least one single chain variable fragment of an antibody that binds to the antigen, or at least one heavy chain variable region of an antibody that binds to the antigen, or a combination thereof.

In another embodiment, a CAR is provided wherein the at least one transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, TNFRSF19, or a combination thereof.

In some embodiments, the CAR is provided wherein CAR additionally encodes an extracellular antigen binding domain comprising CD22, ROR1, mesothelin, CD33, CD38, CD123 (IL3RA), CD138, BCMA (CD269), GPC2, GPC3, FGFR4, TSLPR, c-Met, PSMA, Glycolipid F77, EGFRvIII, GD-2, TSLPR, NY-ESO-1 TCR, MAGE A3 TCR, or an amino acid sequence with 85%, 90%, 95%, 96%, 97%, 98% or 99% identity thereof, or any combination thereof.

In one embodiment, the CAR is provided wherein the extracellular antigen binding domain comprises an anti-CD22 ScFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-BCMA (CD269) ScFv antigen binding domain, an anti-GPC2 ScFv antigen binding domain, an anti-GPC3 ScFv antigen binding domain, an anti-FGFR4 ScFv antigen binding domain, anti-TSLPR ScFv antigen binding domain, an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESO-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In another embodiment, a CAR is provided wherein the at least one intracellular signaling domain comprises a costimulatory domain and a primary signaling domain.

In yet another embodiment, a CAR is provided wherein the at least one intracellular signaling domain comprises a costimulatory domain comprising a functional signaling domain of a protein selected from the group consisting of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, the nucleic acid sequence encoding a CAR comprises the nucleic acid sequence of SEQ ID NO: 1 (nucleotide sequence of Leader-CD19 VL-Whitlow linker CD19 VH (GGGGS)-5 CD20 VH (GGGGS)-3 CD20 VL CD8 hinge+TM-4-1BB-CD3z (Construct 1920) (FIG. 10A)). In one embodiment, the nucleic acid sequence encodes a CAR comprising the amino acid sequence of SEQ ID NO: 2 Leader-CD19 VL-Whitlow linker CD19 VH (GGGGS)-5 CD20 VH (GGGGS)-3 CD20 VL CD8 hinge+TM-4-1BB-CD3z (Construct 1920) ((FIG. 10A)).

In another embodiment, the nucleic acid sequence encoding a CAR comprises the nucleic acid sequence of SEQ ID NO: 3 (nucleotide sequence of Leader-CD20 VH (GGGGS) 3-CD20 VL-(GGGGS)5-CD19 VL-Whitlow linker-CD19 VH CD8 hinge+TM-4-1BB-CD3z (Construct 2019) (FIG. 10B)). In one embodiment, the nucleic acid sequence encodes a CAR comprising the amino acid sequence of SEQ ID NO: 4 (Leader-CD20 VH (GGGGS)$_3$-CD20 VL-(GGGGS)$_5$—CD19 VL-Whitlow linker-CD19 VH CD8 hinge+TM-4-1BB-CD3z CAR amino acid sequence (FIG. 10B)).

In one aspect, the CARs disclosed herein are modified to express or contain a detectable marker for use in diagnosis, monitoring, and/or predicting the treatment outcome such as progression free survival of cancer patients or for monitoring the progress of such treatment.

In one embodiment, the nucleic acid molecule encoding the disclosed CARs can be contained in a vector, such as a viral vector. The vector is a DNA vector, an RNA vector, a plasmid vector, a cosmid vector, a herpes virus vector, a measles virus vector, a lentivirus vector, adenoviral vector, or a retrovirus vector, or a combination thereof.

In certain embodiments, the vector further comprises a promoter wherein the promoter is an inducible promoter, a tissue specific promoter, a constitutive promoter, a suicide promoter or any combination thereof.

In yet another embodiment, the vector expressing the CAR can be further modified to include one or more operative elements to control the expression of CAR T cells, or to eliminate CAR-T cells by virtue of a suicide switch. The suicide switch can include, for example, an apoptosis inducing signaling cascade or a drug that induces cell death. In a preferred embodiment, the vector expressing the CAR can be further modified to express an enzyme such thymidine kinase (TK) or cytosine deaminase (CD).

In another aspect, host cells including the nucleic acid molecule encoding the CAR are also provided. In some embodiments, the host cell is a T cell, such as a primary T cell obtained from a subject. In one embodiment, the host cell is a CD8$^+$ T cell.

In yet another aspect, a pharmaceutical composition is provided comprising an anti-tumor effective amount of a population of human T cells, wherein the T cells comprise a nucleic acid sequence that encodes a chimeric antigen receptor (CAR) comprising the amino acid sequence of SEQ ID NO. 2 and 4, wherein the CAR comprises at least one extracellular antigen binding domain comprising a CD19/CD20 antigen binding domain, at least one linker domain, at least one transmembrane domain, and at least one intracellular signaling domain, wherein the T cells are T cells of a human having a cancer. The cancer includes, inter alia, a hematological cancer such as leukemia (e.g., chronic lymphocytic leukemia (CLL), acute lymphocytic leukemia (ALL), or chronic myelogenous leukemia (CML), lymphoma (e.g., mantle cell lymphoma, non-Hodgkin's lymphoma or Hodgkin's lymphoma) or multiple myeloma, or a combination thereof.

In one embodiment, a pharmaceutical composition is provided wherein the at least one transmembrane domain of the CAR contains a transmembrane domain of a protein selected from the group consisting of the alpha, beta or zeta chain of the T-cell receptor, CD28, CD3 epsilon, CD45, CD4, CD5, CD8, CD9, CD16, CD22, Mesothelin, CD33, CD37, CD64, CD80, CD83, CD86, CD134, CD137, CD154, TNFRSF19, or a combination thereof.

In another embodiment, a pharmaceutical composition is provided wherein the human cancer includes an adult carcinoma comprising oral and pharynx cancer (tongue, mouth, pharynx, head and neck), digestive system cancers (esophagus, stomach, small intestine, colon, rectum, anus, liver, interhepatic bile duct, gallbladder, pancreas), respiratory system cancers (larynx, lung and bronchus), bones and joint cancers, soft tissue cancers, skin cancers (melanoma, basal and squamous cell carcinoma), pediatric tumors (neuroblastoma, rhabdomyosarcoma, osteosarcoma, Ewing's sarcoma), tumors of the central nervous system (brain, astrocytoma, glioblastoma, glioma), and cancers of the breast, genital system (uterine cervix, uterine corpus, ovary, vulva, vagina, prostate, testis, penis, endometrium), the urinary system (urinary bladder, kidney and renal pelvis, ureter), the eye and orbit, the endocrine system (thyroid), and the brain and other nervous system, or any combination thereof.

In yet another embodiment, a pharmaceutical composition is provided comprising an anti-tumor effective amount of a population of human T cells of a human having a cancer wherein the cancer is a refractory cancer non-responsive to one or more chemotherapeutic agents. The cancer includes hematopoietic cancer, myelodysplastic syndrome pancreatic cancer, head and neck cancer, cutaneous tumors, minimal residual disease (MRD) in acute lymphoblastic leukemia (ALL), acute myeloid leukemia (AML), adult B cell malignancies including, CLL (Chronic lymphocytic leukemia), CML (chronic myelogenous leukemia), non-Hodgkin's lymphoma (NHL), pediatric B cell malignancies (including B lineage ALL (acute lymphocytic leukemia)), multiple myeloma lung cancer, breast cancer, ovarian cancer, prostate cancer, colon cancer, melanoma or other hematological cancer and solid tumors, or any combination thereof.

In another aspect, methods of making CAR-containing T cells (hereinafter "CAR-T cells") are provided. The methods include transducing a T cell with a vector or nucleic acid molecule encoding a disclosed CAR that specifically binds CD19 and/or CD20, thereby making the CAR-T cell.

In yet another aspect, a method of generating a population of RNA-engineered cells is provided that comprises introducing an in vitro transcribed RNA or synthetic RNA of a nucleic acid molecule encoding a disclosed CAR into a cell of a subject, thereby generating a CAR cell.

In one embodiment, the disease, disorder or condition associated with the expression of CD19 is cancer including hematopoietic cancer, myelodysplastic syndrome pancreatic cancer, head and neck cancer, cutaneous tumors, minimal residual disease (MRD) in acute lymphoblastic leukemia (ALL), acute myeloid leukemia (AML), adult B cell malignancies including, CLL (Chronic lymphocytic leukemia), CML (chronic myelogenous leukemia), non-Hodgkin's lymphoma (NHL), pediatric B cell malignancies (including B lineage ALL (acute lymphocytic leukemia)), multiple myeloma lung cancer, breast cancer, ovarian cancer, prostate cancer, colon cancer, melanoma or other hematological cancer and solid tumors, or any combination thereof.

In another embodiment, a method of blocking T-cell inhibition mediated by a CD19- and/or CD20 expressing cell and altering the tumor microenvironment to inhibit tumor growth in a mammal, is provided comprising administering to the mammal an effective amount of a composition comprising a CAR comprising the amino acid sequence selected from the group consisting of SEQ ID NOs: 2 and 4. In one embodiment, the cell is selected from the group consisting of a CD19 and/or CD20-expressing tumor cell, a tumor-associated macrophage, and any combination thereof.

In another embodiment, a method of inhibiting, suppressing or preventing immunosuppression of an anti-tumor or anti-cancer immune response in a mammal, is provided comprising administering to the mammal an effective amount of a composition comprising a CAR selected from the group consisting of SEQ ID NOs: 2 and 4. In one embodiment, the CAR inhibits the interaction between a first cell with a T cell, wherein the first cell is selected from the group consisting of a CD19 and/or CD20-expressing tumor cell, a tumor-associated macrophage, and any combination thereof.

In another aspect, a method is provided for inducing an anti-tumor immunity in a mammal comprising administering to the mammal a therapeutically effective amount of a T cell transduced with vector or nucleic acid molecule encoding a disclosed CAR.

In another embodiment, a method of treating or preventing cancer in a mammal is provided comprising administering to the mammal one or more of the disclosed CARs, in an amount effective to treat or prevent cancer in the mammal. The method includes administering to the subject a therapeutically effective amount of host cells expressing a disclosed CAR that specifically binds CD19 and/or CD20 and/or one or more of the aforementioned antigens, under conditions sufficient to form an immune complex of the antigen binding domain on the CAR and the extracellular domain of CD19 and/or CD20 and/or one or more of the aforementioned antigens in the subject.

In yet another embodiment, a method is provided for treating a mammal having a disease, disorder or condition associated with an elevated expression of a tumor antigen, the method comprising administering to the subject a pharmaceutical composition comprising an anti-tumor effective amount of a population of T cells, wherein the T cells comprise a nucleic acid sequence that encodes a chimeric antigen receptor (CAR), wherein the CAR includes at least one extracellular CD19 and/or CD20 antigen binding domain, or any combination thereof, at least one linker or spacer domain, at least one transmembrane domain, at least one intracellular signaling domain, and wherein the T cells are T cells of the subject having cancer.

In yet another embodiment, a method is provided for treating cancer in a subject in need thereof comprising administering to the subject a pharmaceutical composition comprising an anti-tumor effective amount of a population of T cells, wherein the T cells comprise a nucleic acid sequence that encodes a chimeric antigen receptor (CAR), wherein the CAR comprises the amino acid sequence of SEQ ID NOs. 2 and 4, or any combination thereof, at least one linker or spacer domain, at least one transmembrane domain, at least one intracellular signaling domain, wherein the T cells are T cells of the subject having cancer. In some embodiments of the aforementioned methods, the at least one transmembrane domain comprises a transmembrane the alpha, beta or zeta chain of the T-cell receptor, CD28, CD3 epsilon, CD45, CD4, CD5, CD8, CD9, CD16, CD19, CD22, Mesothelin, CD33, CD37, CD64, CD80, CD83, CD86, CD134, CD137, CD154, TNFRSF16, TNFRSF19, or a combination thereof.

In yet another embodiment, a method is provided for generating a persisting population of genetically engineered T cells in a human diagnosed with cancer. In one embodiment, the method comprises administering to a human a T cell genetically engineered to express a CAR wherein the CAR comprises the amino acid sequence of SEQ ID NOs. 2 and 4, or any combination thereof, at least one transmembrane domain, and at least one intracellular signaling domain wherein the persisting population of genetically engineered T cells, or the population of progeny of the T cells, persists in the human for at least one month, two months, three months, four months, five months, six months, seven months, eight months, nine months, ten months, eleven months, twelve months, two years, or three years after administration.

In one embodiment, the progeny T cells in the human comprise a memory T cell. In another embodiment, the T cell is an autologous T cell.

In all of the aspects and embodiments of methods described herein, any of the aforementioned cancers, diseases, disorders or conditions associated with an elevated expression of a tumor antigen that may be treated or prevented or ameliorated using one or more of the CARs disclosed herein.

In yet another aspect, a kit is provided for making a chimeric antigen receptor T-cell as described supra or for preventing, treating, or ameliorating any of the cancers, diseases, disorders or conditions associated with an elevated expression of a tumor antigen in a subject as described supra, comprising a container comprising any one of the nucleic acid molecules, vectors, host cells, or compositions disclosed supra or any combination thereof, and instructions for using the kit.

It will be understood that the CARs, host cells, nucleic acids, and methods are useful beyond the specific aspects and embodiments that are described in detail herein. The foregoing features and advantages of the disclosure will become more apparent from the following detailed description, which proceeds with reference to the accompanying figures.

BRIEF DESCRIPTION OF THE FIGURES

FIG. 1A: Anti-CD19 and anti-CD20 single targeting CAR constructs were generated by linking single chain fragment variable region of monoclonal antibody FMC-63 (CD19) of Leu-16 (CD20) in frame to CD8 hinge and transmembrane domain, the 4-1BB (CD137) signaling domain and the CD3 zeta signaling domain. Constructs 19A and 19B differ only in the linker sequence connecting the heavy and the light chains of FMC63. Tandem targeting constructs 2019 and 1920 were generated in a similar manner to single targeting constructs, except that the single chain fragment variable regions of CD20 and CD19 were linked to each other sequentially by a flexible linker, followed by CD8, 4-1BB and CD3 zeta domains. FIG. 1B: Schematic representation of Tandem-CAR T cells targeting CD19 and CD20 tumor antigens. The tandem-CAR 1920 (left) and 2019 (right) are comprised of tandem extracellular targeting domains linked in frame to CD8-derived hinge and transmembrane domains, followed by the 4-1BB costimulatory domain, and the CD3 zeta activation domain. Each CAR T construct is capable of activation via binding to either CD19 or CD20 tumor antigens, or both.

FIG. 3B), stably transduced with luciferase. CAR T cells and target tumor cells were co-incubated overnight at the listed effector to target (E:T) ratios, x-axis. Differences between groups were determined using 1-way ANOVA followed by Dunnett's post-hoc test. Mean+SD, **p<0.0001, p<0.01 vs non-transduced control from the same donor (N.T.).

FIG. 5A depicts a time course of tumor growth based on mouse whole body bioluminescence. 10 mice per CAR T treatment group, and 5 mice per control group were studied. FIG. 5B is a plot depicting the mean signal per mouse ±SD. Statistical analysis for Day 25 (the last time point when subjects in the no treatment control group remained alive) is shown, using two-way ANOVA followed by Dunnett's multiple comparisons test vs no treatment group. Mean +SD, ***P<0.001

FIG. 6A: Diagram of the experimental design for tumor escape experiments. Raji and CAR T cells were co-cultured at E:T ratio of 1:1 either overnight or for 4 days. After overnight incubation and on day 4, cultures were harvested and viable Raji cells examined for CD19, CD20, and CD22 surface expression by flow cytometry. FIG. 6B: Gating strategy for flow cytometric analysis used to analyze viable Raji cells (7AAD− and CD3−) from co-cultures is shown for representative treatment groups is shown in column 1. Columns 2, 3, and 4 show CD19, CD20, and CD22 expression levels, respectively, when Raji cells were co-cultured with no T cells (row 1), 19A CAR (row 2), or 2019 CAR (row 3). FIG. 6C: Graphs of CD19, CD20 and CD22 surface expression (solid, open, gray, respectively) in surviving Raji and NALM-6 cells after overnight or four days of co-culture with CAR T cells, as listed on x-axis, as determined by flow cytometry. Bars represent group means +SD. Statistical analysis was performed by one-way ANOVA followed by Dunnett's multiple comparisons test vs N.T. (non-transduced T cells) control from the same donor, *p<0.05. T.A.—tumor alone control group.

FIG. 7. The down-modulation of CD19, CD20 and CD22 on Raji surface requires direct contact with CART cells. Multi-well plates with transwell inserts were used in this experiment. At the bottom of each well, $5 \times 10^5$ each of Raji and CART cells were combined, and in the transwell upper portion $2.5 \times 10^5$ Raji cells were cultured in the absence of T cells. After overnight incubation, cells from the upper transwell compartment and from the bottom compartment were harvested, and viable Raji cells were examined for CD19, CD20, and CD22 surface expression by flow cytometry (black, light grey, and dark grey bars, respectively. Surface expression for each marker with reference to the specific CAR T included in the lower compartment (x-axis) is shown. Bars depict mean +SD of three independent experiments performed using CAR T cells originating from three different donors. One way ANOVA, Dunnett's multiple comparisons test *p<0.05.

FIG. 8A: Raji cell samples were stained with anti-CD19 antibody and acquired by flow cytometry. Median fluorescence intensity for Raji cells representing each treatment group is shown. Bars depict mean +SD of three independent experiments performed using CAR T cells originating from three different donors. One way ANOVA, Dunnett's multiple comparisons test *p<0.05. FIG. 8B: Lysates of purified Raji cells from each of the co-incubated groups (CAR-T identity is listed above each line) were resolved on a 4%-12% SDS polyacrylamide gel as described in the Materials and Methods, and probed with antibodies targeting the C-terminus of CD19 molecule, or β-actin (loading control). FIG. 8C: The intensity of specific immunoreactive bands representing full-length CD19 protein (FL CD19), and the exon 2 spliced CD19 variant (Δ2CD19) was quantified using Image Studio software (LI-COR Biosciences). Relative band intensity of CD19 bands was calculated as signal CD19/signal β actin.

FIG. 9A: Disease burden is plotted as the average bioluminescent signal (mean radiance [p/s/cm2/sr])±SEM. Groups with less than half of the mice surviving to day 25 are plotted as dotted lines. Groups where more than half survived are plotted as solid lines. FIG. 9B: Bioluminescent images of the tumor burden in mice treated with singe and tandem-CAR T constructs as indicated in the plot above on day 25 post tumor engraftment are shown. Red X indicates mice that did not survive to study day 25.

FIGS. 10A and 10B depict the nucleic acid sequence and the encoded amino acid sequence of CAR T constructs. FIG. 10A depicts a lentiviral vector expressing the CAR Leader-CD19 VL-Whitlow linker CD19 VH (GGGGS)-5 CD20 VH (GGGGS)-3 CD20 VL CD8 hinge+TM-4-1BB-CD3z (CD1920 CAR Construct) nucleic acid sequence and the encoded amino acid sequence.

FIG. 10B depicts a lentiviral vector expressing the CAR containing the Leader-CD20 VH (GGGGS)3-CD20 VL-(GGGGS)5-CD19 VL-Whitlow linker-CD19 VH CD8 hinge+TM-4-1BB-CD3z (CD2019 CAR Construct) nucleic acid sequence and the encoded amino acid sequence.

DETAILED DESCRIPTION

Definitions

Figure 1A:
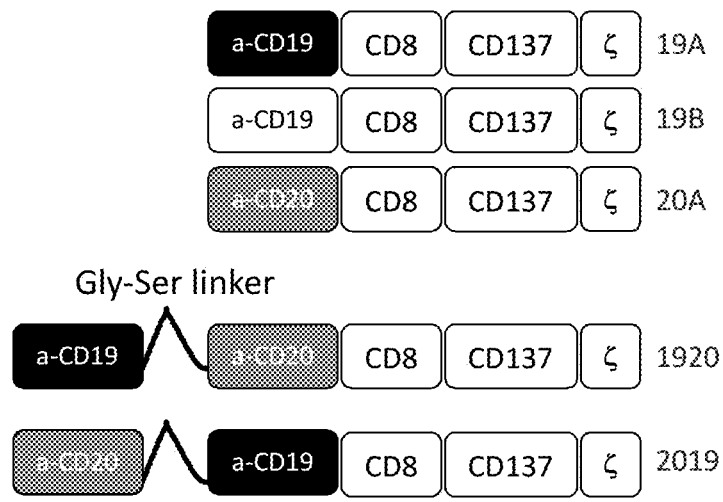
FIGS. 1A and 1B, below, depict the construction of CARs targeting CD19 and CD20.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes."

Thus, "comprising an antigen" means "including an antigen" without excluding other elements. The phrase "and/or" means "and" or "or." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

The term "about" when referring to a measurable value such as an amount, a temporal duration, and the like, is meant to encompass variations of .+−0.20% or in some instances .+−0.10%, or in some instances .+−0.5%, or in some instances .+−0.1%, or in some instances .+−0.0.1% from the specified value, as such variations are appropriate to perform the disclosed methods.

Unless otherwise noted, the technical terms herein are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

The present disclosure provides for CD19/CD20 antibodies or fragments thereof as well as chimeric antigen receptors (CARs) having such CD19/CD20 antigen binding domains. The enhancement of the functional activity of the CAR directly relates to the enhancement of functional activity of the CAR-expressing T cell. As a result of one or more of these modifications, the CARs exhibit both a high degree of cytokine-induced cytolysis and cell surface expression on transduced T cells, along with an increased level of in vivo T cell expansion and persistence of the transduced CAR-expressing T cell. The CARs of the present disclosure are advantageous in that one CART lentiviral product may be utilized to treat multiple patient populations (i.e. CD19+, CD20+ or double CD19+CD20+ cancer patients), which allows flexibility in circumstances where resources are limited.

The unique ability to combine functional moieties derived from different protein domains has been a key innovative feature of Chimeric Antigen Receptors (CARs). The choice of each of these protein domains is a key design feature, as is the way in which they are specifically combined. Each design domain is an essential component that can be used across different CAR platforms to engineer the function of lymphocytes. For example, the choice of the extracellular binding domain can make an otherwise ineffective CAR be effective.

The invariable framework components of the immunoglobulin-derived protein sequences used to create the extracellular antigen binding domain of a CAR can either be entirely neutral, or they can self-associate and drive the T cell to a state of metabolic exhaustion, thus making the therapeutic T cell expressing that CAR far less effective. This occurs independently of the antigen binding function of this CAR domain. Furthermore, the choice of the intracellular signaling domain(s) also can govern the activity and the durability of the therapeutic lymphocyte population used for immunotherapy. While the ability to bind target antigen and the ability to transmit an activation signal to the T cell through these extracellular and intracellular domains, respectively, are important CAR design aspects, what has also become apparent is that the choice of the source of the extracellular antigen binding fragments can have a significant effect on the efficacy of the CAR and thereby have a defining role for the function and clinical utility of the CAR.

The CARs disclosed herein are expressed at a high level in a cell. A cell expressing the CAR has a high in vivo proliferation rate, produces large amounts of cytokines, and has a high cytotoxic activity against a cell having, on its surface, a CD19/CD20 antigen to which a CAR binds. The use of an extracellular CD19/CD20 antigen binding domain results in generation of a CAR that functions better in vivo, while avoiding the induction of anti-CAR immunity in the host immune response and the killing of the CAR T cell population. The CARs expressing the extracellular CD19/CD20 ScFv antigen binding domain exhibit superior activities/properties including i) prevention of poor CAR T persistence and function as seen with mouse-derived binding sequences; ii) lack of regional (i.e. intrapleural) delivery of the CAR to be efficacious; and iii) ability to generate CAR T cell designs based both on binders with high and low affinity to CD19/CD20. This latter property allows investigators to better tune efficacy vs toxicity, and/or tissue specificity of the CAR T product, since lower-affinity binders may have higher specificity to tumors vs normal tissues due to higher expression of CD19/CD20 on tumors than normal tissue, which may prevent on-target off tumor toxicity and bystander cell killing.

What follows is a detailed description of the inventive CARs including a description of their extracellular CD19/CD20 antigen binding domain, the transmembrane domain and the intracellular domain, along with additional description of the CARs, antibodies and antigen binding fragments thereof, conjugates, nucleotides, expression, vectors, and host cells, methods of treatment, compositions, and kits employing the disclosed CARs.

A. Chimeric Antigen Receptors (CARs)

The CARs disclosed herein comprise at least one CD19/CD20 antigen binding domain capable of binding to CD19/CD20, at least one transmembrane domain, and at least one intracellular domain.

A chimeric antigen receptor (CAR) is an artificially constructed hybrid protein or polypeptide containing the antigen binding domains of an antibody (e.g., single chain variable fragment (ScFv)) linked to T-cell signaling domains via the transmembrane domain. Characteristics of CARs include their ability to redirect T-cell specificity and reactivity toward a selected target in a non-MHC-restricted manner, and exploiting the antigen-binding properties of monoclonal antibodies. The non-WIC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

As disclosed herein, the intracellular T cell signaling domains of the CARs can include, for example, a T cell receptor signaling domain, a T cell costimulatory signaling domain, or both. The T cell receptor signaling domain refers to a portion of the CAR comprising the intracellular domain of a T cell receptor, such as, for example, and not by way of limitation, the intracellular portion of the CD3 zeta protein. The costimulatory signaling domain refers to a portion of the CAR comprising the intracellular domain of a costimulatory molecule, which is a cell surface molecule other than an antigen receptor or their ligands that are required for an efficient response of lymphocytes to antigen.

1. Extracellular Domain

In one embodiment, the CAR comprises a target-specific binding element otherwise referred to as an antigen binding domain or moiety. The choice of domain depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen binding domain in the CAR include those associated with viral, bacterial and parasitic infections, autoimmune disease and cancer cells.

In one embodiment, the CAR can be engineered to target a tumor antigen of interest by way of engineering a desired antigen binding domain that specifically binds to an antigen on a tumor cell. Tumor antigens are proteins that are produced by tumor cells that elicit an immune response, particularly T-cell mediated immune responses. The selection of the antigen binding domain will depend on the particular type of cancer to be treated. Tumor antigens include, for example, a glioma-associated antigen, carcinoembryonic antigen (CEA), .beta.-human chorionic gonadotropin, alphafetoprotein (AFP), lectin-reactive AFP, thyroglobulin, RAGE-1, MN-CA IX, human telomerase reverse transcriptase, RUL RU2 (AS), intestinal carboxyl esterase, mut hsp70-2, M-CSF, prostase, prostate-specific antigen (PSA), PAP, NY-ESO-1, LAGE-la, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and CD19/CD20. The tumor antigens disclosed herein are merely included by way of example. The list is not intended to be exclusive and further examples will be readily apparent to those of skill in the art.

In one embodiment, the tumor antigen comprises one or more antigenic cancer epitopes associated with a malignant tumor. Malignant tumors express a number of proteins that can serve as target antigens for an immune attack. These molecules include, but are not limited to, tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20, CD22, BCMA, ROR1, and CD37 are other candidates for target antigens in B-cell lymphoma. Some of these antigens (CEA, HER-2, CD19, CD20, idiotype) have been used as targets for passive immunotherapy with monoclonal antibodies with limited success.

In one preferred embodiment, the tumor antigen is CD19/CD20 and the tumors associated with expression of CD19/CD20 comprise lung mesothelioma, ovarian, and pancreatic cancers that express high levels of the extracellular protein CD19/CD20, or any combination thereof.

The type of tumor antigen may also be a tumor-specific antigen (TSA) or a tumor-associated antigen (TAA). A TSA is unique to tumor cells and does not occur on other cells in the body. A TAA is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSAs or TAAs include the following: Differentiation antigens such as MART-1/MelanA (MART-I), gp100 (Pmel 17), tyrosinase, TRP-1, TRP-2 and tumor-specific multi-lineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In one embodiment, the antigen binding domain portion of the CAR targets an antigen that includes but is not limited to CD19, CD20, CD22, ROR1, CD33, CD38, CD123, CD138, BCMA, c-Met, PSMA, Glycolipid F77, EGFRvIII, GD-2, FGFR4, TSLPR, NY-ESO-1 TCR, MAGE A3 TCR, and the like.

In a preferred embodiment, the antigen binding domain portion of the CAR targets the extracellular CD19/CD20 antigen.

Figure 1B:
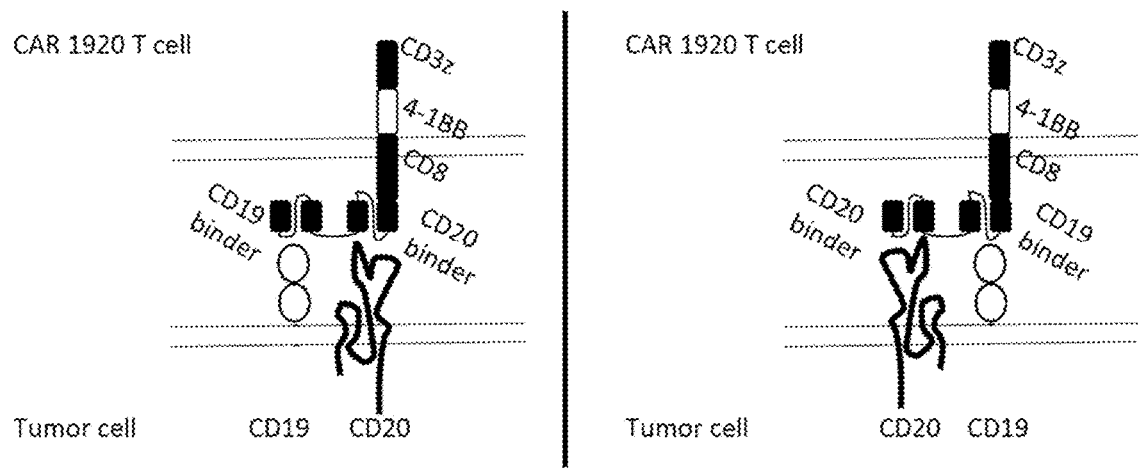

In the various embodiments of the CD19/CD20-specific CARs disclosed herein, the general scheme is set forth in FIGS. 1A and 1B and includes, from the N-terminus to the C-terminus, a signal or leader peptide, anti-CD19/CD20 ScFv, extracellular linker, CD8 transmembrane, 4-1BB, CD3 zeta.

In one embodiment, the nucleic acid sequence encoding a CAR comprises the nucleic acid sequence of SEQ ID NO: 1 (Leader-CD19 VL-Whitlow linker CD19 VH (GGGGS)-5 CD20 VH (GGGGS)-3 CD20 VL CD8 hinge+TM-4-1BB-CD3z (Construct 1920)), and encodes the CAR comprising the amino acid sequence as set forth in SEQ ID NO: 2 (Leader-CD19 VL-Whitlow linker CD19 VH (GGGGS)-5 CD20 VH (GGGGS)-3 CD20 VL CD8 hinge+TM-4-1BB-CD3z (Construct 1920) amino acid sequence (as depicted in FIG. 10A)].

In one embodiment, the nucleic acid sequence encoding a CAR comprises the nucleic acid sequence of SEQ ID NO: 1, or a sequence with 85%, 90%, 95%, 96%, 97%, 98% or 99% identity thereof, and encodes the CAR comprising the amino acid sequence as set forth in SEQ ID NO: 2 or a sequence with 85%, 90%, 95%, 96%, 97%, 98% or 99% identity thereof (Leader-CD19 VL-Whitlow linker CD19

VH (GGGGS)-5 CD20 VH (GGGGS)-3 CD20 VL CD8 hinge+TM-4-1BB-CD3z (Construct 1920)) amino acid sequence (as depicted in FIG. 10A)].

In another embodiment, the nucleic acid sequence encoding a CAR comprises the nucleic acid sequence of SEQ ID NO: 3 (Leader-CD20 VH (GGGGS)3-CD20 VL-(GGGGS) 5-CD19 VL-Whitlow linker-CD19 VH CD8 hinge+TM-4-1BB-CD3z (Construct 2019) (FIG. 2B))), and encodes the CAR comprising the amino acid sequence as set forth in SEQ ID NO: 4 [Leader-CD20 VH (GGGGS)3-CD20 VL-(GGGGS)5-CD19 VL-Whitlow linker-CD19 VH CD8 hinge+TM-4-1BB-CD3z CAR amino acid sequence (as depicted in FIG. 10B)].

In another embodiment, the nucleic acid sequence encoding a CAR comprises the nucleic acid sequence of SEQ ID NO: 3 or a sequence with 85%, 90%, 95%, 96%, 97%, 98% or 99% identity thereof, and encodes the CAR comprising the amino acid sequence as set forth in SEQ ID NO: 4 or a sequence with 85%, 90%, 95%, 96%, 97%, 98% or 99% identity thereof [Leader-CD20 VH (GGGGS)3-CD20 VL-(GGGGS)5-CD19 VL-Whitlow linker-CD19 VH CD8 hinge+TM-4-1BB-CD3z CAR amino acid sequence (as depicted in FIG. 10B)].

The surface expression of anti-CD19/CD20 CARs incorporating single chain fragment variable (ScFv) sequences reactive with CD19/CD20 antigen, is shown in Example 1 infra. The expression level for each ScFv—containing CAR was determined by flow cytometric analysis of LV-transduced T cells from healthy donors using one of three detection methods: i) Protein L-Biotin, followed by Streptavidin PE; ii) CD19 Fc recombinant protein, followed by anti Fc AF647 (APC); iii) recombinant CD20 Biotin conjugate, followed by Streptavidin PE. The ScFv-based anti-CD19/CD20 CAR constructs LTG1920 and LTG 2019 were highly expressed in human primary T cells (as indicated by the gated population) as compared to non-transduced T cell controls (non-gated cell population).

Figure 3A:
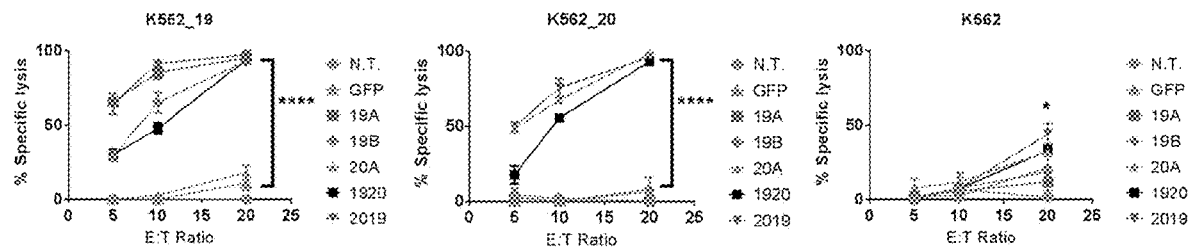
FIGS. 3A and 3B, below, depict CAR T cytotoxicity in vitro. Luciferase-based cytotoxicity assays were performed using, K562, K562 CD19+, or K562 CD20+ cell lines (FIG. 3A), or leukemia or lymphoma cell lines (Raji, NALM6, REH.
Figure 3B:
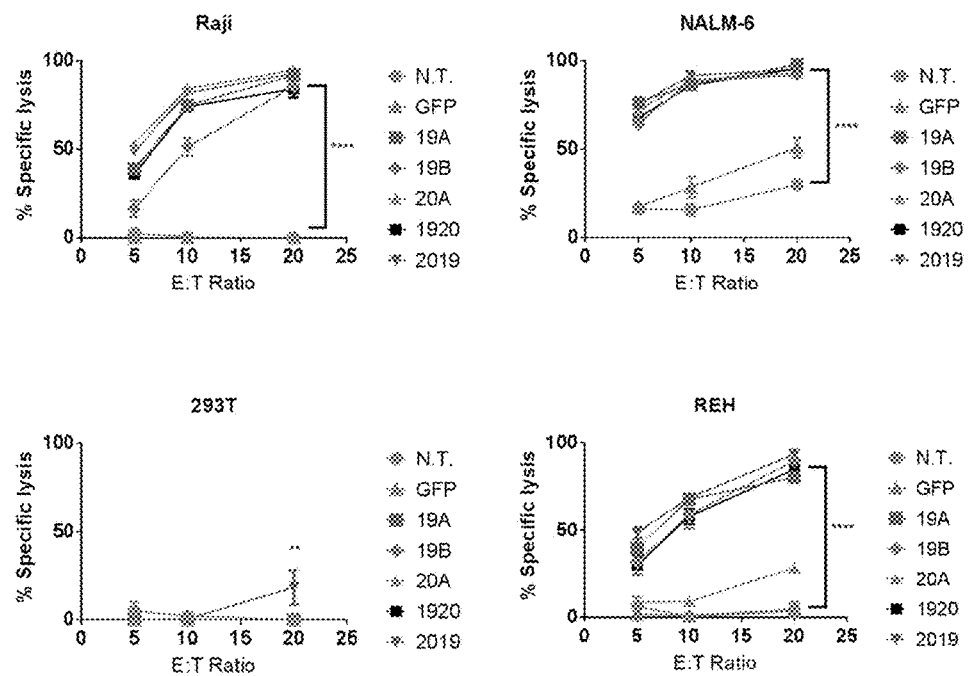

As shown in Example 1 and FIGS. 3A and 3B, high cytolytic activity of the CD19/CD20 CARs was demonstrated. Human primary T cells were transduced with LV encoding CAR constructs (19A, 19B, 20A, 1920, 2019, see Methods), then incubated for 18 hours with the Raji, NALM-6, REH, K562 or 293T cell lines, stably transduced with firefly luciferase, for luminescence based in vitro killing assays. All leukemia lines tested express CD19 on their surface, while the negative controls, K562 and 293T do not. CD20 expression varied between tumor lines. The Raji line is CD20 positive, while REH are CD20 negative, as are the control lines K562 and 293T. NALM-6 line has a weak but detectable expression of CD20. As additional controls, K562 lines were created that express CD19 (K562-19+), or CD20 (K562-20+).

K562-19+ were lysed by the CAR 19A and 19B constructs, tandem-CAR constructs 1920 and 2019, but not the single 20A CAR, FIG. 3A. K562-CD20+ were lysed by all CART constructs except for the single CAR19 constructs, demonstrating target antigen-restricted killing. Similar results were seen with the other leukemia cell lines tested. Single- and tandem-CAR T constructs targeting CD19 lysed Raji, NALM-6, and REH; but not 293T, FIG. 3B, or K562, FIG. 3A. Notably, the 20A single targeting CAR construct had no specific killing activity against the CD20-negative REH line, but did demonstrate killing of NALM-6, which has low but detectable levels of CD20 surface expression. In addition, the tandem-CAR 1920, which appeared to show lower binding to CD20 peptide than to CD19-Fc by flow cytometry, also has lower cytotoxicity against K562-19+ and K562-20+, but not against the CD19+CD20-REH. This may suggest that the 1920 tandem-CAR is inferior to 2019 tandem-CAR for some tumor targets.

The capacity of anti-CD19/CD20 CAR T cells for cytokine secretion was then evaluated. Tumor cells were co-incubated with CAR T cells or control T cells at effector to target ratio of 10:1 overnight, and culture supernatants were analyzed by ELISA for IFN gamma, TNF alpha, IL-2, and GM-CSF (c.f., FIG. 4). All CAR T groups induced cytokines in response to tumor cells, whereas the negative controls (untransduced, N.T.) and GFP yielded no appreciable cytokine induction. Of the five CAR T groups, the single CAR T 20A produced the highest level of cytokines, whereas the 19A and 19B CAR T had the lowest level of induction of cytokines. Notably, tandem CAR T-expressing cells LTG1920 and/or LTG2019 showed intermediate levels of IFN gamma, TNF alpha, IL-2, and GM-CSF, which may prove useful of the context of the clinical safety and avoidance of cytokine release syndrome.

Without being intended to limit to any particular mechanism of action, it is believed that possible reasons for the enhanced therapeutic function associated with the exemplary CARs of the invention include, for example, and not by way of limitation, a) improved lateral movement within the plasma membrane allowing for more efficient signal transduction, b) superior location within plasma membrane microdomains, such as lipid rafts, and greater ability to interact with transmembrane signaling cascades associated with T cell activation, c) superior location within the plasma membrane by preferential movement away from dampening or down-modulatory interactions, such as less proximity to or interaction with phosphatases such as CD45, and d) superior assembly into T cell receptor signaling complexes (i.e. the immune synapse), or any combination thereof.

While the disclosure has been illustrated with an exemplary extracellular CD19/CD20 variable heavy chain only and ScFv antigen binding domains, other nucleotide and/or amino acid variants within the CD19/CD20 variable heavy chain only and ScFv antigen binding domains may be used to derive the CD19/CD20 antigen binding domains for use in the CARs described herein.

Depending on the desired antigen to be targeted, the CAR can be additionally engineered to include the appropriate antigen binding domain that is specific to the desired antigen target. For example, if CD19/CD20 is the desired antigen that is to be targeted, an antibody for CD19/CD20 can be used as the antigen bind domain incorporation into the CAR.

In one exemplary embodiment, the antigen binding domain portion of the CAR additionally targets CD33. Preferably, the antigen binding domain in the CAR is anti-CD33 ScFv, wherein the nucleic acid sequence of the anti-CD33 ScFv comprises the sequence set forth in SEQ ID NO: 46. In one embodiment, the anti-CD33 ScFv comprises the nucleic acid sequence that encodes the amino acid sequence of SEQ ID NO: 46. In another embodiment, the anti-CD19/CD20 ScFv portion of the CAR comprises the amino acid sequence set forth in SEQ ID NO: 47.

In one exemplary embodiment, the antigen binding domain portion of the CAR additionally targets mesothelin. Preferably, the antigen binding domain in the CAR is anti-mesothelin ScFv, wherein the nucleic acid sequence of the anti-mesothelin ScFv comprises the sequence set forth in SEQ ID NO: 48. In one embodiment, the anti-mesothelin ScFv comprises the nucleic acid sequence that encodes the amino acid sequence of SEQ ID NO: 48. In another embodiment, the anti-mesothelin ScFv portion of the CAR comprises the amino acid sequence set forth in SEQ ID NO: 49.

In one aspect of the present invention, there is provided a CAR capable of binding to a non-TSA or non-TAA including, for example and not by way of limitation, an antigen derived from Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus, or any combination thereof.

In another aspect of the present invention, there is provided a CAR capable of binding to an antigen derived from a bacterial strain of Staphylococci, Streptococcus, Escherichia coli, Pseudomonas, or Salmonella. Particularly, there is provided a CAR capable of binding to an antigen derived from an infectious bacterium, for example, Helicobacter pyloris, Legionella pneumophilia, a bacterial strain of Mycobacteria sps. (e.g. M. tuberculosis, M. avium, M. intracellulare, M. kansaii, or M. gordonea), Staphylococcus aureus, Neisseria gonorrhoeae, Neisseria meningitides, Listeria monocytogenes, Streptococcus pyogenes, Group A Streptococcus, Group B Streptococcus (Streptococcus agalactiae), Streptococcus pneumoniae, or Clostridium tetani, or a combination thereof.

2. Transmembrane Domain

With respect to the transmembrane domain, the CAR comprises one or more transmembrane domains fused to the extracellular CD19/CD20 antigen binding domain of the CAR.

The transmembrane domain may be derived either from a natural or from a synthetic source. Where the source is natural, the domain may be derived from any membrane-bound or transmembrane protein.

Transmembrane regions of particular use in the CARs described herein may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, mesothelin, CD33, CD37, CD64, CD80, CD83, CD86, CD134, CD137, CD154, TNFRSF16, or TNFRSF19. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In one embodiment, the transmembrane domain that naturally is associated with one of the domains in the CAR is used in addition to the transmembrane domains described supra.

In some instances, the transmembrane domain can be selected or by amino acid substitution to avoid binding of such domains to the transmembrane domains of the same or different surface membrane proteins to minimize interactions with other members of the receptor complex.

In one embodiment, the transmembrane domain in the CAR of the invention is the CD8 transmembrane domain. In one embodiment, the CD8 transmembrane domain comprises the nucleic acid sequence of SEQ ID NO: 35. In one embodiment, the CD8 transmembrane domain comprises the nucleic acid sequence that encodes the amino acid sequence of SEQ ID NO: 36. In another embodiment, the CD8 transmembrane domain comprises the amino acid sequence of SEQ ID NO: 36.

In one embodiment, the encoded transmembrane domain comprises an amino acid sequence having at least one, two or three modifications (e.g., substitutions) but not more than 20, 10 or 5 modifications (e.g., substitutions) of an amino acid sequence of SEQ ID NO: 28, or a sequence with 95-99% identity to an amino acid sequence of SEQ ID NO: 28.

In some instances, the transmembrane domain of the CAR comprises the CD8.alpha.hinge domain. In one embodiment, the CD8 hinge domain comprises the nucleic acid sequence of SEQ ID NO: 37. In one embodiment, the CD8 hinge domain comprises the nucleic acid sequence that encodes the amino acid sequence of SEQ ID NO: 38. In another embodiment, the CD8 hinge domain comprises the amino acid sequence of SEQ ID NO: 38, or a sequence with 95-99% identify thereof.

In one embodiment, an isolated nucleic acid molecule is provided wherein the encoded linker domain is derived from the extracellular domain of CD8, and is linked to the transmembrane CD8 domain, the transmembrane CD28 domain, or a combination thereof.

3. Spacer Domain

In the CAR, a spacer domain can be arranged between the extracellular domain and the transmembrane domain, or between the intracellular domain and the transmembrane domain. The spacer domain means any oligopeptide or polypeptide that serves to link the transmembrane domain with the extracellular domain and/or the transmembrane domain with the intracellular domain. The spacer domain comprises up to 300 amino acids, preferably 10 to 100 amino acids, and most preferably 25 to 50 amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

The spacer domain preferably has a sequence that promotes binding of a CAR with an antigen and enhances signaling into a cell. Examples of an amino acid that is expected to promote the binding include cysteine, a charged amino acid, and serine and threonine in a potential glycosylation site, and these amino acids can be used as an amino acid constituting the spacer domain.

As the spacer domain, the entire or a part of amino acid numbers 137-206 (SEQ ID NO: 39) which is a hinge region of CD8.alpha. (NCBI RefSeq: NP.sub.-001759.3), amino acid numbers 135 to 195 of CD8.beta. (GenBank: AAA35664.1), amino acid numbers 315 to 396 of CD4 (NCBI RefSeq: NP.sub.-000607.1), or amino acid numbers 137 to 152 of CD28 (NCBI RefSeq: NP.sub.-006130.1) can be used. Also, as the spacer domain, a part of a constant region of an antibody H chain or L chain can be used. Further, the spacer domain may be an artificially synthesized sequence.

Further, in the CAR, a signal peptide sequence can be linked to the N-terminus. The signal peptide sequence exists at the N-terminus of many secretory proteins and membrane proteins, and has a length of 15 to 30 amino acids. Since many of the protein molecules mentioned above as the intracellular domain have signal peptide sequences, the signal peptides can be used as a signal peptide for the CAR. In one embodiment, the signal peptide comprises the amino acid sequence shown in SEQ ID NO: 18.

4. Intracellular Domain

The cytoplasmic domain or otherwise the intracellular signaling domain of the CAR is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the CARS disclosed herein include those derived from TCR zeta (CD3 Zeta), FcR gamma, FcR beta, CD3 gamma, CD3 delta, CD3 epsilon, CD5, CD22, CD79a, CD79b, and CD66d. Specific, non-limiting examples, of the ITAM include peptides having sequences of amino acid numbers 51 to 164 of CD3.zeta. (NCBI RefSeq: NP.sub.-932170.1), amino acid numbers 45 to 86 of Fc.epsilon.RI.gamma. (NCBI RefSeq: NP.sub.-004097.1), amino acid numbers 201 to 244 of Fc.epsilon.RI.beta. (NCBI RefSeq: NP.sub.-000130.1), amino acid numbers 139 to 182 of CD3.gamma. (NCBI RefSeq: NP.sub.-000064.1), amino acid numbers 128 to 171 of CD3.delta. (NCBI RefSeq: NP.sub.-000723.1), amino acid numbers 153 to 207 of CD3.epsilon. (NCBI RefSeq: NP.sub.-000724.1), amino acid numbers 402 to 495 of CD5 (NCBI RefSeq: NP.sub.-055022.2), amino acid numbers 707 to 847 of 0022 (NCBI RefSeq: NP.sub.-001762.2), amino acid numbers 166 to 226 of CD79a (NCBI RefSeq: NP.sub.-001774.1), amino acid numbers 182 to 229 of CD79b (NCBI RefSeq: NP.sub.-000617.1), and amino acid numbers 177 to 252 of CD66d (NCBI RefSeq: NP.sub.-001806.2), and their variants having the same function as these peptides have. The amino acid number based on amino acid sequence information of NCBI RefSeq ID or GenBank described herein is numbered based on the full length of the precursor (comprising a signal peptide sequence etc.) of each protein.

In one embodiment, the cytoplasmic signaling molecule in the CAR comprises a cytoplasmic signaling sequence derived from CD3 zeta.

In a preferred embodiment, the intracellular domain of the CAR can be designed to comprise the CD3-zeta signaling domain by itself or combined with any other desired cytoplasmic domain(s) useful in the context of the CAR. For example, the intracellular domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such costimulatory molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Specific, non-limiting examples, of such costimulatory molecules include peptides having sequences of amino acid numbers 236 to 351 of CD2 (NCBI RefSeq: NP.sub.-001758.2), amino acid numbers 421 to 458 of CD4 (NCBI RefSeq: NP.sub.-000607.1), amino acid numbers 402 to 495 of CD5 (NCBI RefSeq: NP.sub.-055022.2), amino acid numbers 207 to 235 of CD8.alpha. (NCBI RefSeq: NP.sub.-001759.3), amino acid numbers 196 to 210 of CD83 (GenBank: AAA35664.1), amino acid numbers 181 to 220 of CD28 (NCBI RefSeq: NP.sub.-006130.1), amino acid numbers 214 to 255 of CD137 (4-1BB, NCBI RefSeq: NP.sub.-001552.2), amino acid numbers 241 to 277 of CD134 (OX40, NCBI RefSeq: NP.sub.-003318.1), and amino acid numbers 166 to 199 of ICOS (NCBI RefSeq: NP.sub.-036224.1), and their variants having the same function as these peptides have. Thus, while the disclosure herein is exemplified primarily with 4-1BB as the co-stimulatory signaling element, other costimulatory elements are within the scope of the disclosure.

The cytoplasmic signaling sequences within the cytoplasmic signaling portion of the CAR may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the intracellular domain is designed to comprise the signaling domain of CD3-zeta and the signaling domain of CD28. In another embodiment, the intracellular domain is designed to comprise the signaling domain of CD3-zeta and the signaling domain of 4-1BB. In yet another embodiment, the intracellular domain is designed to comprise the signaling domain of CD3-zeta and the signaling domain of CD28 and 4-1BB.

In one embodiment, the intracellular domain in the CAR is designed to comprise the signaling domain of 4-1BB and the signaling domain of CD3-zeta, wherein the signaling domain of 4-1BB comprises the nucleic acid sequence set forth in SEQ ID NO: 40 and the signaling domain of CD3-zeta comprises the nucleic acid sequence set forth in SEQ ID NO: 42.

In one embodiment, the intracellular domain in the CAR is designed to comprise the signaling domain of 4-1BB and the signaling domain of CD3-zeta, wherein the signaling domain of 4-1BB comprises the nucleic acid sequence that encodes the amino acid sequence of SEQ ID NO: 41 and the signaling domain of CD3-zeta comprises the nucleic acid sequence that encodes the amino acid sequence of SEQ ID NO: 43.

In one embodiment, the intracellular domain in the CAR is designed to comprise the signaling domain of 4-1BB and the signaling domain of CD3-zeta, wherein the signaling domain of 4-1BB comprises the amino acid sequence set forth in SEQ ID NO: 41 and the signaling domain of CD3-zeta comprises the amino acid sequence set forth in SEQ ID NO: 43.

5. Additional Description of CARs

Also expressly included within the scope of the invention are functional portions of the CARs disclosed herein. The term "functional portion" when used in reference to a CAR refers to any part or fragment of one or more of the CARs disclosed herein, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the disclosure are functional variants of the CARs disclosed herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, 50%, 75%, 80%, 90%, 98% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, He, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gin, Ser, Thr, Tyr, etc.), an amino acid with a beta-branched side-chain substituted for another amino acid with a beta-branched side-chain (e.g., He, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The CARs (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs (including functional portions and functional variants of the invention) can comprise synthetic amino acids in place of one or more naturally-occurring amino acids. Such synthetic amino acids are known in the art, and include, for example, aminocyclohexane carboxylic acid, norleucine, -amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, a-naphthylalanine, cyclohexylalanine, cyclohexylglycine, indoline-2-carboxylic acid, 1,2,3,4-tetrahydroisoquinoline carboxylic acid, aminomalonic acid, aminomalonic acid monoamide, N'-benzyl-N'-methyl-lysine, N',N'-dibenzyl-lysine, 6-hydroxylysine, ornithine, -aminocyclopentane carboxylic acid, a-aminocyclohexane carboxylic acid, α-aminocycloheptane carboxylic acid, a-(2-amino-2-norbornane)-carboxylic acid, γ-diaminobutyric acid, β-diaminopropionic acid, homophenylalanine, and a-tert-butylglycine.

The CARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs (including functional portions and functional variants thereof) can be obtained by methods known in the art. The CARs may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, N Y, 1994. Further, some of the CARs (including functional portions and functional variants thereof) can be isolated and/or purified from a source, such as a plant, a bacterium, an insect, a mammal, e.g., a rat, a human, etc. Methods of isolation and purification are well-known in the art. Alternatively, the CARs described herein (including functional portions and functional variants thereof) can be commercially synthesized by companies. In this respect, the CARs can be synthetic, recombinant, isolated, and/or purified.

B. Antibodies and Antigen Binding Fragments

One embodiment further provides a CAR, a T cell expressing a CAR, an antibody, or antigen binding domain or portion thereof, which specifically binds to one or more of the antigens disclosed herein. As used herein, a "T cell expressing a CAR," or a "CAR T cell" means a T cell expressing a CAR, and has antigen specificity determined by, for example, the antibody-derived targeting domain of the CAR.

As used herein, and "antigen binding domain" can include an antibody and antigen binding fragments thereof. The term "antibody" is used herein in the broadest sense and encompasses various antibody structures, including but not limited to monoclonal antibodies, polyclonal antibodies, multi-specific antibodies (e.g., bispecific antibodies), and antigen binding fragments thereof, so long as they exhibit the desired antigen-binding activity. Non-limiting examples of antibodies include, for example, intact immunoglobulins and variants and fragments thereof known in the art that retain binding affinity for the antigen.

A "monoclonal antibody" is an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. The modifier "monoclonal" indicates the character of the antibody as being obtained from a substantially homogeneous population of antibodies, and is not to be construed as requiring production of the antibody by any particular method. In some examples, a monoclonal antibody is an antibody produced by a single clone of B lymphocytes or by a cell into which nucleic acid encoding the light and heavy variable regions of the antibody of a single antibody (or an antigen binding fragment thereof) have been transfected, or a progeny thereof. In some examples monoclonal antibodies are isolated from a subject. Monoclonal antibodies can have conservative amino acid substitutions which have substantially no effect on antigen binding or other immunoglobulin functions. Exemplary methods of production of monoclonal antibodies are known, for example, see Harlow & Lane, Antibodies, A Laboratory Manual, 2nd ed. Cold Spring Harbor Publications, New York (2013).

Typically, an immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda ($\lambda$) and kappa ($\kappa$). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, $6^{th}$ ed., W.H. Freeman and Co., specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., Nature, 363:446-448, 1993; Sheriff et al., Nat. Struct. Biol., 3:733-736, 1996). References to "VH" or "VH" refer to the variable region of an antibody heavy chain, including that of an antigen binding fragment, such as Fv, ScFv, dsFv or Fab. References to "VL" or "VL" refer to the variable domain of an antibody light chain, including that of an Fv, ScFv, dsFv or Fab.

Light and heavy chain variable regions contain a "framework" region interrupted by three hypervariable regions, also called "complementarity-determining regions" or "CDRs" (see, e.g., Kabat et al., Sequences of Proteins of Immunological Interest, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," $5^{th}$ Ed. Public Health Service, National Institutes of Health, Bethesda, Md., 1991; "Kabat" numbering scheme), Al-Lazikani et al., (JMB 273,927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a VH CDR3 is the CDR3 from the variable domain of the heavy chain of the antibody in which it is found, whereas a VL CDR1 is the CDR1 from the variable domain of the light chain of the antibody in which it is found. Light chain CDRs are sometimes referred to as LCDR1, LCDR2, and LCDR3. Heavy chain CDRs are sometimes referred to as LCDR1, LCDR2, and LCDR3.

An "antigen binding fragment" is a portion of a full length antibody that retains the ability to specifically recognize the cognate antigen, as well as various combinations of such portions. Non-limiting examples of antigen binding fragments include Fv, Fab, Fab', Fab'-SH, F(ab')2; diabodies;

linear antibodies; single-chain antibody molecules (e.g. ScFv); and multi-specific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2nd Ed., Springer Press, 2010).

A single-chain antibody (ScFv) is a genetically engineered molecule containing the VH and VL domains of one or more antibody(ies) linked by a suitable polypeptide linker as a genetically fused single chain molecule (see, for example, Bird et al., Science, 242:423 426, 1988; Huston et al., Proc. Natl. Acad. Sci., 85:5879 5883, 1988; Ahmad et al., Clin. Dev. Immunol., 2012, doi:10.1155/2012/980250; Marbry, IDrugs, 13:543-549, 2010). The intramolecular orientation of the VH-domain and the VL-domain in a ScFv, is typically not decisive for ScFvs. Thus, ScFvs with both possible arrangements (VH-domain-linker domain-VL-domain; VL-domain-linker domain-VH-domain) may be used.

In a dsFv, the heavy and light chain variable chains have been mutated to introduce a disulfide bond to stabilize the association of the chains. Diabodies also are included, which are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., Proc. Natl. Acad. Sci., 90:6444 6448, 1993; Poljak et al., Structure, 2:1121 1123, 1994).

Antibodies also include genetically engineered forms such as chimeric antibodies (such as humanized murine antibodies) and heteroconjugate antibodies (such as bispecific antibodies). See also, Pierce Catalog and Handbook, 1994-1995 (Pierce Chemical Co., Rockford, Ill.); Kuby, J., Immunology, 3rd Ed., W.H. Freeman & Co., New York, 1997.

Non-naturally occurring antibodies can be constructed using solid phase peptide synthesis, can be produced recombinantly, or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies, are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. Phage display: A Laboratory Manuel. 1st Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Methods of testing antibodies for the ability to bind to any functional portion of the CAR are known in the art and include any antibody-antigen binding assay, such as, for example, radioimmunoassay (RIA), ELISA, Western blot, immunoprecipitation, and competitive inhibition assays (see, e.g., Janeway et al., infra, U.S. Patent Application Publication No. 2002/0197266 A1, and U.S. Pat. No. 7,338, 929).

Also, a CAR, a T cell expressing a CAR, an antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

C. Conjugates

A CAR, a T cell expressing a CAR, or monoclonal antibodies, or antigen binding fragments thereof, specific for one or more of the antigens disclosed herein, can be conjugated to an agent, such as an effector molecule or detectable marker, using any number of means known to those of skill in the art. Both covalent and noncovalent attachment means may be used. Conjugates include, but are not limited to, molecules in which there is a covalent linkage of an effector molecule or a detectable marker to an antibody or antigen binding fragment that specifically binds one or more of the antigens disclosed herein. One of skill in the art will appreciate that various effector molecules and detectable markers can be used, including (but not limited to) chemotherapeutic agents, anti-angiogenic agents, toxins, radioactive agents such as $^{125}$I, $^{32}$P, $^{14}$C, $^{3}$H and $^{35}$S and other labels, target moieties and ligands, etc.

The choice of a particular effector molecule or detectable marker depends on the particular target molecule or cell, and the desired biological effect. Thus, for example, the effector molecule can be a cytotoxin that is used to bring about the death of a particular target cell (such as a tumor cell).

The procedure for attaching an effector molecule or detectable marker to an antibody or antigen binding fragment varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, Ill. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

In some embodiments, the linker is cleavable under intracellular conditions, such that cleavage of the linker releases the effector molecule or detectable marker from the antibody or antigen binding fragment in the intracellular environment. In yet other embodiments, the linker is not cleavable and the effector molecule or detectable marker is released, for example, by antibody degradation. In some embodiments, the linker is cleavable by a cleaving agent that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15 amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, for example, a thioether attached to the therapeutic agent via an acylhydrazone bond (see, for example, U.S. Pat. No. 5,622,929).

In other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker is not cleavable and the effector molecule or detectable marker is released by antibody degradation. (See U.S. Publication No. 2005/0238649 incorporated by reference herein in its entirety).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004-010957, U.S. Publication No. 2006/0074008, U.S. Publication No. 20050238649, and U.S. Publication No. 2006/0024317, each of which is incorporated by reference herein in its entirety.

In several embodiments, conjugates of a CAR, a T cell expressing a CAR, an antibody, or antigen binding portion thereof, and one or more small molecule toxins, such as a calicheamicin, maytansinoids, dolastatins, auristatins, a trichothecene, and CC1065, and the derivatives of these toxins that have toxin activity, are provided.

Maytansine compounds suitable for use as maytansinoid toxin moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, each of which is incorporated herein by reference. Conjugates containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference.

Additional toxins can be employed with a CAR, a T cell expressing a CAR, an antibody, or antigen binding portion thereof. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, Mo.). Contemplated toxins also include variants of the toxins (see, for example, see, U.S. Pat. Nos. 5,079,163 and 4,689,401).

Saporin is a toxin derived from *Saponaria officinalis* that disrupts protein synthesis by inactivating the 60S portion of the ribosomal complex (Stirpe et al., Bio/Technology, 10:405-412, 1992). However, the toxin has no mechanism for specific entry into cells, and therefore requires conjugation to an antibody or antigen binding fragment that recognizes a cell-surface protein that is internalized in order to be efficiently taken up by cells.

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, J. Virol. 19:220, 1976), and has been used in human clinical trials. See, U.S. Pat. Nos. 5,792,458 and 5,208,021.

Ricin is the lectin $RCA_{60}$ from *Ricinus communis* (Castor bean). For examples of ricin, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, J. Biochim. Biophys. Acta 266:543, 1972). The A chain is responsible for inactivating protein synthesis and killing cells. The B chain binds ricin to cell-surface galactose residues and facilitates transport of the A chain into the cytosol (Olsnes et al., Nature 249:627-631, 1974 and U.S. Pat. No. 3,060,165).

Ribonucleases have also been conjugated to targeting molecules for use as immunotoxins (see Suzuki et al., Nat. Biotech. 17:265-70, 1999). Exemplary ribotoxins such as α-sarcin and restrictocin are discussed in, for example Rathore et al., Gene 190:31-5, 1997; and Goyal and Batra, Biochem. 345 Pt 2:247-54, 2000. Calicheamicins were first isolated from *Micromonospora echinospora* and are members of the enediyne antitumor antibiotic family that cause double strand breaks in DNA that lead to apoptosis (see, for example Lee et al., J. Antibiot. 42:1070-87,1989). The drug is the toxic moiety of an immunotoxin in clinical trials (see, for example, Gillespie et al., Ann. Oncol. 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., Agr. Biol. Chem. 52:1095, 1988; and Olsnes, Methods Enzymol. 50:330-335, 1978).

A CAR, a T cell expressing a CAR, monoclonal antibodies, antigen binding fragments thereof, specific for one or more of the antigens disclosed herein, can also be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). A CAR, a T cell expressing a CAR, an antibody, or antigen binding portion thereof, can also be conjugated with enzymes that are useful for detection, such as horseradish peroxidase, β-galactosidase, luciferase, alkaline phosphatase, glucose oxidase and the like. When a CAR, a T cell expressing a CAR, an antibody, or antigen binding portion thereof, is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. A CAR, a T cell expressing a CAR, an antibody, or antigen binding portion thereof, may also be conjugated with biotin, and detected through indirect measurement of avidin or streptavidin binding. It should be noted that the avidin itself can be conjugated with an enzyme or a fluorescent label.

A CAR, a T cell expressing a CAR, an antibody, or antigen binding portion thereof, may be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

A CAR, a T cell expressing a CAR, an antibody, or antigen binding portion thereof, can also be conjugated with a radiolabeled amino acid. The radiolabel may be used for both diagnostic and therapeutic purposes. For instance, the radiolabel may be used to detect one or more of the antigens disclosed herein and antigen expressing cells by x-ray, emission spectra, or other diagnostic techniques. Further, the radiolabel may be used therapeutically as a toxin for treatment of tumors in a subject, for example for treatment of a neuroblastoma. Examples of labels for polypeptides include, but are not limited to, the following radioisotopes or radionucleotides: $^3$H, $^{14}$C, $^{15}$N, $^{35}$S, $^{90}$Y, $^{99}$Tc, $^{111}$In, $^{125}$I, $^{131}$I.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

D. Nucleotides, Expression, Vectors, and Host Cells

Further provided by an embodiment of the invention is a nucleic acid comprising a nucleotide sequence encoding any of the CARs, an antibody, or antigen binding portion thereof, described herein (including functional portions and functional variants thereof). The nucleic acids of the invention may comprise a nucleotide sequence encoding any of the leader sequences, antigen binding domains, transmembrane domains, and/or intracellular T cell signaling domains described herein.

In some embodiments, the nucleotide sequence may be codon-modified. Without being bound to a particular theory, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

In an embodiment of the invention, the nucleic acid may comprise a codon-modified nucleotide sequence that encodes the antigen binding domain of the inventive CAR. In another embodiment of the invention, the nucleic acid may comprise a codon-modified nucleotide sequence that encodes any of the CARs described herein (including functional portions and functional variants thereof).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Integrated DNA Technologies (Coralville, Iowa, USA).

The nucleic acid can comprise any isolated or purified nucleotide sequence which encodes any of the CARs or functional portions or functional variants thereof. Alternatively, the nucleotide sequence can comprise a nucleotide sequence which is degenerate to any of the sequences or a combination of degenerate sequences.

An embodiment also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

Also provided is a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acid can be incorporated into a recombinant expression vector. In this regard, an embodiment provides recombinant expression vectors comprising any of the nucleic acids. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors are not naturally-occurring as a whole.

However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, CA), the pET series (Novagen, Madison, Wis.), the pGEX series (Pharmacia Biotech, Uppsala, Sweden), and the pEX series (Clontech, Palo Alto, Calif.).

Bacteriophage vectors, such as λGTIO, λGTl 1, λZapII (Stratagene), EMBL4, and λNMI 149, also can be used. Examples of plant expression vectors include pBIO1, pBI101.2, pBHO1 0.3, pBI121 and pBIN19 (Clontech). Examples of animal expression vectors include pEUK-Cl, pMAM, and pMAMneo (Clontech). The recombinant expression vector may be a viral vector, e.g., a retroviral vector or a lentiviral vector. A lentiviral vector is a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include, for example, and not by way of limitation, the LENTIVECTOR® gene delivery technology from Oxford BioMedica plc, the LENTIMAX™ vector system from Lentigen and the like. Nonclinical types of lentiviral vectors are also available and would be known to one skilled in the art.

A number of transfection techniques are generally known in the art (see, e.g., Graham et al., Virology, 52: 456-467 (1973); Sambrook et al., supra; Davis et al., Basic Methods in Molecular Biology, Elsevier (1986); and Chu et al, Gene, 13: 97 (1981).

Transfection methods include calcium phosphate co-precipitation (see, e.g., Graham et al., supra), direct micro injection into cultured cells (see, e.g., Capecchi, Cell, 22: 479-488 (1980)), electroporation (see, e.g., Shigekawa et al., BioTechniques, 6: 742-751 (1988)), liposome mediated gene transfer (see, e.g., Mannino et al., BioTechniques, 6: 682-690 (1988)), lipid mediated transduction (see, e.g., Feigner et al., Proc. Natl. Acad. Sci. USA, 84: 7413-7417 (1987)), and nucleic acid delivery using high velocity microprojectiles (see, e.g., Klein et al, Nature, 327: 70-73 (1987)).

In an embodiment, the recombinant expression vectors can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The recombinant expression vectors can be designed for either transient expression, for stable expression, or for both.

Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

An embodiment further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a *E. coli* cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5a cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4+/CD8+ double positive T cells, CD4+ helper T cells, e.g., Th1 and Th2 cells, CD8+ T cells (e.g., cytotoxic T cells), tumor infiltrating cells, memory T cells, memory stem cells, i.e. Tscm, naive T cells, and the like. The T cell may be a CD8+ T cell or a CD4+ T cell.

In an embodiment, the CARs as described herein can be used in suitable non-T cells. Such cells are those with an immune-effector function, such as, for example, NK cells, and T-like cells generated from pluripotent stem cells.

Also provided by an embodiment is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

CARs (including functional portions and variants thereof), nucleic acids, recombinant expression vectors, host cells (including populations thereof), and antibodies (including antigen binding portions thereof), can be isolated and/or purified. For example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

E. Methods of Treatment

It is contemplated that the CARs disclosed herein can be used in methods of treating or preventing a disease in a mammal. In this regard, an embodiment provides a method of treating or preventing cancer in a mammal, comprising administering to the mammal the CARs, the nucleic acids, the recombinant expression vectors, the host cells, the population of cells, the antibodies and/or the antigen binding portions thereof, and/or the pharmaceutical compositions in an amount effective to treat or prevent cancer in the mammal.

An embodiment further comprises lymphodepleting the mammal prior to administering the CARs disclosed herein. Examples of lymphodepletion include, but may not be limited to, nonmyeloablative lymphodepleting chemotherapy, myeloablative lymphodepleting chemotherapy, total body irradiation, etc.

For purposes of the methods, wherein host cells or populations of cells are administered, the cells can be cells that are allogeneic or autologous to the mammal. Preferably, the cells are autologous to the mammal. As used herein, allogeneic means any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically. As used herein, "autologous" means any material derived from the same individual to whom it is later to be re-introduced into the individual.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the methods, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma and lung adenocarcinoma), lymphoma, mesothelioma, mastocytoma, melanoma, multiple myeloma, nasopharynx cancer, non-Hodgkin lymphoma, B-chronic lymphocytic leukemia, hairy cell leukemia, acute lymphocytic leukemia (ALL), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, synovial sarcoma, gastric cancer, testicular cancer, thyroid cancer, and ureter cancer.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the methods can provide any amount or any level of treatment or prevention of cancer in a mammal.

Furthermore, the treatment or prevention provided by the method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment provides a method of detecting the presence of cancer in a mammal, comprising: (a) contacting a sample comprising one or more cells from the mammal with the CARs, the nucleic acids, the recombinant expression vectors, the host cells, the population of cells, the antibodies, and/or the antigen binding portions thereof, or the pharmaceutical compositions, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the method of detecting the presence of a proliferative disorder, e.g., cancer, in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

The contacting can take place in vitro or in vivo with respect to the mammal. Preferably, the contacting is in vitro.

Also, detection of the complex can occur through any number of ways known in the art. For instance, the CARs disclosed herein, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles) as disclosed supra.

Methods of testing a CAR for the ability to recognize target cells and for antigen specificity are known in the art. For instance, Clay et al., J. Immunol, 163: 507-513 (1999), teaches methods of measuring the release of cytokines (e.g., interferon-γ, granulocyte/monocyte colony stimulating factor (GM-CSF), tumor necrosis factor a (TNF-a) or interleukin 2 (IL-2)). In addition, CAR function can be evaluated by measurement of cellular cytotoxicity, as described in Zhao et al, J. Immunol, 174: 4415-4423 (2005).

Another embodiment provides for the use of the CARs, nucleic acids, recombinant expression vectors, host cells, populations of cells, antibodies, or antigen binding portions thereof, and/or pharmaceutical compositions of the invention, for the treatment or prevention of a proliferative disorder, e.g., cancer, in a mammal. The cancer may be any of the cancers described herein.

Any method of administration can be used for the disclosed therapeutic agents, including local and systemic administration. For example topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used; for example, a chemotherapeutic agent may be administered orally and an antibody or antigen binding fragment or conjugate or composition may be administered intravenously. Methods of administration include injection for which the CAR, CAR T Cell, conjugates, antibodies, antigen binding fragments, or compositions are provided in a nontoxic pharmaceutically acceptable carrier such as water, saline, Ringer's solution, dextrose solution, 5% human serum albumin, fixed oils, ethyl oleate, or liposomes. In some embodiments, local administration of the disclosed compounds can be used, for instance by applying the antibody or antigen binding fragment to a region of tissue from which a tumor has been removed, or a region suspected of being prone to tumor development. In some embodiments, sustained intra-tumoral (or near-tumoral) release of the pharmaceutical preparation that includes a therapeutically effective amount of the antibody or antigen binding fragment may be beneficial. In other examples, the conjugate is applied as an eye drop topically to the cornea, or intravitreally into the eye.

The disclosed therapeutic agents can be formulated in unit dosage form suitable for individual administration of precise dosages. In addition, the disclosed therapeutic agents may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

Typical dosages of the antibodies or conjugates can range from about 0.01 to about 30 mg/kg, such as from about 0.1 to about 10 mg/kg.

In particular examples, the subject is administered a therapeutic composition that includes one or more of the conjugates, antibodies, compositions, CARs, CAR T cells or additional agents, on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months.

In some embodiments, the disclosed methods include providing surgery, radiation therapy, and/or chemotherapeutics to the subject in combination with a disclosed antibody, antigen binding fragment, conjugate, CAR or T cell expressing a CAR (for example, sequentially, substantially simultaneously, or simultaneously). Methods and therapeutic dosages of such agents and treatments are known to those skilled in the art, and can be determined by a skilled clinician. Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

In some embodiments, the combination therapy can include administration of a therapeutically effective amount of an additional cancer inhibitor to a subject. Non-limiting examples of additional therapeutic agents that can be used with the combination therapy include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. These agents (which are administered at a therapeutically effective amount) and treatments can be used alone or in combination. For example, any suitable anti-cancer or anti-angiogenic agent can be administered in combination with the CARS, CAR-T cells, antibodies, antigen binding fragment, or conjugates disclosed herein. Methods and therapeutic dosages of such agents are known to those skilled in the art, and can be determined by a skilled clinician.

Additional chemotherapeutic agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as *podophyllum* (for example, etoposide, and teniposide), taxane (for example, docetaxel and paclitaxel), *vinca* (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, rifampicin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, pertuzumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, axitinib, bexarotene, bevacizumab, bortezomib, celecoxib, denileukin diftitox, erlotinib, estramustine, gefitinib, hydroxycarbamide, imatinib, lapatinib, pazopanib, pentostatin, masoprocol, mitotane, pegaspargase, tamoxifen, sorafenib, sunitinib, vemurafinib, vandetanib, and tretinoin. Selection and therapeutic dosages of such agents are known to those skilled in the art, and can be determined by a skilled clinician.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

In one embodiment, an effective amount of an antibody or antigen binding fragment that specifically binds to one or more of the antigens disclosed herein or a conjugate thereof is administered to a subject having a tumor following anti-cancer treatment. After a sufficient amount of time has elapsed to allow for the administered antibody or antigen binding fragment or conjugate to form an immune complex with the antigen expressed on the respective cancer cell, the immune complex is detected. The presence (or absence) of the immune complex indicates the effectiveness of the treatment. For example, an increase in the immune complex compared to a control taken prior to the treatment indicates that the treatment is not effective, whereas a decrease in the immune complex compared to a control taken prior to the treatment indicates that the treatment is effective.

F. Biopharmaceutical Compositions

Biopharmaceutical or biologics compositions (hereinafter, "compositions") are provided herein for use in gene therapy, immunotherapy and/or cell therapy that include one or more of the disclosed CARs, or T cells expressing a CAR, antibodies, antigen binding fragments, conjugates, CARs, or T cells expressing a CAR that specifically bind to one or more antigens disclosed herein, in a carrier (such as a pharmaceutically acceptable carrier). The compositions can be prepared in unit dosage forms for administration to a subject. The amount and timing of administration are at the discretion of the treating clinician to achieve the desired outcome. The compositions can be formulated for systemic (such as intravenus) or local (such as intra-tumor) administration. In one example, a disclosed CARs, or T cells expressing a CAR, antibody, antigen binding fragment, conjugate, is formulated for parenteral administration, such as intravenous administration. Compositions including a CAR, or T cell expressing a CAR, a conjugate, antibody or antigen binding fragment as disclosed herein are of use, for example, for the treatment and detection of a tumor, for example, and not by way of limitation, a neuroblastoma. In some examples, the compositions are useful for the treatment or detection of a carcinoma. The compositions including a CAR, or T cell expressing a CAR, a conjugate, antibody or antigen binding fragment as disclosed herein are also of use, for example, for the detection of pathological angiogenesis.

The compositions for administration can include a solution of the CAR, or T cell expressing a CAR, conjugate, antibody or antigen binding fragment dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents, adjuvant agents, and the like, for example, sodium acetate, sodium chloride, potassium chloride, calcium chloride, sodium lactate and the like. The concentration of a CAR, or T cell expressing a CAR, antibody or antigen binding fragment or conjugate in these formulations can vary widely, and will be selected primarily based on fluid volumes, viscosities, body weight and the like in accordance with the particular mode of administration selected and the subject's needs. Actual methods of preparing such dosage forms for use in in gene therapy, immunotherapy and/or cell therapy are known, or will be apparent, to those skilled in the art.

A typical composition for intravenous administration includes about 0.01 to about 30 mg/kg of antibody or antigen binding fragment or conjugate per subject per day (or the corresponding dose of a CAR, or T cell expressing a CAR, conjugate including the antibody or antigen binding fragment). Actual methods for preparing administrable compositions will be known or apparent to those skilled in the art and are described in more detail in such publications as *Remington's Pharmaceutical Science, 19th ed.*, Mack Publishing Company, Easton, Pa. (1995).

A CAR, or T cell expressing a CAR, antibodies, antigen binding fragments, or conjugates may be provided in lyophilized form and rehydrated with sterile water before administration, although they are also provided in sterile solutions of known concentration. The CARs, or T cells expressing a CAR, antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the administration of antibody or antigen binding fragment and conjugate drugs; for example, antibody drugs have been marketed in the U.S. since the approval of RITUXAN® in 1997. A CAR, or T cell expressing a CAR, antibodies, antigen binding fragments and conjugates thereof can be administered by slow infusion, rather than in an intravenous push or bolus. In one example, a higher loading dose is administered, with subsequent, maintenance doses being administered at a lower level. For example, an initial loading dose of 4 mg/kg antibody or antigen binding fragment (or the corresponding dose of a conjugate including the antibody or antigen binding fragment) may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres, the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the CARs, or T cells expressing a CAR, antibody or antigen binding fragment or conjugate compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., J. Parent. Sci. Tech. 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

G. Kits

In one aspect, kits employing the CARs disclosed herein are also provided. For example, kits for treating a tumor in a subject, or making a CAR T cell that expresses one or more of the CARs disclosed herein. The kits will typically include a disclosed antibody, antigen binding fragment, conjugate, nucleic acid molecule, CAR or T cell expressing a CAR as disclosed herein. More than one of the disclosed antibodies, antigen binding fragments, conjugates, nucleic acid molecules, CARs or T cells expressing a CAR can be included in the kit.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, CARs or T cells expressing a CAR. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of a disclosed antibodies, antigen binding fragments, conjugates, nucleic acid molecules, CARs or T cells expressing a CAR, for example, in a method of treating or preventing a tumor or of making a CAR T cell. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

A Tandem CD19/CD20 CAR Lentiviral Vector Drives On-Target and Off-Target Antigen Modulation in Leukemia Cell Lines Adoptive immunotherapy for cancer with genetically engineered autologous human T cells is currently being evaluated in numerous centers. One common approach to creating a cell population for adoptive immunotherapy is to isolate T cells by apheresis from the patient and to transduce these cells ex vivo with retroviral or lentiviral vectors that integrate into the host genome and express a chimeric antigen receptor (CAR), reviewed in [1]. Chimeric antigen receptors are created by linking functional sequence domains from different subunits of immunologically active proteins. For example, an scFv domain created from the VH and VL domains of an anti-CD19 or anti-CD20 antibody can be linked to transmembrane sequences derived from CD28 or CD8, and then linked to the intracellular signaling domains derived from the CD3-zeta chain and CD28 or CD137 [2, 3]. The CAR thus confers both a binding domain derived from the scFv and the linked signaling domains in a single transmembrane protein that allows activation of a vector-transduced T cells. This transduced T cell population (CAR-T) can now functionally target cells bearing the cognate antigen for destruction by active cytolysis, and by indirect immune effector mechanisms marshaled by the production of cytokines, such as interferon-gamma (IFNγ), interleukin-2 (IL-2), and tumor necrosis factor-alpha (TNFα). Adoptive immunotherapy with chimeric antigen receptor modified T cells that specifically target CD19 has proven efficacy against pediatric pre-B ALL [4, 5]. The effectiveness of CAR-modified T cells in adult hematologic malignancies has been more heterogeneous.

While the experience with anti-CD19 CAR-T therapy at the University of Pennsylvania with 3 CLL patients seemed to indicate a universal positive response, the Surgery Branch at the NCI reported a mixture of partial responses, stable disease, and one complete response in a diverse collection of 8 patients with adult B cell malignancies [6, 7]. Thus, the anti-CD19 CAR is not universally effective and may benefit from further enhancement of its anti-tumor targeting potential. The laboratory of Thomas-Tikhonenko has elegantly described the escape mechanisms employed by B-ALL during anti-CD19 CAR-T therapy which include alternative splicing of CD19, frameshift mutations, and missense mutations [8]. One means to both broaden the target range of a CAR-T product as well as to target malignancies with greater effect is to include two binding domains in a single CAR structure. Tandem CD19- and CD20-expressing malignancies include chronic lymphocytic leukemia (CLL), hairy cell leukemia (HCL), mantle cell lymphoma (MCL), prolymphocytic leukemia (PLL), and splenic lymphoma with villous lymphocytes (SLVL) [9]. A single CAR vector targeting both antigens would target a broader variety of hematologic malignancies, and potentially target them more effectively.

In this Example, the increased effectiveness of a tandem-CAR construct is modeled by testing the expression of both target antigens on the CD19+CD20+ Raji cell line upon co-culture with a series of both single specificity and tandem-specific CAR-T constructs. A rapid CD19 target antigen down modulation mechanism present is demonstrated in this leukemia cell line. Surprisingly, target antigen down-modulation also included non-targeted B cell receptor molecules, including CD22, which is not targeted by any of the vector constructs. The more rapid loss in target cell number with our tandem targeting vector indicates the presence of stronger anti-leukemic immune pressure. The kinetics of the escape from immune pressure by the leukemia cell line, especially when single specificity CARs are used, indicates that antigenic modulation is a pre-existing property of the leukemia cell, as opposed to a mechanisms of target antigen modulation or loss that is dependent on selection for genetic escape mutants.

Materials and Methods
Cell Lines (PBMC and Targets)

All cell lines and reagents were purchased from American Tissue Culture Collection (ATCC, Manassas, Va.), unless otherwise noted. The Burkitt lymphoma cell line Raji the acute lymphocytic leukemia cell lines REH and NALM-6 (ACC-128 DSMZ, Leibniz Institute DSMZ, Braunschwieg, Germany), as well as the chronic myelogenous leukemia line K562 were cultured in RPMI-1640 medium supplemented with 10% heat-inactivated fetal bovine serum (FBS, Hyclone, Logan, Utah) and 2 mM L-Glutamax (Thermo Fisher Scientific, Grand Island, N.Y.). The human embryonic kidney cell line 293T was propagated in Dulbecco's modified Eagle medium supplemented with 10% heat-inactivated FBS.

Single-cell clones of luciferase-expressing cell lines were generated by stably transducing wild-type tumor lines with lentiviral vector encoding firefly luciferase (Lentigen Technology, Inc., Gaithersburg, Md.), followed by cloning and selection of luciferase-positive clones. The mouse-adapted Raji-luc line was generated by engrafting a Raji clone stably expressing firefly luciferase into NSG mice (NOD.Cg-Prkdcscid Il2rgtm1Wjl/SzJ), The Jackson Laboratory Sacramento, Calif.), isolating the engrafted Raji-luc tumor cells from mouse spleens by either positive (CD19 microBeads, human, Miltenyi Biotec, Bergisch Gladbach, Germany) or negative selection (mouse cell depletion kit, Miltenyi Biotec), expanding in culture, and re-cloning to facilitate the selection of clones with high expression of firefly luciferase, as previously described for the NALM6 cell line [10].

Whole blood was collected from healthy volunteers at Oklahoma Blood Institute (OBI) with donors' written consent. Processed buffy coats were purchased from OBI (Oklahoma City, Okla.). The CD4-positive and CD8-positive human T cells were purified from buffy coats via positive selection using a 1:1 mixture of CD4- and CD8-MicroBeads (Miltenyi Biotec) according to manufacturer's protocol.

Creation of Chimeric Antigen Receptor (CAR)—Expressing Vectors

CAR antigen-binding domains, scFv, sequences were derived from the mouse hybridoma FMC-63 for CD19 (FMC-63: AA 1-267, GenBank ID: HM852952.1) and Leu-16 for CD20 [15], entire sequence of VL and VH), as in Additional files section.

CAR19A, CAR19B and CAR20A were generated by linking scFv of each antibody in frame to CD8 hinge and transmembrane domains (AA 123-191, Ref sequence ID NP 001759.3), 4-1BB (CD137, AA 214-255, UniProt sequence ID Q07011) transactivation domain and CD3 zeta signaling domain (CD247, AA 52-163, Ref sequence ID: NP_000725.1.). Constructs 19A and 19B were identical, except for the flexible linker connecting the variable H and L chains of the scFv binding domain, employing the Whitlow linker in 19A [11] and a (GGGGS)$_3$ (SEQ ID NO: 13) linker in 19B. Tandem targeting constructs, CAR1920 and CAR2019, were generated in a similar manner. The scFv regions of 19A and 20A were linked in sequence by a flexible interchain linker (GGGGS)5 (SEQ ID NO: 14), followed by CD8, 4-1BB and CD3 zeta domains. Leader sequence from human granulocyte macrophage colony stimulating factor receptor alpha subunit was included in all constructs, as described in [12]. CAR constructs sequences were codon optimized (DNA2.0, Newark, CA) and cloned into a third generation lentiviral plasmid backbone (Lentigen Technology Inc., Gaithersburg, Md.) under the regulation of a human EF-1α promoter. Lentiviral vector (LV) containing supernatants were generated by transient transfection of HEK 293T cells, as previously described [13]. Harvested pelleted lentiviral supernatants were stored at −80° C.

Primary T Cell Transduction

Selected CD4+ and CD8+ human primary T cells from normal donors were cultivated in TexMACS medium (serum-free) supplemented with 40 IU/ml IL-2 at a density of 0.3 to 2×106 cells/ml, activated with CD3/CD28 MACS® GMP TransAct™ reagent (Miltenyi Biotec) and transduced on day 3 with lentiviral vectors encoding CAR constructs in the presence of 10 ug/ml protamine sulfate (Sigma-Aldrich, St. Louis, Mo.) overnight, and media exchanged on day 4. On day 5, cultures were transferred to TexMACS medium supplemented with 200 IU/ml IL-2, and propagated until harvest on day 10-13.

Immune Effector Assays (CTL and Cytokine)

To determine cell-mediated cytotoxicity (CTL assay), 5,000 target cells stably transduced with firefly luciferase were combined with CAR T cells at various effector to target ratios and incubated overnight. SteadyGlo reagent (Promega, Madison Wis.) was added to each well and the resulting luminescence was analyzed on an EnSpire plate reader (Perkin Elmer, Shelton, Conn.) and recorded as counts per second (sample CPS). Target only wells (max CPS) and target only wells plus 1% Tween-20 (min CPS) were used to determine assay range. Percent specific lysis was calculated as: (1-(sample CPS-min CPS)/(max CPS-min CPS)). For cytokine release assays, effector and target cells were combined at ratio 10:1 and incubated overnight. Harvested supernatants were analyzed for secreted cytokines using MACSplex human 12 cytokine bead array kit (Miltenyi Biotec) as per manufacturer's instructions. Strong induction of IFNγ, TNFα, IL-2 and GM-CSF were detected in CAR T-treated groups. The following cytokines could not be detected: IL-4, IL-5, IL-6, IL-12p70, IL-17A, IL-10, IFNα. IL-9 was detected in some samples at low levels and was not reported. All samples were in duplicate or triplicate. Unless otherwise noted, all data shown is representative of three or more independent experiments.

Western Blot

Two million CAR T cells were washed twice in cold PBS (Lonza, Walkersville, Md.), then lysed in 100 ul cold RIPA buffer (Sigma-Aldrich, St. Louis, Mo.) containing a protease and phosphatase inhibitor cocktail (Thermo-Fisher Scientific, Grand Island, N.Y.). The lysate was incubated at 4° C. for 20 minutes, pelleted at 13000 RPM in a table top centrifuge at 4° C. for 10 min, and supernatants collected and frozen at −20° C. Samples were denatured at 70° C. in reducing loading buffer (Invitrogen) for 10 minutes and resolved on 4%-12% gradient SDS-PAGE gel under reducing conditions in MOPS buffer (Thermo-Fisher Scientific, Grand Island, N.Y.) according to manufacturer's protocol. Proteins were transferred to 0.45 micron nitrocellulose transfer membrane (BioRad, Hercules, Calif.) and probed with antibody against pan-CD3 zeta (Clone ab40804, Abcam, Cambridge, Mass.). Bands were developed using Vectastain ABC-AMP reagent kit (Vector Laboratories, Burlingame, Calif.) according to manufacturer's protocol and bands were visualized and quantified on an Odyssey imaging system with Image Studio lite software (LI-COR, Lincoln, Nebr.).Western Blot for CD19 was also performed on Raji tumor cells. Briefly, after overnight incubation of Raji cells with CAR T cells, CD3-positive cells were depleted via LD columns using CD3 magnetic beads (Miltenyi Biotec) according to manufacturer's protocol, and the recovered Raji cells were processed as above. Specific bands were detected using antibodies directed to CD19 C-terminus (sc-69735, Santa Cruz, Calif.), and beta-actin (8457, Cell Signaling Technology, Danvers, Mass.). Band intensity was quantified by Image Studio software (LI-COR, Lincoln, Nebr.). Relative band intensity of full length CD19 and Δ exon 2 CD19 isoform was calculated as signal CD19/signal β actin.

Flow Cytometric Analysis

All cell staining reagents for flow cytometry were from Miltenyi Biotec, unless otherwise noted. One million CAR T transduced cells were harvested from culture, washed two times in cold staining buffer (AutoMACS solution with 0.5% bovine serum albumin) and pelleted at 350×g for 5 minutes at 4° C.

CAR surface expression on transduced T cells was detected by staining with protein L-biotin conjugate (stock 1 mg/ml, 1:1000 dilution, GenScript, Piscataway, N.J.) for 30 minutes at 4° C., followed by two washes and staining with streptavidin-PE conjugate for 30 minutes at 4° C. (stock: 1.0 ml, 1:200 dilution, Jackson ImmunoResearch Laboratories, West Grove, Pa.). Non-transduced cells and transduced cells stained with streptavidin-PE only, were used as negative controls. Anti-CD4 antibody was employed to determine CD4 to CD8 ratio of CAR T positive population, and was added during the second incubation step. Dead cells were excluded by 7AAD staining (BD Biosciences, San Jose, Calif.). Cells were washed twice and resuspended in 200 ul Staining Buffer before quantitative analysis by flow cytometry.

Specific CAR T staining was carried out with Fc-tagged-CD19 peptide (described below, at 1 μg/ml) by incubating with cells for 15 minutes at 4° C., followed by incubation with anti-Fc-AF647 F(ab')2 fragment at 4° C. for 15 minutes (Jackson Immuno Research, 1:200) and detected in the APC channel. Biotinylated CD20 peptide (Bachem, Torrance, Calif.) and strepatvidin PE (both at 1 μg/ml) were added to cells simultaneously and incubated at room temperature for 10 minutes in the dark. Flow cytometric analysis was performed on a MACSQuant® 10 Analyzer (Miltenyi Biotec). Characterization of target tumor lines and luciferase-positive sub clones was performed using CD19-FITC, CD20 VioBlue, and CD22-APC antibodies. Dead cells were excluded from analysis by 7AAD staining (BD Biosciences, San Jose, Calif.).

Generation of Fc-Tagged CD19 Peptide

For production of recombinant human CD19 peptide, the extracellular domain (amino acids 20-291, Uniprot P15391) was fused to human IgG1 Fc (CD19-Fc) and expressed by transduction in HEK293 cells in a CMV-driven mammalian expression vector. Transfected cells were cultured in DMEM, 5% FBS, and cell culture supernatant containing CD19-Fc harvested after ten and twenty days of incubation in HYPERFlask® cell culture vessels (Corning). After centrifugation to remove cell debris and 0.22 μm sterile filtration, CD19-Fc was purified by protein A chromatography (HiTrap MabSelect, GE Healthcare) and stored in PBS at 4° C. Purity was >97% as determined by SDS-PAGE and Coomassie Blue staining. Identity of CD19-Fc was confirmed by intact mass spectrometry and peptide mass fingerprint analyses after trypsin digestion (Miltenyi Biotec, Bergisch Gladbach, Germany).

In Vivo Analysis of CAR-T Activity

All animal studies were approved by Jackson Laboratory Animal Care and Use Committee (Sacramento, Calif.). A half million mouse-adapted Raji-luc cells were injected into the tail vein of NSG (NOD.Cg-Prkdcscid Il2rgtm1Wjl/SzJ) mice. On day 6 following Raji-luc injection, tumor engraftment was measured by i.p. injection of 150 mg/kg luciferin and imaging 10 min later for 40 seconds on a Xenogen IVIS-200 instrument (Caliper Biosciences, now Perkin Elmer, Shelton, Conn.). Images were analyzed using Living Image, version 4.1, software (Perkin Elmer) and the bioluminescent signal flux for each mouse was expressed as average radiance (photons per second per cm2 per steradian). CAR T cells were administered to mice via tail vein injection on Day 7. Imaging was performed on days 4, 6, 11, 14, 18, 25, 32, 46 following injection to establish the kinetics of tumor growth and eradication by CAR T cells.

For the high tumor burden in vivo study, NSG mice were injected i.v. with Raji-luciferase cells on Day 0. Mice were distributed equally to study groups on day 11 based on tumor burden. CAR T cell preparations of tandem-CAR 2019 or a combination two single CAR T preparations mixed at equal CART+ cell numbers (19A+20A, 19B+20A) were then administered i.v. on study day 12. All CAR T preparations were tested at 5×106 total CAR T cells/mouse. Non-transduced T cells from the same donor (N.T.) and Tumor alone group served as controls. On study days 18 and 25, tumor growth was assessed based on mouse whole body average radiance. N=6/group.

In Vitro Analysis of Leukemia Immune-Evasion

To analyze Raji tumor escape variants, CAR T and Raji cells were combined in vitro at an effector to target ratio of 1:1. For surviving Raji cells, surface expression of CD19, CD20 and C22 was determined by flow cytometry after overnight incubation and at day 4 of co-culture. Cultures were harvested, washed, and stained with antibodies specific for CD3-PE, CD19-FITC, CD20-VioBlue, CD22-APC (Miltenyi Biotec), and 7AAD. To facilitate the analysis of the surviving Raji cells in each Raji:T cell co-culture, we gated on the population of CD3-negative 7AAD-negative (i.e. live Raji) cells and this population was then analyzed for residual surface expression of CD19, CD20 and CD22.

In the transwell co-culture assay, 5×105 each of CAR T and Raji cells were seeded in the bottom compartment of a 24-transwell plate (Costar, REF 3470, 0.4 μM pore membrane), in 1 ml of TexMACS medium. 2.5×10$^5$ Raji cells were seeded in the upper transwell compartment in TexMACS medium in the absence of T cells. Following overnight incubation, cells from the upper and lower compartment were analyzed by flow cytometry as described above. Percentage expression of CD19, CD20 and CD22 on Raji cells for each group was measured. Data presented shows the average value+SD from three independent experiments, from three different donors. Statistical analysis was performed by one-way ANOVA followed by Dunnett's multiple comparisons test vs Raji alone control, *p<0.01."

Statistical Analysis

Statistical analysis was performed using GraphPad Prism 7.01 software. In in vitro killing assays, group means for replicate determinations were compared by two-way analysis of variance (ANOVA) followed by Dunnett's multiple comparisons test to identify differences between individual treatment groups and the non-transduced controls. In the first in vivo study, IVIS radiance data was analyzed on experimental day 25, the last measurement day when all groups had viable mice, by two-way ANOVA followed by Dunnett's multiple comparisons test vs no treatment group. Analysis of CD19, CD20 and CD22 expression in Raji and NALM-6 cells after overnight and 4 days of co-culture with CAR T cells was performed by one-way ANOVA followed by Dunnett's multiple comparisons test vs N.T. (non-transduced T cells from the same donor) control. Analysis of CD20/CD19 binding ratios in tandem-CARs was performed by student t-test.

Results

To study the effectiveness of tandem CD19 and CD20 targeting CARs, sequences encoding the antigen binding domains from the murine antibodies FMC63 and Leu16 were linked with a (GGGGS)5 (SEQ ID NO: 14) sequence. For all constructs in this study, the linking, transmembrane and signaling domains were identical, each encoding a human CD8-derived hinge and transmembrane domain, a CD137 signaling domain, and a CD3-zeta-derived signaling domain, as previously reported [12], FIG. 1A. The heavy and light chains of FMC63 were linked together into an scFv structure as originally published (GenBank ID HM852952.1, AA 130-148, known as the Whitlow linker) [11] while the heavy and light chains of Leu16 were linked by a (GGGGS)3 (SEQ ID NO: 13) sequence. Tandem-CARs were created by joining the FMC63-derived and Leu16-derived heavy and light chain sequences in a single transcript with a multiple-GGGGS (SEQ ID NO: 15) sequence as well. Unlike their single specificity counter-parts, the tandem-CARs can induce activation of the CAR-expressing T cells by encountering target cells that express either CD19 or CD20.

Primary human T cells were activated with anti-CD3/CD28 nanomatrix in 40 IU/ml IL-2 and transduced with lentiviral vectors encoding CARs 3 days later, followed by expansion in 200 IU/ml IL-2, which was maintained throughout the culture period. CAR expression was measured on the surface of transduced T cells by flow cytometry using biotinylated protein L, followed by staining with a Streptavidin-PE, FIG. 2A. Expression of CARs on the transduced T cell surface ranged from 61% to 93%. To verify that both scFv binding domains were intact we also co-incubated CAR T cells with a CD19-Fc fusion protein or with biotinylated CD20-peptide (see Methods). In tandem-specific constructs, both domains retained the ability to bind target antigen. For CAR2019, protein L staining gave 89% expression and CD19-Fc expression was 80%, and CD20-peptide expression was 85%. For CAR 1920, protein L staining gave 85% CAR expression, CD19-Fc staining yielded 80%, and CD20 peptide 68%. This observation was reproduced in CAR T cells generated from three separate donors.

To compare differences in antigen binding, the CAR T CD20/CD19 binding ratio was calculated. This ratio was defined as the percentage of the tandem-CAR T cells positively stained with the CD20 soluble peptide, divided by the percentage of CAR T cells positively stained by the CD19-Fc peptide in the same sample. The mean CD20/CD19 binding ratio for three separate donor T cell transductions was 0.74±0.06 for CAR1920, and 1.05±0.02 for CAR 2019 (FIG. 2B). Thus, whereas in CAR T construct 2019 the binding of the soluble CD19 and CD20 peptides is similar and comparable to the Protein L binding, the CD20 binding in the CAR 1920 construct may be partially sterically hindered.

To verify that the flow profiles were due to a single, larger, transcript, molecular weights of the CAR protein were verified by Western blot under reducing conditions (data not shown). Specific bands of the expected size were detected for the single (54 KDa)- and tandem (81 KDa) CARs. To ascertain relative expression levels, band intensities were compared by calculating the ratio of CAR associated zeta chain signal to endogenous CD3 zeta. Normalizing the CAR expression levels in the CAR 19B single chain vector to 1 (arbitrary unit), the expression for 19A, 20A, 1920, and 2019 were 1.8, 1.5, 0.9 and 1.2, respectively. Thus, the expression levels of tandem-CARs fall within the variability seen with single CAR expression vectors. Given the ability to create LV that express tandem-CARs, and now having demonstrated the expression of full-length CAR proteins on the T cell surface that express two functional scFv, the anti-leukemic activity of tandem-CAR constructs were then evaluated in in vitro assays.

Human primary T cells were transduced with LV encoding CAR constructs (19A, 19B, 20A, 1920, 2019, see Methods), then incubated for 18 hours with the Raji, NALM-6, REH, K562 or 293T cell lines, stably transduced with firefly luciferase, for luminescence based in vitro killing assays. All leukemia lines tested express CD19 on their surface, while the negative controls, K562 and 293T do not. CD20 expression varied between tumor lines. The Raji line is CD20 positive, while REH are CD20 negative, as are the control lines K562 and 293T. NALM-6 line has a weak but detectable expression of CD20. As additional controls, K562 lines were created that express CD19 (K562-19+), or CD20 (K562-20+).

K562-19+ were lysed by the CAR 19A and 19B constructs, tandem-CAR constructs 1920 and 2019, but not the single 20A CAR, FIG. 3A. K562-CD20+ were lysed by all CART constructs except for the single CAR19 constructs, demonstrating target antigen-restricted killing. Similar results were seen with the other leukemia cell lines tested. Single- and tandem-CAR T constructs targeting CD19 lysed Raji, NALM-6, and REH; but not 293T, FIG. 3B, or K562, FIG. 3A. Notably, the 20A single targeting CAR construct had no specific killing activity against the CD20-negative REH line, but did demonstrate killing of NALM-6, which has low but detectable levels of CD20 surface expression. In addition, the tandem-CAR 1920, which appeared to show lower binding to CD20 peptide than to CD19-Fc by flow cytometry, also has lower cytotoxicity against K562-19+ and K562-20+, but not against the CD19+CD20-REH. This may suggest that the 1920 tandem-CAR is inferior to 2019 tandem-CAR for some tumor targets.

The cytokine secretion by tumor-activated CAR T cells was then examined. Co-culture media supernatants were harvested following overnight incubation of CAR-T effectors and the Raji cell line at ratio of 10:1, and analyzed by MACSPlex cytokine-specific bead array which allows simultaneous detection of 12 different cytokines, FIG. 4. All CAR T constructs yielded increases in cytokine levels for IFN gamma, TNF alpha, IL-2 and GM-CSF when co-cultured with Raji cells, in comparison to non-transduced T cells, whereas cytokine levels in the negative control groups N.T. and GFP were undetectable. Notably, the 20A CAR was consistently the highest producer of IL-2, IFN gamma, TNF alpha, and GM-CSF. This was not due to a preferential expansion of the CD4+ T cell population, as the small changes seen, either up or down, in the CD4/CD8 ratio were not consistent, Supplementary Table 1 infra.

SUPPLEMENTARY TABLE 1

CD4/CD8 ratio of CART-transduced cell preparations.

| CAR T | Donor 1 CD4/CD8 | Donor 2 CD4/CD8 | Donor 3 CD4/CD8 |
| --- | --- | --- | --- |
| N.T. | 4.4 | 7.4 | 3.2 |
| GFP | 2.6 | 6.3 | 2.4 |
| 19A | 4.6 | 11.4 | 2.5 |
| 20A | 3.2 | 12.4 | 2.9 |
| 19B | 5.9 | 13.3 | 2.4 |
| 1920 | 5.2 | 6.2 | 2.2 |
| 2019 | 4.7 | 8.1 | 2.1 |

In respect of Supplementary Table 1, the CD4/CD8 ratio in CAR T cell preparations from three separate donors was determined by flow cytometry. The $CD4^+$ and $CD8^+$ T cells were co-purified from buffy coats, cells were activated with TransAct CD3 CD28 reagent in the presence of IL-2, transduced with LV as described in Materials and Methods, and assayed for CD4/CD8 composition on culture day 10, when immune function was assayed. The ratio of CD4/CD8 cells for each of the three donors is noted in columns, and CAR T groups noted in rows.

Both tandem constructs, CAR 1920 and CAR 2019, yielded strong induction of cytokines in the presence of tumor target that was similar in magnitude, and significant vs non-transduced controls. Cytokines IFN-α, IL-4, IL-5, IL-6, IL-9, IL-10, IL-12p70, IL-17A, also probed in MACSPlex cytokine array were not detected at significant levels in our samples.

To evaluate the in vivo activity of CAR-modified human T cells, $0.5 \times 10^6$ Raji-Luc cells were injected i.v. into NSG mice on day 0. The presence of engrafted leukemia was verified by imaging on day 6 and mice randomized into experimental groups. On day 7, $10 \times 10^6$ human T cells transduced with CAR constructs were injected i.v. and disease monitored by IVIS imaging. Representative images show the progression or regression of disease in each group, FIG. 5A. In animals dosed with 20A single CAR or tandem-CARs 1920 or 2019, tumor burden peaked on day 11, and by day 18 subsided to below pre-treatment level. Tumor elimination in single CAR19 groups was slower by comparison. Interestingly, CAR 19B, in which ScFv heavy and light chains were connected by a Gly-Ser linker, performed better than CAR 19A with a Whitlow linker, FIG. 5B. Overall, both CAR 1920 and CAR 2019 tandem-CAR constructs demonstrated in vivo activity superior of that of single CAR 19 in this model system. Moreover, this data highlights that cytotoxicity, cytokine production, and in vivo activity in an NSG mouse system are each important, but the data must be interpreted together in order to understand the biology of a transduced T cell population.

Figure 6A:
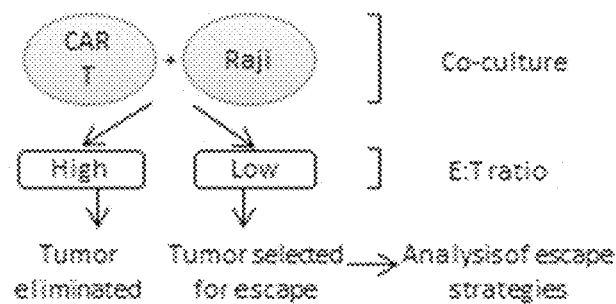
FIGS. 6A, 6B, and 6C depict a single CAR19 construct that strongly selects Raji tumor escape variants.
Figure 6B:
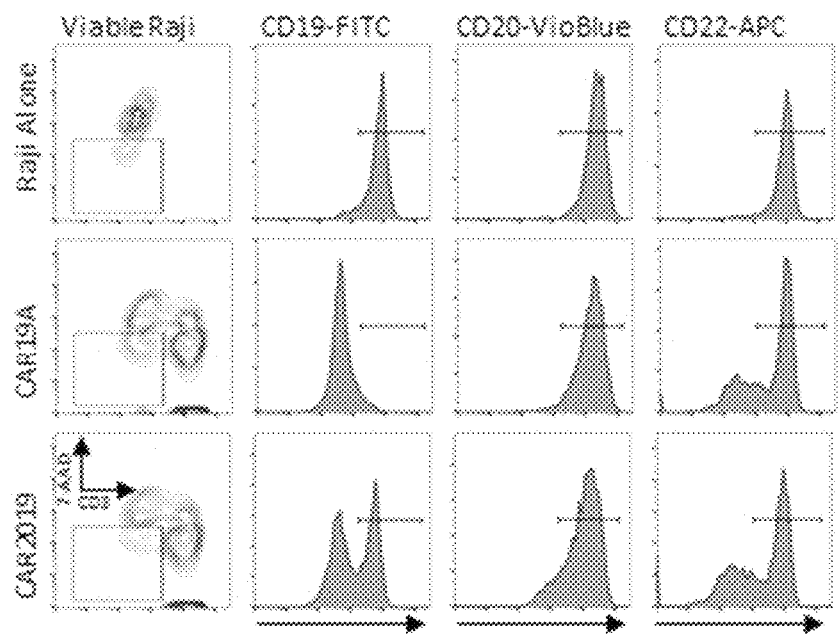
Figure 6C:
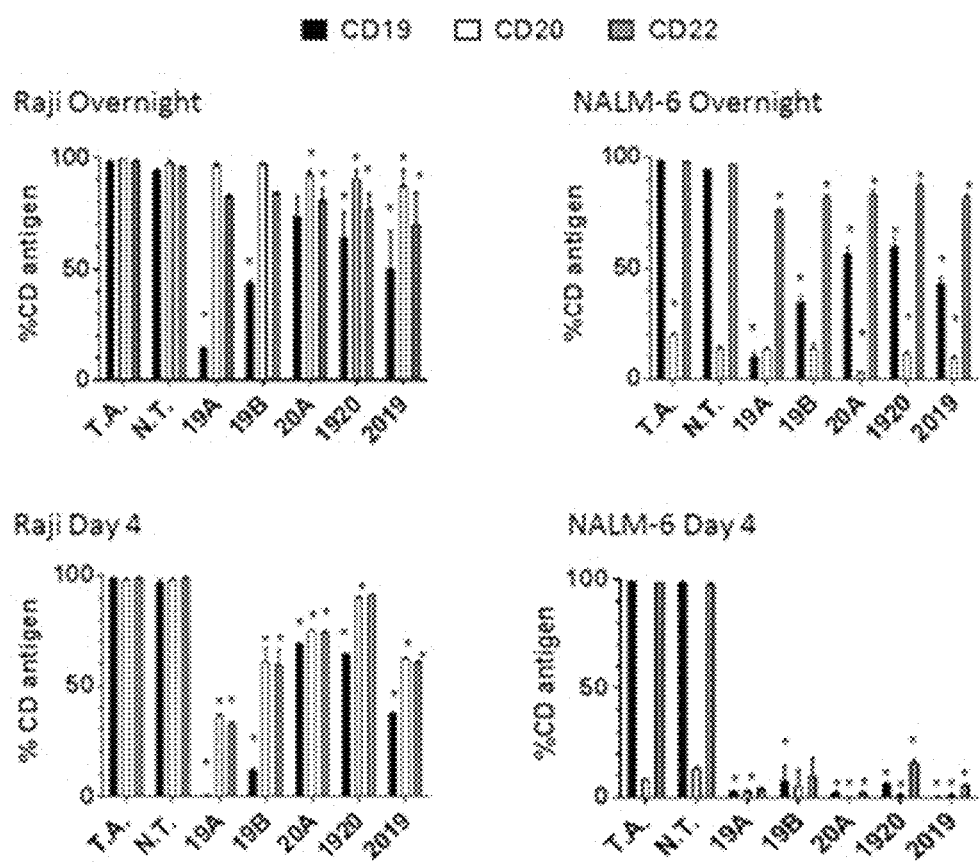

Having established a set of mono- and bi-specific CARs, their activities were exploited further. To explore the comparative efficacy of the tandem-CAR constructs in vitro, especially in light of recent descriptions of leukemia escape mechanisms, we used the Raji cell line (which expresses CD19, CD20, and CD22) and the NALM-6 cell line (which expresses CD19, CD22, and low levels of CD20) to explore the ability of leukemia cell lines to escape the strong effector activity of CAR-T, FIG. 6A. To model leukemia cell escape under CAR T immune pressure, CAR-T were co-incubated with leukemia cells at a low effector to target (E:T) ratio of 1:1. When the E:T was higher, all leukemia cells were eliminated. After short-term (overnight) or longer-term (four-day) co-culture, the expression of three B cell markers on the leukemia cell lines' surface were analyzed by flow cytometry (FIG. 6B, 6C). CD22 was of interest because it is not specifically targeted by our CAR-T cells and its loss may indicate the onset of a more general immune escape program, generating multiple antigen-loss variants.

When Raji was co-cultured with CAR19-T cells overnight, the CD19 antigen was rapidly down-modulated from the cell surface, FIG. 6B, 6C. CD20 was relatively constant, and in CD22 a minor population of antigen negative cells began to appear. When the tandem construct 2019 was co-cultured with Raji, CD19 was down-modulated, CD20 was also moderately down-modulated, and close to half of CD22 expression was also lost. When examined at day 4, all B cell antigens were greatly reduced, FIG. 6C. Targeting CD19 alone (constructs 19A and 19B) had the highest impact on CD19 expression. The tandem construct 2019, had a greater impact than the alternate 1920 construct, indicating that stronger immune pressure was mediated by 2019. Whether in short term or long-term co-culture, CD20 is less able to be lost from cells surviving immune pressure. In comparison to the single CD20-targeting construct 20A, the tandem construct 2019 generated more CD19 epitope loss, but appeared to exert similar combined pressure on the other targeted antigen, CD20, and the non-targeted antigen CD22.

When the NALM-6 leukemia cell line was used as a target, little impact was seen on CD20 expression except when the CD20-targeted CAR 20A was utilized (FIG. 6C). This again may reflect a greater resistance to altering CD20 expression on the surface of the leukemia cell line. In overnight co-cultures, CD19 expression was again highly plastic, with antigenic loss on the surviving cell population readily demonstrated. On day 4, few NALM-6 cells were available for study. This is likely due to the far greater sensitivity of NALM-6 to both indirect cytokine and direct cell-mediated killing effects. Notably, no CD22 positive-only cells were detected, indicating overall sensitivity of this line to immune effector mechanisms, i.e. non-selective cell loss.

Figure 4:
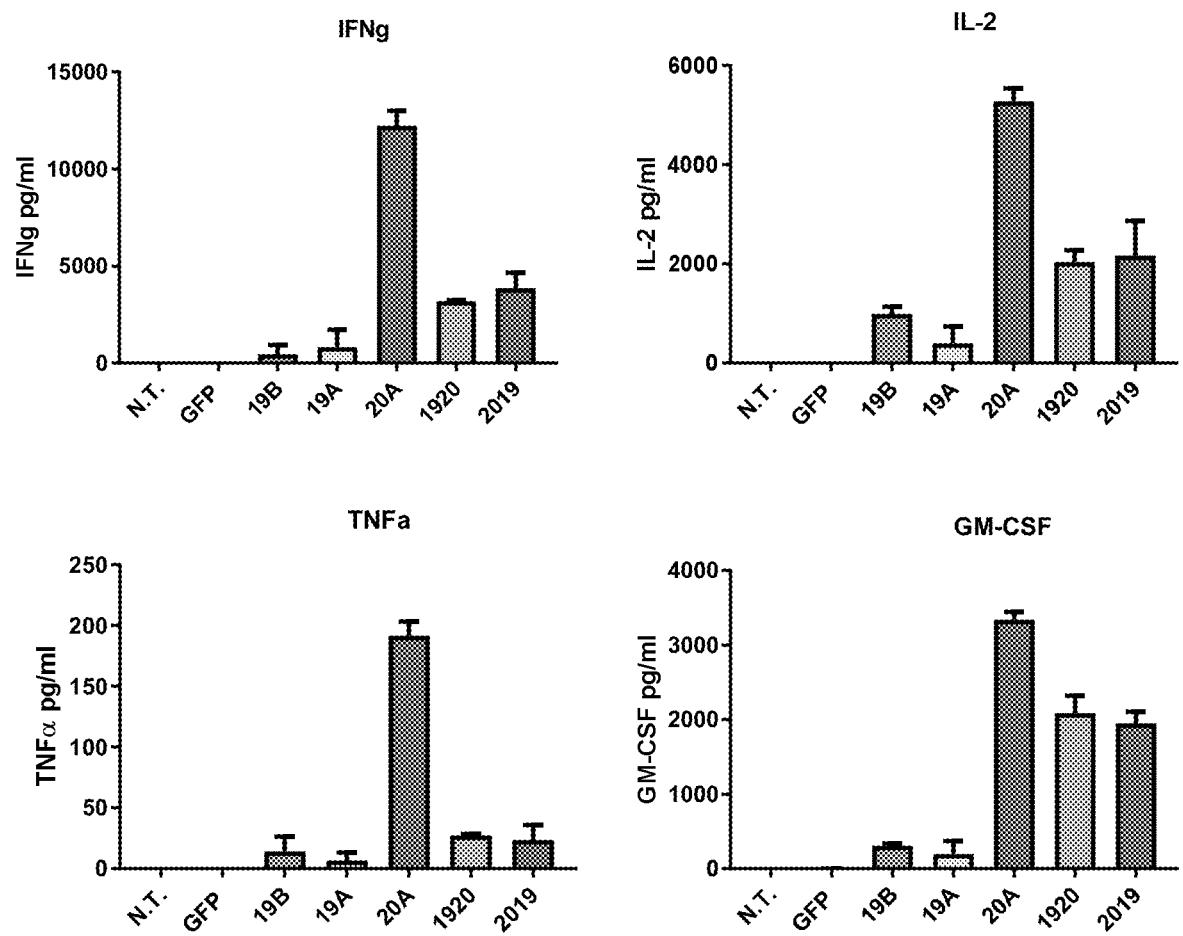
FIG. 4. CAR T cytokine release in response to leukemia cell lines. Cytokine production by CAR-T, listed on the x-axis, upon overnight co-culture with the Raji leukemia line at an E:T ratio of 10:1, was measured using a flow-based bead array. Bars represent mean +SD of replicate samples. Data are representative of three independent experiments performed with CAR T cells from three separate donors.

Modulation of the expression of tumor surface molecules by pro-inflammatory cytokines in chronic lymphocytic leukemia has been previously described [30]. Since CAR T cells elaborate high levels of pro-inflammatory cytokines when exposed to tumor cells, as shown in FIG. 4, it was sought to determine whether the down-modulation of CD19, CD22 or CD20 on Raji cells following co-incubation with CART cells is a direct effect of CAR T-tumor cell contact, or is due to soluble factors released to the medium by CAR T cells. Raji and CAR T cells were combined at the bottom of a transwell plate at an effector to target (E:T) ratio of 1:1. In the upper compartment, we placed Raji cells only. Following overnight incubation, cells from the transwell compartment as well as from the bottom of the well were harvested and analyzed by flow cytometry cell surface expression of CD19, CD20 and CD22 on viable Raji cells (FIG. 7). In agreement with our previous results, Raji cells co-incubated with CAR T cells demonstrated a dramatic reduction in CD19 surface expression by CARs 19A and 19B, and a more modest but significant reduction in CD20 and CD22. By contrast, Raji cells recovered from the upper transwell compartment, preserved full expression of CD19, CD20 and CD22 and were indistinguishable from the negative control groups: N.T., GFP and Raji alone. Therefore, the down-modulation of CD19 Raji expression by CAR T cells 19A and 19B is a direct effect of Tumor: CAR T contact.

Figure 8A:
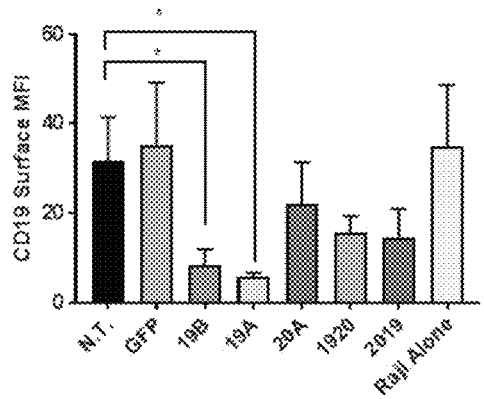
FIGS. 8A, 8B and 8C, below, depict the Down-modulation of CD19 full-length protein and CD19 splice variant by CAR19 constructs. Raji cells were co-incubated with CAR T cells at a 1:1 E:T ratio. After overnight incubation, T cells were removed from co-incubated cell populations using magnetic beads. CD19 expression on purified Raji populations was investigated by flow cytometry and Western blot.
Figure 8B:
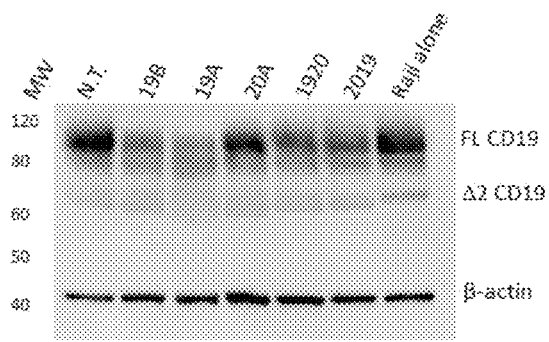

It has been recently reported that CD19—bearing tumors can evade elimination by CAR19 through preferential expression of a splice variant missing exon 2, which removes a portion of the CD19 extracellular domain that contains the binding epitope for FMC63 [8]. To explore CD19 plasticity on the Raji leukemia cell line, a co-culture experiment was carried out. Raji cells were co-cultured with CAR T overnight, then analyzed by flow cytometry to assay CD19 expression. A significant reduction in CD19 MFI was measured in both 19A and 19B experimental groups (FIG. 8A). Immunomagnetic beads were then use to deplete the co-culture, and the purified Raji cells were analyzed by Western blotting (FIG. 8B, C).

Figure 8C:
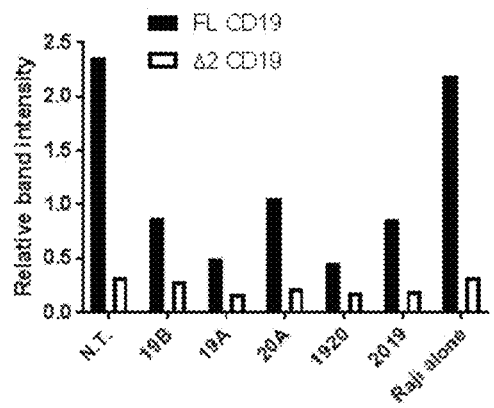

In order to evaluate whether splicing of exon 2 may have contributed to the diminished expression of full length CAR 19 protein, Western blot analysis was performed, as previously described [8]. The Raji cells expressed both full length and the 42 spliced CD19 isoforms in standard culture (Raji alone group), FIG. 8B. The intensity of Western blot bands was analyzed in order to quantify the relationship between the expression of full-length CD19 and its Δ2 splice variant (FIG. 8C). Decreased expression of the full-length CD19 isoform occurred in groups treated with CAR19 constructs 19A, and 19B, in agreement with our flow cytometry results.

Conversely, the expression of Δ2 spliced CD19 remained relatively stable regardless of CAR T treatment (FIG. 8C). When CAR T were removed from co-culture and purified Raji incubated alone, all treatment groups re-expressed the target antigens CD19, CD20, and CD22 at non-treated levels (98%—and above, not shown) by day 4. This demonstrates a very dynamic regulation of cell surface protein expression.

Figure 9A:
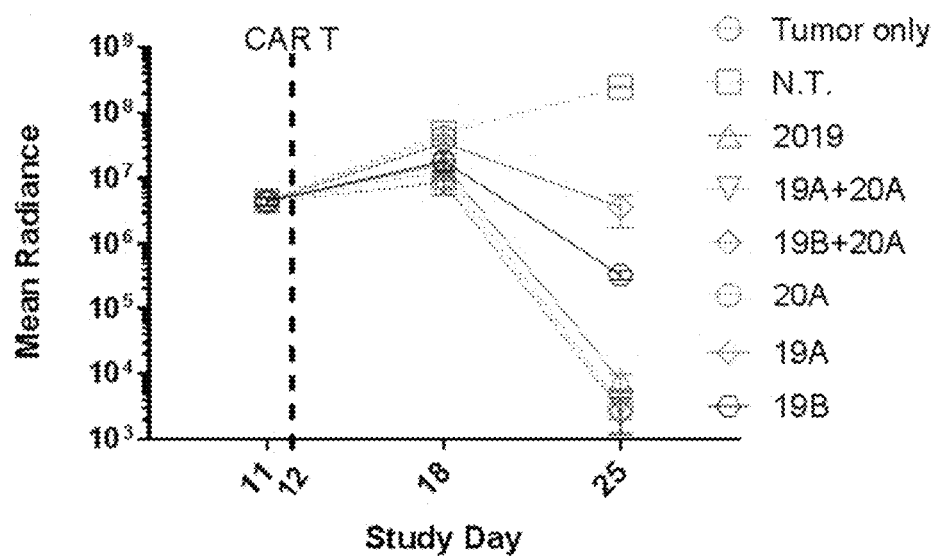
FIGS. 9A and 9B show the in vivo activity of CAR T cells in a high tumor burden model. NSG mice (n=6) were injected i.v. with Raji-luciferase cells on Day 0, and treated with CAR T cells, as indicated in the figure, on day 12.
Figure 9B:
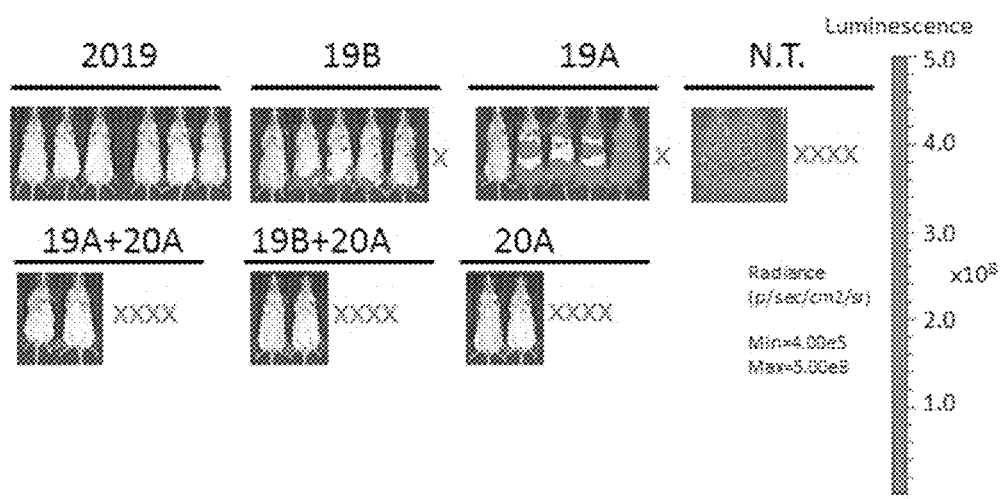
Figure 11A:
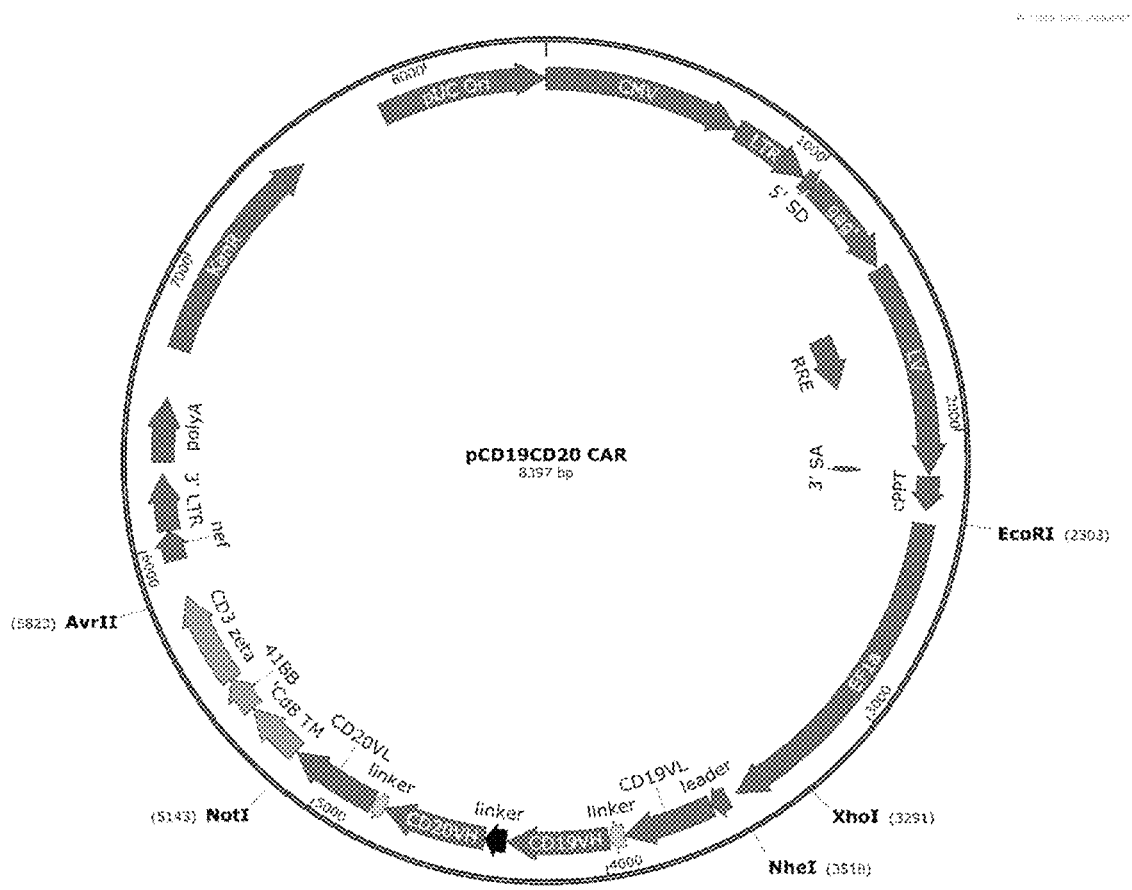
FIGS. 11A and 11B depict Plasmid Maps of the tandem CAR lentiviral vectors (LV) encoding the CD19_20 (FIG. 11A) and the CD20_19 (FIG. 11B) tandem CARs. The CD19_20 and CD20_19 tandem CARs were expressed using lentiviral backbone plasmids featuring a human EF-1alpha internal promoter (EF1a), leader sequence (leader), VH and VL sequence from FMC63 and Leu 16 antibodies (CD19VL, CD19VH, CD20 VL, CD20VH, respectively), inter-chain linker sequence, and intra-scFv sequence, linked to CD8, 41BB, and CD3zeta signaling domains.
Figure 11B:
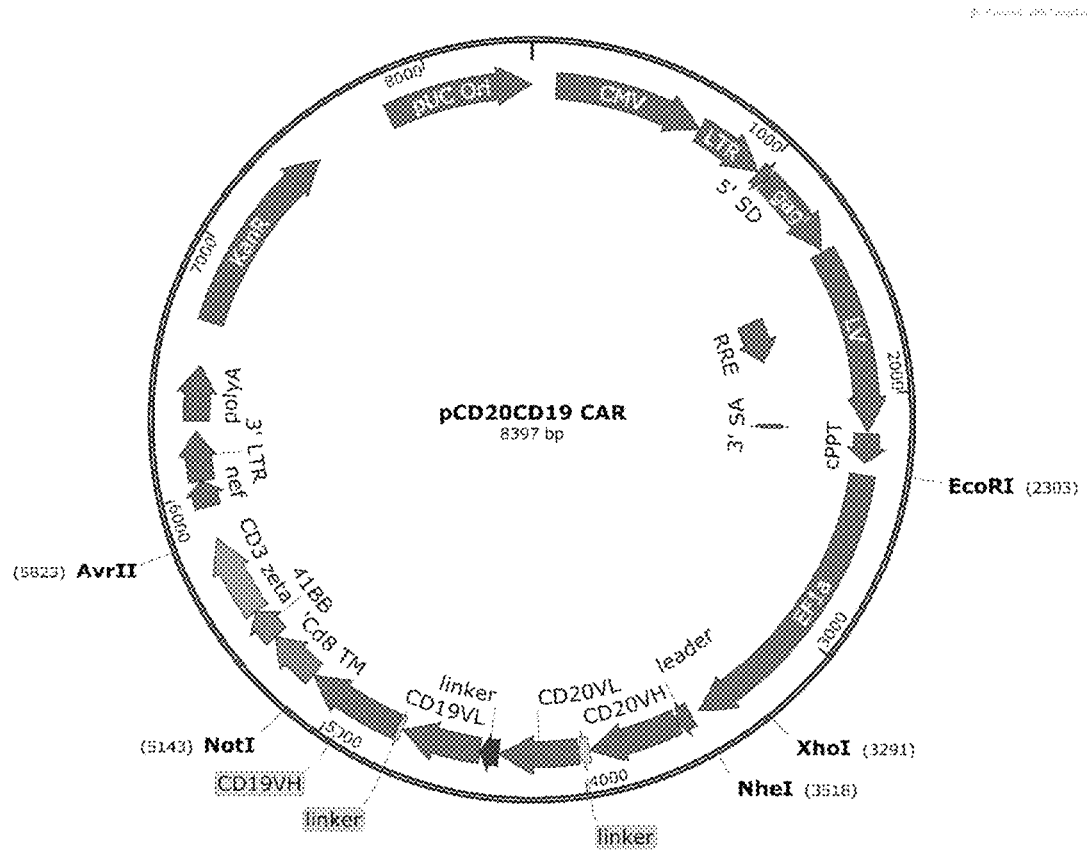

To further explore differences in tumor elimination between single and tandem-CARs, an additional study was performed in which Raji tumors were allowed to grow to day 12, as opposed to day 7, prior to CAR T administration, FIGS. 9A and 9B. Day 12 tumor-bearing mice received transduced T cell product with $5 \times 10^6$ CAR T+ cells per mouse for the single CARs, or the tandem 2019 CAR. Two T cell products were co-administered simultaneously, containing separate transductions of the CD19A+20A or the CD19B+20A CARs. A total of $2.5 \times 10^6$ CAR T cells were given for each construct (for a total of $5 \times 10^6$). The tandem-CAR2019 achieved strong reduction in tumor burden, in the absence of mortality, whereas the combination treatments 19A+20A and 19B+20A were effective but highly toxic, with only two out of six mice surviving to day 25 in each group. For the single CAR 19A and 19B groups, the tumor burden remained relatively high and only five out of six mice in each group survived to day 25. In the single 20A group, the tumors were cleared efficiently, but only two mice out of six survived. Surprisingly, the study highlighted the toxicity of CAR administration, which was greatest in the single 20A group or when 20A was combined with 19A or 19B CAR T cells.

Discussion

The linkage of anti-CD19 and anti-Her2 domains into a single tandem-CAR (termed a TanCAR by the authors) reduced to practice what many had proposed in theory, that the generation of a dual-specific chimeric antigen receptor (CAR) was possible [14]. In the drive to create improved CARs for the adoptive immunotherapy of hematologic malignancies, anti-CD19- and anti-CD20-based binding motifs were linked into a single transmembrane glycoprotein to create a set of tandem-CARs. These CAR constructs are capable of activation via binding of either CD19 or CD20 tumor molecules, as depicted in FIGS. 1A and 1B, and are effective both in vitro and in vivo against model leukemia cell lines. The standard animal model did not reveal a clear advantage or establish a preferred order of the CD19 and CD20 scFv within the CAR structure itself. Nevertheless, the 2019 CAR construct showed better binding of the CD20-peptide staining reagent by flow cytometry, and improved killing of some tumor cells lines in vitro, FIGS. 2A, 2B, 3A, and 3B. Furthermore, analysis of immune pressure in overnight and 4-day co-culture experiments indicated that the 2019 CAR may exert stronger immune pressure on the target leukemia cell lines, FIGS. 6A-6C and 8A-8C.

With regard to the polypeptide sequences of the CAR proteins, the effectiveness of linking both the VH and VL domains with a poly-glycine linker (GGGGS; SEQ ID NO: 15), as well as the linking of the two independent scFv in the tandem-CAR structures, was noted. This is important as the length of the VH and VL linking sequences, as well as their amino acid composition, have been shown to govern diabody formation and proper folding of the scFv domain [15]. Our data also support the findings of Zah et al., who were able to link the independent CD19 and CD20 scFv domains using the (GGGGS; SEQ ID NO: 15) sequence [16]. As demonstrated by Western blot analysis, the intensity of the native CD3-zeta chain bands indicates that the transcription or translation of TCR-associated transcripts like the zeta chain are not overwhelmed or displaced by CAR-transcription using an EF-1-alpha driven CAR payload in a LV system (FIG. 3 of Schneider et al. Journal for Immuno-Therapy of Cancer (2017) 5:42 is incorporate herein by reference in its entirety).

Figure 2A:
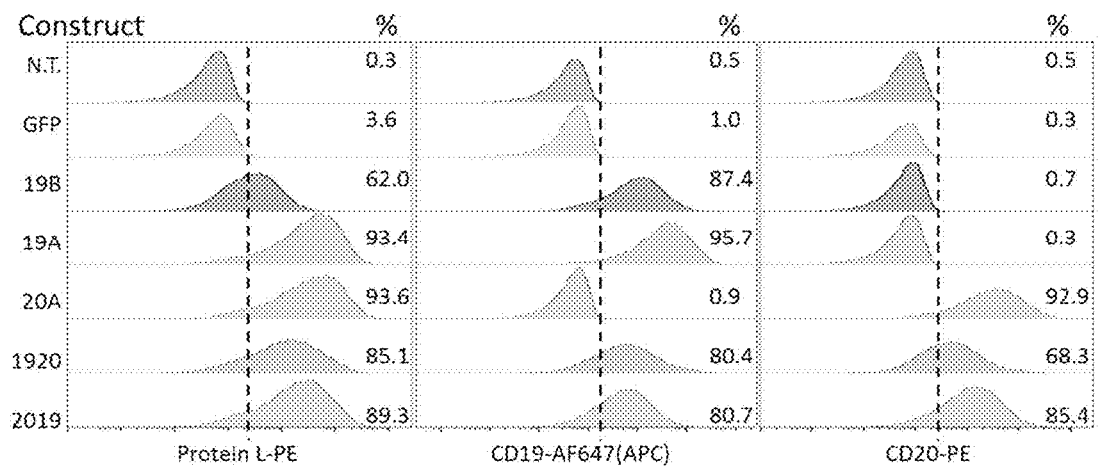
FIG. 2A: Surface expression of single and tandem-CAR T constructs on human primary T cells. CAR T expression was determined by flow cytometry. T cells were activated with Miltenyi Biotec TransAct™ CD3 CD28 reagent in the presence of IL-2, and transduced with LV as described in Materials and Methods. On culture day 10, viable transduced T cells (7-AAD negative) were assayed for CAR surface expression using one of three staining reagents: Protein L (column 1), CD19 Fc followed by anti-Fc-AF647 (column 2), or CD20-biotin followed by streptavidin-PE staining (column 3). The LV used in transduction is listed to the left of each row. Percentage of CAR T-positive populations in relation to non-transduced T cell control is noted in the right-hand corner of each histogram. GFP-transduced cells served as an additional negative control. Representative data of three separate donors is shown.
Figure 2B:
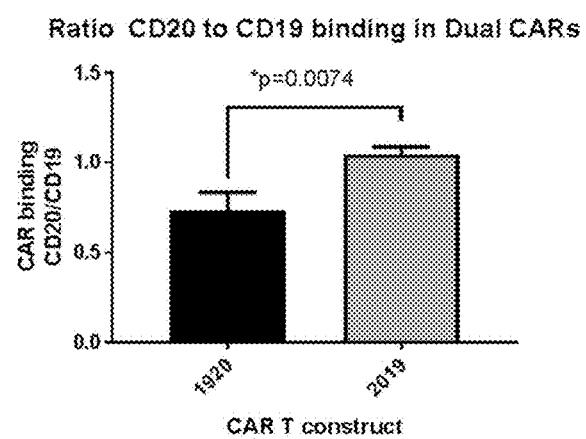
FIG. 2B: The ratio of CD19 and CD20 antigen binding by each tandem-CAR is expressed as the ratio of percent cells bound by CD20 biotin vs CD19 Fc. The average+SD of 3 separate experiments using three donors is shown, **p<0.01.

Demonstration of the ability to bind target protein by the scFv encoded by the CAR and tandem-CAR vectors was achieved using a set of unique tools generated by the expression of recombinant fragments of CD19 and CD20, FIGS. 2A and 2B. Previous reports have used Protein L, which binds kappa light chain sequences, to stain for cell surface CAR expression [12]. For both FMC63-based scFv CARs specific for CD19 (constructs 19A, 19B), protein L bound well, although the original Whitlow linker had a brighter MFI. This held true for staining with the recombinant CD19 fragment as well, but the difference was less pronounced. Protein L and recombinant CD20 peptide gave very similar results for the Leu16-based anti-CD20 CAR (construct 20A). In the tandem-CARs, Protein L staining was equivalently strong. The anti-CD19 scFv binding of target peptide was essentially equivalent in tandem and single CARs, but signal for CD20-biotin-based staining was diminished in construct 1920, in comparison to 2019 (FIG. 2B), which may indicate steric hindrance for binding to CD20 in this construct. In the CD20 negative leukemia cell lines, we saw a somewhat lower level of lysis with the CAR 1920 as opposed to the CAR 2019 tandem vector. One possible explanation for this functional disparity is that in tandem-CARs the CD19 binder has to be placed close to T cell membrane to match the distance of the CD19 epitope from the tumor cell surface. This notion is supported by the example of ROR1 CARs, where the length of extracellular spacer was decisive in determining the CAR tumor recognition [17]. Interestingly, CD19 binder placement proximal to T cell membrane was also required for optimal function of another tandem-CAR currently in development, the CD22_CD19 CAR (W. Haso, unpublished observations). It is hypothesized that better antigen binding by the 2019 CAR may reflect that the CD20 binder requires the carboxy terminus to be untethered for the proper VH to VL folding or that in the 1920 construct the CD20 binding site is obscured by the adjacent linker-CD19 domains.

In vitro cytokine release activity also demonstrated tandem-CAR activity, FIG. 4. However, the CD20-specific CAR 20A was superior to tandem and single CD19 CAR constructs in the production of Th-1 like cytokines: IFN-gamma, IL-2, and TNF-alpha, and GM-CSF. Both tandem-CARs were similar in cytokine production and were greater than the single 19A and 19B constructs. The level of cytokine produced by the tandem-CAR constructs 1920 and 2019 may be primarily driven by CD20 recognition, and reflect another tandem-CAR advantage, namely that optimal features from each binder were preserved for better potential therapeutic effect.

Figure 5A:
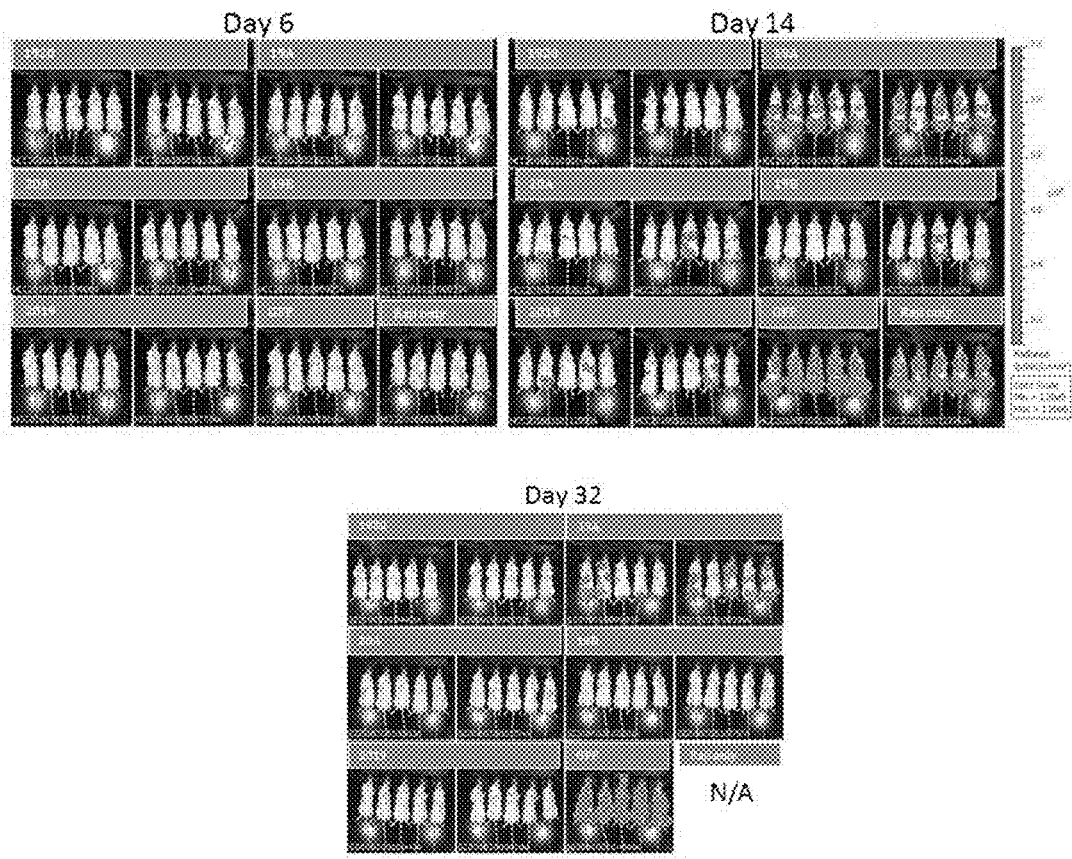
FIGS. 5A and 5B depict the in vivo activity of CAR T constructs.
Figure 5B:
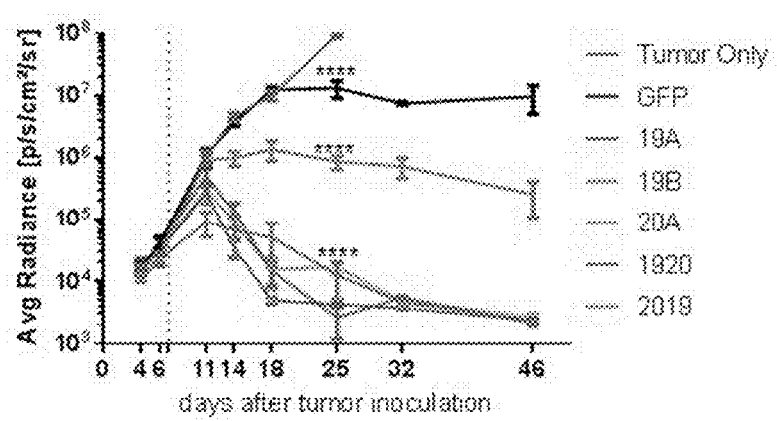

In vivo CAR 19B performed better than CAR 19A, FIGS. 5A and 5B. This may be due in part to the superior ability of 19B to produce IL-2 and thus sustain T cell activity in the NSG mouse model, which we did not supplement with the addition of human cytokines. Taken together these data indicate that cytokine production is important in predicting the in vivo activity of anti-leukemia CARs in the NSG mouse system.

The ability of CAR-mediated immune pressure to modulate leukemia phenotypes was then tested. To this end, it was found that although effector to target ratios of 5:1 and above effectively eliminated leukemia cells in CTL assays, when the lower effector to target ratio of 1:1 was used, we could still harvest the surviving leukemia cells and analyze their surface antigen expression. Flow cytometry allowed the operator to gate for viable cells, exclude T cells, and quantify antigen expression, FIG. 6A, 6B. After overnight incubation with the 19A and 19B CARs, strong down-modulation of CD19 was seen. The tandem-CARs induced less antigenic loss, but there were far fewer cell remaining. CD20 expression was modulated less. Interestingly, some CD22-down-modulation was also detected. This may indicate that both antigen-specific and non-antigen-specific mechanisms of escape are possible in the Raji cell population analyzed. Both overnight and four-day CAR co-incubations were then carried out with the Raji and NALM-6 cell lines, FIG. 6C. The analysis of NALM-6 was limited by the more general sensitivity of NALM-6 to activated lymphocytes. Even at the low 1:1 E:T ratio, few NALM-6 leukemia cells from the co-cultures were available for analysis on day 4. After overnight incubation, strong down-modulation of CD19 expression was seen, with CAR 19A and 19B LV-transduced T cells having the greatest effect. The tandem-CARs and surprisingly the 20A CD20 CAR all had a measurable effect on CD19, (FIG. 6C). Also of note, CD22 expression decreased by 15-20%, indicating that non-targeted B cell differentiation antigens are impacted as well. Using the Raji cell line, it was easier to observe the effects of CAR-mediated immune pressure on CD20. In CAR-T co-culture experiments, CD20 was less variable with respect to loss of surface antigen expression than the non-targeted antigen CD22. As with NALM-6, CD19 down-modulation was rapid and occurred in the vast majority of cells. After 4 days of immune pressure in Raji cells, the tandem-CARs 2019 and 1920 appeared to maintain immune pressure as all three B cell antigens were moderately down-modulated. CD19 expression remained strongly down-modulated, especially with the CD19 single specificity vectors. The 20A CAR immune pressure, both overnight and at day 4, showed a lesser ability to select for escape mutants, indicating perhaps a lesser ability for Raji cells to dispense with or alter its expression.

Down-modulation of tumor antigen surface expression by soluble cytokines produced by inflammatory cells has been documented in chronic lymphocytic leukemia [30]. It was then investigated whether the soluble factors present in the medium of co-cultured CAR T and tumor cells are responsible for the down modulation of CD19, CD20 and CD22 on Raji cells in a transwell co-culture assay. We found that direct contact between Raji tumor cells and CAR T cells was necessary to down-modulate Raji surface expression of CD19, CD20 and CD22.

In order to probe the mechanism of CD19 loss with regard to antibody staining by flow cytometry, the findings of the Thomas-Tikhonenko lab were used to investigate the prevalence of CD19 isoforms in Raji cells exposed to CAR T [8]. To that end, Raji cells were co-cultured with CAR-T, then analyzed them by flow cytometry at the end of overnight incubation to demonstrate reduction in CD19 expression. Subsequently, we used immunomagnetic beads to deplete the co-culture of T cells. The separated Raji cells were analyzed by Western blotting. Surprisingly, it was found that the reduction in the full-length CD19 isoform was mainly responsible for the observed decrease in CD19 staining, and the levels of Δ2 CD19 isoform remained relatively stable regardless of treatment.

Given that the variation in B cell surface antigen expression was so profound, we wanted to investigate its relative permanence. In other words, was this a true mutational effect, or was it a phenotypic accommodation? To address this question, the CAR T-separated Raji cells were returned to culture, and then analyzed by flow cytometry again on day 4. All tumor populations demonstrated full recovery, with CD19, CD20, and CD22 expression being greater than 98%.

Tumor antigen escape is one of the major challenges facing the field of adoptive cell therapy today. Despite significant progress achieved in the treatment of relapsed or refractory ALL using CAR19, tumor escape by downregulating the CD19 epitope on tumor cells has been reported [5, 18, 19], and is responsible for a significant portion of disease relapse. It has become clear that combinatorial approaches will be necessary to overcome tumor escape in hematologic malignancies, especially in disease types that are more challenging to treat than pediatric pre-B-ALL, such as NHL, reviewed in [20]. Furthermore, as evidenced for CAR19 treatment of leukemia and as was also shown in an in vivo model of PSCA and MUC1-positive tumors [21], heterogeneous target antigen expression may lead to tumor escape variants when a single CAR T therapy is used. Therefore, targeting multiple tumor antigens with a single CAR T therapeutic product may mitigate tumor antigen escape.

Sotillo and co-workers [8], demonstrated that CD19 loss occurs in primary disease as well as leukemia and lymphoma cell lines under CAR19 pressure by a variety of mechanisms, including both mutations and expansion of CD19-negative variants, as well as alternative splicing that yields the exon 2-deficient CD19 variant. Recent studies have shown that after prolonged CAR-T immune pressure on CD19 antigens, tumors may also escape detection by reverting to a CD19-negative myeloid phenotype [22, 23]. In the experimental model employed, CD19 downregulation on Raji leukemia in the presence of CD19 CAR constructs 19A and 19B was rapid, with a significant loss of detected CD19 expression occurring after just an overnight co-culture with CAR T. The loss of CD19 expression was restored completely within 4 days after the CAR T cells were removed from culture. Given the rapidity of the change being measured, and considering that Raji cells replicate approximately once every 20 hours, CD19 downregulation by an actual CD19 loss mutation and the preferential expansion of CD19-negative lymphoma clones in our model is unlikely. Furthermore, it was determined that in the presence of the single CAR19 constructs 19A and 19B, the amount of full length CD19 protein in Raji whole cell lysates is reduced, in concordance with the diminished CD19 staining as probed by flow cytometry, whereas the amount of exon 2 spliced CD19 remains relatively stable regardless of the type of CAR T used. Therefore, the alternative splicing of CD19 exon 2 is not modified by CAR-mediated downregulation of full-length CD19.

CD19 is a B cell co-receptor, and it acts a positive regulator of maturation, proliferation and survival in early and late B cell development [24, 25]. CD19 is internalized together with the B cell receptor following its engagement by ligand. Similarly, CD19 can be internalized following binding by specific antibody, a fact that is being exploited in antibody-conjugate (ADC) therapy. Internalization of CD20 from the surface of B cells is also known to occur following the use of the therapeutic antibody rituximab [26]. One could speculate that CAR19 pressure would cause CD19 internalization as well. However, in our system the mere internalization of CD19 could not explain the fact that the level of full-length CD19 protein is diminished following 19A and 19B treatment, as shown by Western blot. Thus, CD19 protein downregulation must occur at the transcriptional or translational level, or by increased degradation of the CD19 protein upon CAR-driven internalization. This effect is very dynamic, and is reversed soon after the CAR19 pressure in removed.

The significance of the reduction in CD19 expression by exposure to CAR T therapy for tumor growth remains to be fully elucidated. Mechanistically speaking, CD19 reduces B cell activation thresholds by promoting B cell receptor-antigen micro cluster formation, and initiating several downstream signaling pathways [27]. CD19 is typically thought of as a promoter of lymphomagenesis, and has been shown to drive B cell proliferation via a positive feedback loop with MYC oncoprotein [28, 29]. However, CD19 is downregulated on some types of B cell leukemias, including CLL, B-PLL, SLVL, and MCL [9]. It is therefore possible that in some instances, such as when selective pressure is applied by CD19-targeted CART cells, CD19 loss may confer a tumor growth advantage. The plasticity of CD19 evidenced in leukemic cells may be a characteristic preserved from normal B cell biology, now providing an additional survival advantage to the malignancy.

Finally, the activity of tandem-CARs versus single CARs was tested in a more advanced disease setting, with a higher tumor burden. A simplified approach was also compared where two CAR products, each expressing a single CD19- or CD20-CAR were combined into one effector population, FIGS. 9A and 9B. The CD2019 CAR was the only treatment group that was able to control the tumor in which all the subjects survived to study day 25. The single CARs 19A and 19B on their own did not have as strong an anti-disease effect and one mouse was lost from each group. The 20A CAR on its own or in combination with either CD19 CAR did apparently clear mice of disease, but four of the six mice did not survive to day 25. This may be due to the greater probably of the tandem 2019 CAR to be activated by the tumor cell, and its more moderate cytokine production profile as compared to the 20A CAR, FIG. 4. In this study we could not differentiate between deaths due to advanced disease or CAR related toxicity. However, it is suspected that 20A CAR-related toxicity may have played a role, because of the complete clearance of disease from the surviving mice. Although alloreactivity may play a role in all of our studies, since we are using model tumor cell lines, the lack of activity of GFP or N.T. controls in any of the assays employed, demonstrates that it is not a major effect.

Conclusions

The studies described herein on their own do not prove that CAR T immune pressure generates durable escape mutants, but clinical experience to date has shown that CD19 negative relapse is not a rare event [8, 18, 19]. Moreover, the data demonstrate that CD19 antigen modulation is a very rapid event, and that the targeting two antigens at the same time may be a reasonable approach to address this issue. The high tumor burden study highlights an interesting new biology that could be attributed to the tandem-CAR T product and may indicate a superior CAR design format for translational studies. Alternatively, in this study, a unique balance has been struck between effective in vitro activity, notably cytokine production and killing activity, that needs to be ascertained for optimal in vivo activity by considering both the CAR expressed by the effector cell and the overall disease burden.

Abbreviations

AA—amino acids, 7AAD—seven-actinomycin D, AF—alexa fluor, ALL—acute lymphoblastic leukemia, ANOVA—analysis of variance, APC—allophycocyanin, CAR T—chimeric antigen receptor T cells, CD—cluster of differentiation, CLL—chronic lymphocytic leukemia, CPS— counts per second, CTL—cytotoxic T lymphocyte, ELISA—enzyme linked immunosorbent assay, FBS—fetal bovine serum, Fc—fragment crystallizable region, FITC—fluorescein isothiocyanate, GFP—reen fluorescent protein, GM-CSF—granulocyte macrophage colony stimulating factor, GMP— good manufacturing practice, HCL—hairy cell leukemia, HEK—human embryonic kidney cells, Her2—human epidermal growth factor receptor two, IFNγ—interferon gamma, IL-2—interleukin two, IU international units, LV—lentiviral vector, Luc—firefly luciferase, MCL—mantle cell lymphoma, MOPS—three-(N-morpholino)propanesulfonic acid, NSG—NOD.Cg-Prkdcscid Il2rgtm1Wjl/SzJ, N.T.—non-transduced T cells control from same donor, OBI—Oklahoma Blood Institute, PE—Phycoerythrin, PLL—prolymphocytic leukemia, ROR1—Receptor tyrosine kinase-like orphan receptor 1, RPM—revolutions per minute, scFv—single chain variable fragment, SDS-PAGE— sodium dodecyl sulfate polyacrylamide gel electrophoresis, SLVL—splenic lymphoma with villous lymphocytes, T.A.—tumor alone control group, TNFα—tumor necrosis factor alpha, VH—variable heavy chain domain, VL—variable light chain domain.

References for Example 1

1. Lee, D. W., et al., The future is now: chimeric antigen receptors as new targeted therapies for childhood cancer. Clinical Cancer Research, 2012. 18(10): p. 2780-2790.
2. Kochenderfer, J. N., et al., Construction and pre-clinical evaluation of an anti-CD19 chimeric antigen receptor. Journal of immunotherapy (Hagerstown, Md.: 1997), 2009. 32(7): p. 689.
3. Jensen, M., et al., CD20 is a molecular target for scFvFc: zeta receptor redirected T cells: implications for cellular immunotherapy of CD20+ malignancy. Biology of Blood and Marrow Transplantation, 1998. 4(2): p. 75-83.
4. Lee, D. W., et al., T cells expressing CD19 chimeric antigen receptors for acute lymphoblastic leukaemia in children and young adults: a phase 1 dose-escalation trial. The Lancet, 2015. 385(9967): p. 517-528.
5. Grupp, S. A., et al., Chimeric antigen receptor-modified T cells for acute lymphoid leukemia. New England Journal of Medicine, 2013. 368(16): p. 1509-1518.
6. Porter, D. L., et al., Chimeric antigen receptor-modified T cells in chronic lymphoid leukemia. New England Journal of Medicine, 2011. 365(8): p. 725-733.
7. Kochenderfer, J. N., et al., B-cell depletion and remissions of malignancy along with cytokine-associated toxicity in a clinical trial of anti-CD19 chimeric-antigen-receptor-transduced T cells. Blood, 2012. 119(12): p. 2709-2720.
8. Sotillo, E., et al., Convergence of acquired mutations and alternative splicing of CD19 enables resistance to CART-19 immunotherapy. Cancer discovery, 2015. 5(12): p. 1282-1295.

9. Ginaldi, L., et al., Levels of expression of CD19 and CD20 in chronic B cell leukaemias. Journal of clinical pathology, 1998. 51(5): p. 364-369.
10. Barrett, D. M., et al., Noninvasive bioluminescent imaging of primary patient acute lymphoblastic leukemia: a strategy for preclinical modeling. Blood, 2011. 118(15): p. e112-e117.
11. Whitlow, M., et al., An improved linker for single-chain Fv with reduced aggregation and enhanced proteolytic stability. Protein engineering, 1993. 6(8): p. 989-995.
12. Haso, W., et al., Anti-CD22-chimeric antigen receptors targeting B-cell precursor acute lymphoblastic leukemia. Blood, 2013. 121(7): p. 1165-1174.
13. Kuroda, H., et al., Simplified lentivirus vector production in protein-free media using polyethylenimine-mediated transfection. Journal of virological methods, 2009. 157(2): p. 113-121.
14. Grada, Z., et al., TanCAR: a novel bispecific chimeric antigen receptor for cancer immunotherapy. Molecular Therapy-Nucleic Acids, 2013. 2(7): p. e105.
15. Wu, A.M., et al., Multimerization of a chimeric anti-CD20 single-chain Fv-Fc fusion protein is mediated through variable domain exchange. Protein engineering, 2001. 14(12): p. 1025-1033.
16. Zah, E., et al., T cells expressing CD19/CD20 bi-specific chimeric antigen receptors prevent antigen escape by malignant B cells. Cancer immunology research, 2016.
17. Hudecek, M., et al., Receptor affinity and extracellular domain modifications affect tumor recognition by ROR1-specific chimeric antigen receptor T cells. Clinical cancer research, 2013. 19(12): p. 3153-3164.
18. Grupp, S. A., et al., Durable remissions in children with relapsed/refractory aLL treated with T cells engineered with a CD19-targeted chimeric antigen receptor (CTL019). Blood, 2015. 126(23): p. 681-681.
19. Ruella, M., et al., Dual CD19 and CD123 targeting prevents antigen-loss relapses after CD19-directed immunotherapies. The Journal of Clinical Investigation, 2016. 126(10).
20. Onea, A. S. and A. R. Jazirehi, CD19 chimeric antigen receptor (CD19 CAR)-redirected adoptive T-cell immunotherapy for the treatment of relapsed or refractory B-cell Non-Hodgkin's Lymphomas. American journal of cancer research, 2016. 6(2): p. 403.
21. Usanarat Anurathapan, R. C. C., Hakeem F Hindi, Roopa Mucharla, Pradip Bajgain, Brendan C Hayes, William E Fisher, Helen E Heslop, Cliona M Rooney, Malcolm K Brenner, Ann M Leen, and Juan F Vera. Kinetics of Tumor Destruction by Chimeric Antigen Receptor-modified T Cells. . Molecular Therapy, 2014. 22(3): p. 623-633.
22. Jacoby, E., et al., CD19 CAR immune pressure induces B-precursor acute lymphoblastic leukaemia lineage switch exposing inherent leukaemic plasticity. Nature Communications, 2016. 7.
23. Gardner, R., et al., Acquisition of a CD19-negative myeloid phenotype allows immune escape of MLL-rearranged B-ALL from CD19 CAR-T-cell therapy. Blood, 2016. 127(20): p. 2406-2410.
24. Otero, D. C. and R. C. Rickert, CD19 function in early and late B cell development. II. CD19 facilitates the pro-B/pre-B transition. The Journal of Immunology, 2003. 171(11): p. 5921-5930.
25. Otero, D. C., A. N. Anzelon, and R. C. Rickert, CD19 function in early and late B cell development: I. Maintenance of follicular and marginal zone B cells requires CD19-dependent survival signals. The Journal of Immunology, 2003. 170(1): p. 73-83.
26. Beers, S. A., et al., Antigenic modulation limits the efficacy of anti-CD20 antibodies: implications for antibody selection. Blood, 2010. 115(25): p. 5191-5201.
27. Depoil, D., et al., CD19 is essential for B cell activation by promoting B cell receptor-antigen microcluster formation in response to membrane-bound ligand. Nature immunology, 2008. 9(1): p. 63-72.
28. Chung, E. Y., et al., CD19 is a major B cell receptor-independent activator of MYC-driven B-lymphomagenesis. The Journal of clinical investigation, 2012. 122(6): p. 2257-2266.
29. Poe, J. C., et al., A c-Myc and surface CD19 signaling amplification loop promotes B cell lymphoma development and progression in mice. The Journal of Immunology, 2012. 189(5): p. 2318-2325.
30. Vilpo J, et al., Surface membrane antigen expression changes induced in vitro by exogenous growth factors in chronic lymphocytic leukemia cells. Leukemia, 2002 (16), 1691-1698.

EQUIVALENTS

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein. Those skilled in the art will recognize, or be able to ascertain using no more than routine experimentation, many equivalents to the embodiments of the invention described herein. Such equivalents are encompassed by the following claims.

Sequences of the Disclosure

The nucleic and amino acid sequences listed below are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 nucleotide sequence of Leader-CD19 VL-Whitlow linker CD19 VH
(GGGGS)-5 CD20 VH (GGGGS)-3 CD20 VL CD8 hinge + TM-4-1BB-CD3z (Construct CAR
1920)
ATGCTCCTTCTCGTGACCTCCCTGCTTCTCTGCGAACTGCCCCATCCTGCCTTC
CTGCTG
ATTCCCGACATTCAGATGACTCAGACCACCTCCTCCCTGTCCGCCTCCCTGGG
CGACCGC
GTGACCATCTCATGCCGCGCCAGCCAGGACATCTCGAAGTACCTCAACTGGT
ACCAGCAG
AAGCCCGACGGAACCGTGAAGCTCCTGATCTACCACACCTCCCGGCTGCACA
GCGGAGTG
CCGTCTAGATTCTCGGGTTCGGGGTCGGGAACTGACTACTCCCTTACTATTTC
CAACCTG
GAGCAGGAGGATATTGCCACCTACTTCTGCCAACAAGGAAACACCCTGCCGT
ACACTTTT
GGCGGGGGAACCAAGCTGGAAATCACTGGCAGCACATCCGGTTCCGGGAAG
CCCGGCTCC
GGAGAGGGCAGCACCAAGGGGGAAGTCAAGCTGCAGGAATCAGGACCTGGC
CTGGTGGCC
CCGAGCCAGTCACTGTCCGTGACTTGTACTGTGTCCGGAGTGTCGCTCCCGGA
TTACGGA
GTGTCCTGGATCAGGCAGCCACCTCGGAAAGGATTGGAATGGCTCGGAGTCA
TCTGGGGT
TCCGAAACCACCTATTACAACTCGGCACTGAAATCCAGGCTCACCATTATCA
AGGATAAC
TCCAAGTCACAAGTGTTCCTGAAGATGAATAGCCTGCAGACTGACGACACGG
CGATCTAC
TATTGCGCCAAGCACTACTACTACGGCGGATCCTACGCTATGGACTACTGGG
GCCAGGGG
ACCAGCGTGACCGTGTCATCCGGAGGCGGCGGCAGCGGCGGGGAGGGTCC
GGAGGGGGT
GGTTCTGGTGGAGGAGGATCGGGAGGCGGTGGCAGCGAGGTGCAGTTGCAA
CAGTCAGGA
GCTGAACTGGTCAAGCCAGGAGCCAGCGTGAAGATGAGCTGCAAGGCCTCC
GGTTACACC
TTCACCTCCTACAACATGCACTGGGTGAAACAGACCCCGGGACAAGGGCTCG
AATGGATT
GGCGCCATCTACCCCGGGAATGGCGATACTTCGTACAACCAGAAGTTCAAGG
GAAAGGCC
ACCCTGACCGCCGACAAGAGCTCCTCCACCGCGTATATGCAGTTGAGCTCCC
TGACCTCC
GAGGACTCCGCCGACTACTACTGCGCACGGTCCAACTACTATGGAAGCTCGT
ACTGGTTC
TTCGATGTCTGGGGGGCCGGCACCACTGTGACCGTCAGCTCCGGGGGCGGAG
GATCCGGT
GGAGGCGGAAGCGGGGGTGGAGGATCCGACATTGTGCTGACTCAGTCCCCGG
CAATCCTG
TCGGCCTCACCGGGCGAAAAGGTCACGATGACTTGTAGAGCGTCGTCCAGCG
TGAACTAC
ATGGATTGGTACCAAAAGAAGCCTGGATCGTCACCCAAGCCTTGGATCTACG
CTACATCT
AACCTGGCCTCCGGCGTGCCAGCGCGGTTCAGCGGGTCCGGCTCGGGCACCT
CATACTCG
CTGACCATCTCCCGCGTGGAGGCTGAGGACGCCGCGACCTACTACTGCCAGC
AGTGGTCC
TTCAACCCGCCGACTTTTGGAGGCGGTACTAAGCTGGAGATCAAAGCGGCCG
CAACTACC
ACCCCTGCCCCTCGGCCGCCGACTCCGGCCCCAACCATCGCAAGCCAACCCC
TCTCCTTG
CGCCCCGAAGCTTGCCGCCCGGCCGCGGGTGGAGCCGTGCATACCCGGGGGC
TGGACTTT
GCCTGCGATATCTACATTTGGGCCCCGCTGGCCGGCACTTGCGGCGTGCTCCT
GCTGTCG
CTGGTCATCACCCTTTACTGCAAGAGGGGCCGGAAGAAGCTGCTTTACATCTT
CAAGCAG
CCGTTCATGCGGCCCGTGCAGACGACTCAGGAAGAGGACGGATGCTCGTGCA
GATTCCCT
GAGGAGGAAGAGGGGGGATGCGAACTGCGCGTCAAGTTCTCACGGTCCGCC
GACGCCCCC
GCATATCAACAGGGCCAGAATCAGCTCTACAACGAGCTGAACCTGGGAAGG
AGAGAGGAG
TACGACGTGCTGGACAAGCGACGCGGACGCGACCCGGAGATGGGGGGAAA
CCACGGCGG
AAAAACCCTCAGGAAGGACTGTACAACGAACTCCAGAAAGACAAGATGGCG
GAAGCCTAC
TCAGAAATCGGGATGAAGGGAGAGCGGAGGAGGGGAAAGGGTCACGACGG
GCTGTACCAG
GGACTGAGCACCGCCACTAAGGATACCTACGATGCCTTGCATATGCAAGCAC
TCCCACCC
CGG -continued SEQ ID NO: 2 amino acid sequence of Leader-CD19 VL-Whitlow linker CD19 VH
(GGGGS)-5 CD20 VH (GGGGS)-3 CD20 VL CD8 hinge + TM-4-1BB-CD3z (Construct CAR
1920)
MLLLVTSLLLCELPHPAFLLIPDIQMTQTTSSLSASLGDRVTISCRASQDISKYLNWYQ
QKPDGTVKLLIYHTSRLHSGVPSRFSGSGSGTDYSLTISNLEQEDIATYFCQQGNTLPYTFGG
GTKLEITGSTSGSGKPGSGEGSTKGEVKLQESGPGLVAPSQSLSVTCTVSGVSLPDYGVSWIR
QPPRKGLEWLGVIWGSETTYYNSALKSRLTIIKDNSKSQVFLKMNSLQTDDTAIYYCAKHYY
YGGSYAMDYWGQGTSVTVSSGGGGSGGGGSGGGGSGGGGSGGGGSEVQLQQSGAELVKP
GASVKMSCKASGYTFTSYNMHWVKQTPGQGLEWIGAIYPGNGDTSYNQKFKGKATLTADK
SSSTAYMQLSSLTSEDSADYYCARSNYYGSSYWFFDVWGAGTTVTVSSGGGGSGGGGSGG
GGSDIVLTQSPAILSASPGEKVTMTCRASSSVNYMDWYQKKPGSSPKPWIYATSNLASGVPA
RFSGSGSGTSYSLTISRVEAEDAATYYCQQWSFNPPTFGGGTKLEIKAAATTTPAPRPPTPAPT
IASQPLSLRPEACRPAAGGAVHTRGLDFACDIYIWAPLAGTCGVLLLSLVITLYCKRGRKKLL
YIFKQPFMRPVQTTQEEDGCSCRFPEEEEGGCELRVKFSRSADAPAYQQGQNQLYNELNLGR
REEYDVLDKRRGRDPEMGGKPRRKNPQEGLYNELQKDKMAEAYSEIGMKGERRRGKGHD
GLYQGLSTATKDTYDALHMQALPPR SEQ ID NO: 3 nucleotide sequence of Leader-CD20 VH (GGGGS)3-CD20 VL-
(GGGGS)5-CD19 VL-Whitlow linker-CD19 VH CD8 hinge + TM-4-1BB-CD3z
(Construct 2019)
ATGCTCCTTCTCGTGACCTCCCTGCTTCTCTGCGAACTGCCCCATCCTGCCTTC
CTGCTG
ATTCCCGAGGTGCAGTTGCAACAGTCAGGAGCTGAACTGGTCAAGCCAGGAG
CCAGCGTG
AAGATGAGCTGCAAGGCCTCCGGTTACACCTTCACCTCCTACAACATGCACT
GGGTGAAA
CAGACCCCGGGACAAGGGCTCGAATGGATTGGCGCCATCTACCCCGGGAATG
GCGATACT
TCGTACAACCAGAAGTTCAAGGGAAAGGCCACCCTGACCGCCGACAAGAGC
TCCTCCACC
GCGTATATGCAGTTGAGCTCCCTGACCTCCGAGGACTCCGCCGACTACTACTG
CGCACGG
TCCAACTACTATGGAAGCTCGTACTGGTTCTTCGATGTCTGGGGGGCCGGCAC
CACTGTG
ACCGTCAGCTCCGGGGGCGGAGGATCCGGTGGAGGCGGAAGCGGGGGTGGA
GGATCCGAC
ATTGTGCTGACTCAGTCCCCGGCAATCCTGTCGGCCTCACCGGGCGAAAAGG
TCACGATG
ACTTGTAGAGCGTCGTCCAGCGTGAACTACATGGATTGGTACCAAAAGAAGC
CTGGATCG
TCACCCAAGCCTTGGATCTACGCTACATCTAACCTGGCCTCCGGCGTGCCAGC
GCGGTTC
AGCGGGTCCGGCTCGGGCACCTCATACTCGCTGACCATCTCCCGCGTGGAGG
CTGAGGAC
GCCGCGACCTACTACTGCCAGCAGTGGTCCTTCAACCCGCCGACTTTTGGAG
GCGGTACT
AAGCTGGAGATCAAAGGAGGCGGCGGCAGCGGCGGGGAGGGTCCGGAGGG
GGTGGTTCT
GGTGGAGGAGGATCGGGAGGCGGTGGCAGCGACATTCAGATGACTCAGACC
ACCTCCTCC
CTGTCCGCCTCCCTGGGCGACCGCGTGACCATCTCATGCCGCGCCAGCCAGG
ACATCTCG
AAGTACCTCAACTGGTACCAGCAGAAGCCCGACGGAACCGTGAAGCTCCTGA
TCTACCAC
ACCTCCCGGCTGCACAGCGGAGTGCCGTCTAGATTCTCGGGTTCGGGGTCGG
GAACTGAC
TACTCCCTTACTATTTCCAACCTGGAGCAGGAGGATATTGCCACCTACTTCTG
CCAACAA
GGAAACACCCTGCCGTACACTTTTGGCGGGGGAACCAAGCTGGAAATCACTG
GCAGCACA
TCCGGTTCCGGGAAGCCCGGCTCCGGAGAGGGCAGCACCAAGGGGGAAGTC
AAGCTGCAG
GAATCAGGACCTGGCCTGGTGGCCCCGAGCCAGTCACTGTCCGTGACTTGTA
CTGTGTCC
GGAGTGTCGCTCCCGGATTACGGAGTGTCCTGGATCAGGCAGCCACCTCGGA
AAGGATTG
GAATGGCTCGGAGTCATCTGGGGTTCCGAAACCACCTATTACAACTCGGCAC
TGAAATCC
AGGCTCACCATTATCAAGGATAACTCCAAGTCACAAGTGTTCCTGAAGATGA
ATAGCCTG
CAGACTGACGACACGGCGATCTACTATTGCGCCAAGCACTACTACTACGGCG
GATCCTAC
GCTATGGACTACTGGGGCCAGGGGACCAGCGTGACCGTGTCATCCGCGGCCG
CAACTACC
ACCCCTGCCCCTCGGCCGCCGACTCCGGCCCCAACCATCGCAAGCCAACCCC
TCTCCTTG
CGCCCCGAAGCTTGCCGCCCGGCCGCGGGTGGAGCCGTGCATACCCGGGGC
TGGACTTT

```
GCCTGCGATATCTACATTTGGGCCCCGCTGGCCGGCACTTGCGGCGTGCTCCT
GCTGTCG
CTGGTCATCACCCTTTACTGCAAGAGGGGCCGGAAGAAGCTGCTTTACATCTT
CAAGCAG
CCGTTCATGCGGCCCGTGCAGACGACTCAGGAAGAGGACGGATGCTCGTGCA
GATTCCCT
GAGGAGGAAGAGGGGGGATGCGAACTGCGCGTCAAGTTCTCACGGTCCGCC
GACGCCCCC
GCATATCAACAGGGCCAGAATCAGCTCTACAACGAGCTGAACCTGGGAAGG
AGAGAGGAG
TACGACGTGCTGGACAAGCGACGCGGACGCGACCCGGAGATGGGGGGGAAA
CCACGGCGG
AAAAACCCTCAGGAAGGACTGTACAACGAACTCCAGAAAGACAAGATGGCG
GAAGCCTAC
TCAGAAATCGGGATGAAGGGAGAGCGGAGGAGGGGAAAGGGTCACGACGG
GCTGTACCAG
GGACTGAGCACCGCCACTAAGGATACCTACGATGCCTTGCATATGCAAGCAC
TCCCACCC
CGG

SEQ ID NO: 4 Leader-CD20 VH (GGGGS)3-CD20 VL-(GGGGS)5-CD19 VL-
Whitlow linker-CD19 VH CD8 hinge + TM-4-1BB-CD3z amino acid sequence
(Construct CAR 2019)
MLLLVTSLLLCELPHPAFLLIPEVQLQQSGAELVKPGASVKMSCKASGYTFTSYN
MHWVKQTPGQGLEWIGAIYPGNGDTSYNQKFKGKATLTADKSSSTAYMQLSSL
TSEDSADYYCARSNYYGSSYWFFDVWGAGTTVTVSSGGGGSGGGGSGGGGSDI
VLTQSPAILSASPGEKVTMTCRASSSVNYMDWYQKKPGSSPKPWIYATSNLASG
VPARFSGSGSGTSYSLTISRVEAEDAATYYCQQWSFNPPTFGGGTKLEIKGGGGS
GGGGSGGGGSGGGGSGGGGSDIQMTQTTSSLSASLGDRVTISCRASQDISKYLN
WYQQKPDGTVKLLIYHTSRLHSGVPSRFSGSGSGTDYSLTISNLEQEDIATYFCQ
QGNTLPYTFGGGTKLEITGSTSGSGKPGSGEGSTKGEVKLQESGPGLVAPSQSLS
VTCTVSGVSLPDYGVSWIRQPPRKGLEWLGVIWGSETTYYNSALKSRLTIIKDNS
KSQVFLKMNSLQTDDTAIYYCAKHYYYGGSYAMDYWGQGTSVTVSSAAATTT
PAPRPPTPAPTIASQPLSLRPEACRPAAGGAVHTRGLDFACDIYIWAPLAGTCGVL
LLSLVITLYCKRGRKKLLYIFKQPFMRPVQTTQEEDGCSCRFPEEEEGGCELRVKF
SRSADAPAYQQGQNQLYNELNLGRREEYDVLDKRRGRDPEMGGKPRRKNPQE
GLYNELQKDKMAEAYSEIGMKGERRRGKGHDGLYQGLSTATKDTYDALHMQA
LPPR SEQ ID NO: 5 nucleotide sequence of CD19 LTG1494 (CAR 19A)
ATGGTCATGCTTCTCCTGGTCACCTCCCTGCTCCTCTGCGAACTGCCTCACCCT
GCCTTC
CTTCTGATTCCTGACACTGACATTCAGATGACTCAGACCACCTCTTCCTTGTC
CGCGTCA
CTGGGAGACAGAGTGACCATCTCGTGTCGCGCAAGCCAGGATATCTCCAAGT
ACCTGAAC
TGGTACCAACAGAAGCCCGACGGGACTGTGAAGCTGCTGATCTACCACACCT
CACGCCTG
CACAGCGGAGTGCCAAGCAGATTCTCCGGCTCCGGCTCGGGAACCGATTACT
CGCTTACC
ATTAGCAACCTCGAGCAGGAGGACATCGCTACCTACTTCTGCCAGCAAGGAA
ATACCCTG
CCCTACACCTTCGGCGGAGGAACCAAATTGGAAATCACCGGCTCCACGAGCG
GCTCCGGG
AAGCCTGGTTCCGGGGAAGGCTCCACTAAGGGTGAAGTGAAGCTCCAGGAGT
CCGGCCCC
GGCCTGGTGGCGCCGTCGCAATCACTCTCTGTGACCTGTACCGTGTCGGGAGT
GTCCCTG
CCTGATTACGGCGTGAGCTGGATTCGGCAGCCGCCGCGGAAGGGCCTGGAAT
GGCTGGGT
GTCATCTGGGGATCCGAGACTACCTACTACAACTCGGCCCTGAAGTCCCGCC
TGACTATC
ATCAAAGACAACTCGAAGTCCCAGGTCTTTCTGAAGATGAACTCCCTGCAAA
CTGACGAC
ACCGCCATCTATTACTGTGCTAAGCACTACTACTACGGTGGAAGCTATGCTAT
GGACTAC
TGGGGCCAGGGGACATCCGTGACAGTCAGCTCCGCGGCCGCAACTACCACCC
CTGCCCCT
CGGCCGCCGACTCCGGCCCCAACCATCGCAAGCCAACCCCTCTCCTTGCGCC
CCGAAGCT
TGCCGCCCGGCCGCGGGTGGAGCCGTGCATACCCGGGGGCTGGACTTTGCCT
GCGATATC
TACATTTGGGCCCCGCTGGCCGGCACTTGCGGCGTGCTCCTGCTGTCGCTGGT
CATCACC
CTTTACTGCAAGAGGGGCCGGAAGAAGCTGCTTTACATCTTCAAGCAGCCGT
TCATGCGG
CCCGTGCAGACGACTCAGGAAGAGGACGGATGCTCGTGCAGATTCCCTGAGG
AGGAAGAG
```

```
GGGGGATGCGAACTGCGCGTCAAGTTCTCACGGTCCGCCGACGCCCCCGCAT
ATCAACAG
GGCCAGAATCAGCTCTACAACGAGCTGAACCTGGGAAGGAGAGAGGAGTAC
GACGTGCTG
GACAAGCGACGCGGACGCGACCCGGAGATGGGGGGGAAACCACGGCGGAA
AAACCCTCAG
GAAGGACTGTACAACGAACTCCAGAAAGACAAGATGGCGGAAGCCTACTCA
GAAATCGGG
ATGAAGGGAGAGCGGAGGAGGGGAAAGGGTCACGACGGGCTGTACCAGGGA
CTGAGCACC
GCCACTAAGGATACCTACGATGCCTTGCATATGCAAGCACTCCCACCCCGG

SEQ ID NO: 6 amino acid sequence of CD19 LTG1494 (CAR 19A) protein
MVMLLLVTSLLLCELPHPAFLLIPDTDIQMTQTTSSLSASLGDRVTISCRASQDISK
YLN
WYQQKPDGTVKLLIYHTSRLHSGVPSRFSGSGSGTDYSLTISNLEQEDIATYFCQ
QGNTL
PYTFGGGTKLEITGSTSGSGKPGSGEGSTKGEVKLQESGPGLVAPSQSLSVTCTVS
GVSL
PDYGVSWIRQPPRKGLEWLGVIWGSETTYYNSALKSRLTIIKDNSKSQVFLKMNS
LQTDD
TAIYYCAKHYYYGGSYAMDYWGQGTSVTVSSAAATTTPAPRPPTPAPTIASQPL
SLRPEA
CRPAAGGAVHTRGLDFACDIYIWAPLAGTCGVLLLSLVITLYCKRGRKKLLYIFK
QPFMR
PVQTTQEEDGCSCRFPEEEEGGCELRVKFSRSADAPAYQQGQNQLYNELNLGRR
EEYDVL
DKRRGRDPEMGGKPRRKNPQEGLYNELQKDKMAEAYSEIGMKGERRGKGHDG
LYQGLST
ATKDTYDALHMQALPPR SEQ ID NO: 7 nucleotide sequence of CD19 LTG1538 (CAR 19B) DNA
ATGCTTCTCCTGGTCACCTCCCTGCTCCTCTGCGAACTGCCTCACCCTGCCTTC
CTTCTG
ATTCCTGACATTCAGATGACTCAGACCACCTCTTCCTTGTCCGCGTCACTGGG
AGACAGA
GTGACCATCTCGTGTCGCGCAAGCCAGGATATCTCCAAGTACCTGAACTGGT
ACCAACAG
AAGCCCGACGGGACTGTGAAGCTGCTGATCTACCACACCTCACGCCTGCACA
GCGGAGTG
CCAAGCAGATTCTCCGGCTCCGGCTCGGGAACCGATTACTCGCTTACCATTAG
CAACCTC
GAGCAGGAGGACATCGCTACCTACTTCTGCCAGCAAGGAAATACCCTGCCCT
ACACCTTC
GGCGGAGGAACCAAATTGGAAATCACCGGCGGAGGAGGCTCCGGGGAGGA
GGTTCCGGG
GGCGGGGGTTCCGAAGTGAAGCTCCAGGAGTCCGGCCCCGGCCTGGTGGCGC
CGTCGCAA
TCACTCTCTGTGACCTGTACCGTGTCGGGAGTGTCCCTGCCTGATTACGGCGT
GAGCTGG
ATTCGGCAGCCGCCGCGGAAGGGCCTGGAATGGCTGGGTGTCATCTGGGGAT
CCGAGACT
ACCTACTACAACTCGGCCCTGAAGTCCCGCCTGACTATCATCAAAGACAACT
CGAAGTCC
CAGGTCTTTCTGAAGATGAACTCCCTGCAAACTGACGACACCGCCATCTATTA
CTGTGCT
AAGCACTACTACTACGGTGGAAGCTATGCTATGGACTACTGGGGCAAGGCA
CTTCGGTG
ACTGTGTCAAGCGCGGCCGCAACTACCACCCCTGCCCCTCGGCCGCCGACTC
CGGCCCCA
ACCATCGCAAGCCAACCCCTCTCCTTGCGCCCCGAAGCTTGCCGCCCGGCCG
CGGGTGGA
GCCGTGCATACCCGGGGGCTGGACTTTGCCTGCGATATCTACATTTGGGCCCC
GCTGGCC
GGCACTTGCGGCGTGCTCCTGCTGTCGCTGGTCATCACCCTTTACTGCAAGAG
GGGCCGG
AAGAAGCTGCTTTACATCTTCAAGCAGCCGTTCATGCGGCCCGTGCAGACGA
CTCAGGAA
GAGGACGGATGCTCGTGCAGATTCCCTGAGGAGGAAGAGGGGGGATGCGAA
CTGCGCGTC
AAGTTCTCACGGTCCGCCGACGCCCCCGCATATCAACAGGGCCAGAATCAGC
TCTACAAC
GAGCTGAACCTGGGAAGGAGAGAGGAGTACGACGTGCTGGACAAGCGACGC
GGACGCGAC
CCGGAGATGGGGGGGAAACCACGGCGGAAAAACCCTCAGGAAGGACTGTAC
AACGAACTC
CAGAAAGACAAGATGGCGGAAGCCTACTCAGAAATCGGGATGAAGGGAGAG
CGGAGGAGG
```

```
GGAAAGGGTCACGACGGGCTGTACCAGGGACTGAGCACCGCCACTAAGGAT
ACCTACGAT
GCCTTGCATATGCAAGCACTCCCACCCCGG

SEQ ID NO: 8 amino acid sequence of CD19 LTG1538 (CAR 19B)
MLLLVTSLLLCELPHPAFLLIPDIQMTQTTSSLSASLGDRVTISCRASQDISKYLNW
YQQ
KPDGTVKLLIYHTSRLHSGVPSRFSGSGSGTDYSLTISNLEQEDIATYFCQQGNTL
PYTF
GGGTKLEITGGGGSGGGGSGGGGSEVKLQESGPGLVAPSQSLSVTCTVSGVSLPD
YGVSW
IRQPPRKGLEWLGVIWGSETTYYNSALKSRLTIIKDNSKSQVFLKMNSLQTDDTAI
YYCA
KHYYYGGSYAMDYWGQGTSVTVSSAAATTTPAPRPPTPAPTIASQPLSLRPEAC
RPAAGG
AVHTRGLDFACDIYIWAPLAGTCGVLLLSLVITLYCKRGRKKLLYIFKQPFMRPV
QTTQE
EDGCSCRFPEEEEGGCELRVKFSRSADAPAYQQGQNQLYNELNLGRREEYDVLD
KRRGRD
PEMGGKPRRKNPQEGLYNELQKDKMAEAYSEIGMKGERRRGKGHDGLYQGLS
TATKDTYD
ALHMQALPP SEQ ID NO: 9 nucleotide sequence of CD20A LTG1495 (CAR 20A)
ATGCTCCTTCTCGTGACCTCCCTGCTTCTCTGCGAACTGCCCCATCCTGCCTTC
CTGCTG
ATTCCCGAGGTGCAGTTGCAACAGTCAGGAGCTGAACTGGTCAAGCCAGGAG
CCAGCGTG
AAGATGAGCTGCAAGGCCTCCGGTTACACCTTCACCTCCTACAACATGCACT
GGGTGAAA
CAGACCCCGGGACAAGGGCTCGAATGGATTGGCGCCATCTACCCCGGGAATG
GCGATACT
TCGTACAACCAGAAGTTCAAGGGAAAGGCCACCCTGACCGCCGACAAGAGC
TCCTCCACC
GCGTATATGCAGTTGAGCTCCCTGACCTCCGAGGACTCCGCCGACTACTACTG
CGCACGG
TCCAACTACTATGGAAGCTCGTACTGGTTCTTCGATGTCTGGGGGGCCGGCAC
CACTGTG
ACCGTCAGCTCCGGGGGCGGAGGATCCGGTGGAGGCGGAAGCGGGGGTGGA
GGATCCGAC
ATTGTGCTGACTCAGTCCCCGGCAATCCTGTCGGCCTCACCGGGCGAAAAGG
TCACGATG
ACTTGTAGAGCGTCGTCCAGCGTGAACTACATGGATTGGTACCAAAAGAAGC
CTGGATCG
TCACCCAAGCCTTGGATCTACGCTACATCTAACCTGGCCTCCGGCGTGCCAGC
GCGGTTC
AGCGGGTCCGGCTCGGGCACCTCATACTCGCTGACCATCTCCCGCGTGGAGG
CTGAGGAC
GCCGCGACCTACTACTGCCAGCAGTGGTCCTTCAACCCGCCGACTTTTGGAG
GCGGTACT
AAGCTGGAGATCAAAGCGGCCGCAACTACCACCCCTGCCCCTCGGCCGCCGA
CTCCGGCC
CCAACCATCGCAAGCCAACCCCTCTCCTTGCGCCCCGAAGCTTGCCGCCCGG
CCGCGGGT
GGAGCCGTGCATACCCGGGGGCTGGACTTTGCCTGCGATATCTACATTTGGG
CCCCGCTG
GCCGGCACTTGCGGCGTGCTCCTGCTGTCGCTGGTCATCACCCTTTACTGCAA
GAGGGGC
CGGAAGAAGCTGCTTTACATCTTCAAGCAGCCGTTCATGCGGCCCGTGCAGA
CGACTCAG
GAAGAGGACGGATGCTCGTGCAGATTCCCTGAGGAGGAAGAGGGGGGATGC
GAACTGCGC
GTCAAGTTCTCACGGTCCGCCGACGCCCCCGCATATCAACAGGGCCAGAATC
AGCTCTAC
AACGAGCTGAACCTGGAAGGAGAGAGGAGTACGACGTGCTGGACAAGCGA
CGCGGACGC
GACCCGGAGATGGGGGGAAACCACGGCGGAAAAACCCTCAGGAAGGACTG
TACAACGAA
CTCCAGAAAGACAAGATGGCGGAAGCCTACTCAGAAATCGGGATGAAGGGA
GAGCGGAGG
AGGGGAAAGGGTCACGACGGGCTGTACCAGGGACTGAGCACCGCCACTAAG
GATACCTAC
GATGCCTTGCATATGCAAGCACTCCCACCCCGG SEQ ID NO: 10 amino acid sequence of CD20A 1495 (CAR 20A)
MLLLVTSLLLCELPHPAFLLIPEVQLQQSGAELVKPGASVKMSCKASGYTFTSYN
MHWVK
QTPGQGLEWIGAIYPGNGDTSYNQKFKGKATLTADKSSSTAYMQLSSLTSEDSA
DYYCAR
```

```
SNYYGSSYWFFDVWGAGTTVTVSSGGGGSGGGGSGGGGSDIVLTQSPAILSASP
GEKVTM
TCRASSSVNYMDWYQKKPGSSPKPWIYATSNLASGVPARFSGSGSGTSYSLTISR
VEAED
AATYYCQQWSFNPPTFGGGTKLEIKAAATTTPAPRPPTPAPTIASQPLSLRPEACR
PAAG
GAVHTRGLDFACDIYIWAPLAGTCGVLLLSLVITLYCKRGRKKLLYIFKQPFMRP
VQTTQ
EEDGCSCRFPEEEEGGCELRVKFSRSADAPAYQQGQNQLYNELNLGRREEYDVL
DKRRGR
DPEMGGKPRRKNPQEGLYNELQKDKMAEAYSEIGMKGERRRGKGHDGLYQGL
STATKDTY
DALHMQALPPR

SEQ ID NO: 11 nucleotide sequence of leader/signal peptide sequence (LP)
atgctgctgctggtgaccagcctgctgctgtgcgaactgccgcatccggcgtttctgctgattccg SEQ ID NO: 12 amino acid sequence of leader/signal peptide sequence (LP)
MLLLVTSLLLCELPHPAFLLIP SEQ ID NO: 35 nucleotide sequence of DNA CD8 transmembrane domain
atttgggcccccgctggccggcacttgcggcgtgctcctgctgtcgctggtcatcaccat
tactgc SEQ ID NO: 36 amino acid sequence of CD8 transmembrane domain
Ile Trp Ala Pro Leu Ala Gly Thr Cys Gly Val Leu Leu Leu Ser Leu
Val Ile Thr Leu Tyr Cys SEQ ID NO: 37 nucleotide sequence of DNA CD8 hinge domain
actaccaccctgcccctcggccgccgactccggccccaaccatcgcaagccaaccctc
tccttgcgccccgaagcttgccgcccggccgcgggtggagccgtgcataccgggggctg
gactttgcctgcgatatctac SEQ ID NO: 38 amino acid sequence of CD8 hinge domain
Thr Thr Thr Pro Ala Pro Arg Pro Pro Thr Pro Ala Pro Thr Ile Ala
Ser Gln Pro Leu Ser Leu Arg Pro Glu Ala Cys Arg Pro Ala Ala Gly
Gly Ala Val His Thr Arg Gly Leu Asp Phe Ala Cys Asp Ile Tyr SEQ ID NO: 39 amino acid sequence of amino acid numbers 137 to 206 hinge and
transmembrane region of CD8.alpha. (NCBI RefSeq: NP.sub.--001759.3)
Thr Thr Thr Pro Ala Pro Arg Pro Pro Thr Pro Ala Pro Thr Ile Ala Ser Gln Pro Leu
Ser Leu Arg Pro Glu Ala Cys Arg Pro Ala Ala Gly Gly Ala Val His Thr Arg Gly Leu
Asp Phe Ala Cys Asp Ile Tyr Ile Trp Ala Pro Leu Ala Gly Thr Cys Gly Val Leu Leu
Leu Ser Leu Val Ile Thr Leu Tyr Cys SEQ ID NO: 40 nucleotide sequence of DNA signaling domain of 4-1BB
aagaggggccggaagaagctgattacatcttcaagcagccgttcatggcccgtgcag
acgactcaggaagaggacggatgctcgtgcagattccctgaggaggaagaggggggatgc
gaactg SEQ ID NO: 41 amino acid sequence of signaling domain of 4-1BB
Lys Arg Gly Arg Lys Lys Leu Leu Tyr Ile Phe Lys Gln Pro Phe Met
Arg Pro Val Gln Thr Thr Gln Glu Glu Asp Gly Cys Ser Cys Arg Phe
Pro Glu Glu Glu Glu Gly Gly Cys Glu Leu SEQ ID NO: 42 nucleotide sequence of DNA signaling domain of CD3-zeta
cgcgtcaagttctcacggtccgccgacgcccccgcatatcaacagggccagaatcagctc
tacaacgagctgaacctgggaaggagagaggagtacgacgtgctggacaagcgacgcgga
cgcgacccggagatggggggggaaaccacggcggaaaaaccctcaggaaggactgtacaac
gaactccagaaagacaagatggcggaagcctactcagaaatcggggatgaagggagagegg
aggaggggaaagggtcacgacgggctgtaccagggactgagcggccaccgccactaaggatacc
tacgatgccttgcatatgcaagcactcccaccccgg SEQ ID NO: 43 amino acid sequence of CD3zeta
Arg Val Lys Phe Ser Arg Ser Ala Asp Ala Pro Ala Tyr Gln Gln Gly Gln Asn Gln Leu
Tyr Asn Glu Leu Asn Leu Gly Arg Arg Glu Glu Tyr Asp Val Leu Asp Lys Arg Arg
Gly Arg Asp Pro Glu Met Gly Gly Lys Pro Arg Arg Lys Asn Pro Gln Glu Gly Leu
Tyr Asn Glu Leu Gln Lys Asp Lys Met Ala Glu Ala Tyr Ser Glu Ile Gly Met Lys Gly
Glu Arg Arg Arg Gly Lys Gly His Asp Gly Leu Tyr Gln Gly Leu Ser Thr Ala Thr Lys
Asp Thr Tyr Asp Ala Leu His Met Gln Ala Leu Pro Pro Arg SEQ ID NO: 44 nucleotide sequence of ScFv CD19 (FMC63)
gacattcagatgactcagaccacctatccttgtccgcgtcactgggagacagagtgaccat
ctcgtgtcgcgcaagccaggatatctccaagtacctgaactggtaccaacagaagcccga
cgggactgtgaagctgctgatctaccacacctcacgcctgcacagcggagtgccaagcag
attctccggctccggctcgggaaccgattactcgcttaccattagcaacctcgagcagga
ggacatcgctacctacttctgccagcaaggaaataccctgccctacaccttcggcggagg
aaccaaattggaaatcaccggcggaggaggctccggggggaggaggttccggggggcgggg
ttccgaagtgaagctccaggagtccggccccggcctggtggcgccgtcgcaatcactctc
```

-continued

```
tgtgacctgtaccgtgtcgggagtgtccctgcctgattacggcgtgagctggattcggca
gccgccgcggaagggcctggaatggctgggtgtcatctggggatccgagactacctacta
caactcggccctgaagtcccgcctgactatcatcaaagacaactcgaagtcccaggtctt
tctgaagatgaactccctgcaaactgacgacaccgccatctattactgtgctaagcacta
ctactacggtggaagctatgctatggactactgggggcaaggcacttcggtgactgtgtc
aagc
```

SEQ ID NO: 45 amino acid sequence of ScFv CD19 (FMC63)
Asp Ile Gln Met Thr Gln Thr Thr Ser Ser Leu Ser Ala Ser Leu Gly Asp Arg Val Thr
Ile Ser Cys Arg Ala Ser Gln Asp Ile Ser Lys Tyr Leu Asn Trp Tyr Gln Gln Lys Pro
Asp Gly Thr Val Lys Leu Leu Ile Tyr His Thr Ser Arg Leu His Ser Gly Val Pro Ser
Arg Phe Ser Gly Ser Gly Ser Gly Thr Asp Tyr Ser Leu Thr Ile Ser Asn Leu Glu Gln
Glu Asp Ile Ala Thr Tyr Phe Cys Gln Gln Gly Asn Thr Leu Pro Tyr Thr Phe Gly Gly
Gly Thr Lys Leu Glu Ile Thr Gly Gly Gly Gly Ser Gly Gly Gly Gly Ser Gly Gly Gly
Gly Ser Glu Val Lys Leu Gln Glu Ser Gly Pro Gly Leu Val Ala Pro Ser Gln Ser Leu
Ser Val Thr Cys Thr Val Ser Gly Val Ser Leu Pro Asp Tyr Gly Val Ser Trp Ile Arg
Gln Pro Pro Arg Lys Gly Leu Glu Trp Leu Gly Val Ile Trp Gly Ser Glu Thr Thr Tyr
Tyr Asn Ser Ala Leu Lys Ser Arg Leu Thr Ile Ile Lys Asp Asn Ser Lys Ser Gln Val
Phe Leu Lys Met Asn Ser Leu Gln Thr Asp Asp Thr Ala Ile Tyr Tyr Cys Ala Lys His
Tyr Tyr Tyr Gly Gly Ser Tyr Ala Met Asp Tyr Trp Gly Gln Gly Thr Ser Val Thr Val
Ser Ser SEQ ID NO: 46 nucleotide sequence of anti-CD33 CAR (LTG1936)
```
ATGCTGCTGCTGGTGACCAGCCTGCTGCTGTGCGAACTGCCGCATCCGGCGTTTCTG
CTGATTCCGCAGGTGCAGCTGGTGCAATCTGGGGCAGAGGTGAAAAAGCCCGGGGA
GTCTCTGAGGATCTCCTGTAAGGGTTCTGGATTCAGTTTTCCCACCTACTGGATCGGC
TGGGTGCGCCAGATGCCCGGGAAAGGCCTGGAGTGGATGGGGATCATCTATCCTGG
TGACTCTGATACCAGATACAGCCCGTCCTTCCAAGGCCAGGTCACCATCTCAGCCGA
CAAGTCCATCAGCACCGCCTACCTGCAGTGGAGCAGCCTGAAGGCCTCGGACACCG
CCATGTATTACTGTGCGAGACTAGTTGGAGATGGCTACAATACGGGGGCTTTTGATA
TCTGGGGCCAAGGGACAATGGTCACCGTCTCTTCAGGAGGTGGCGGGTCTGGTGGT
GGCGGTAGCGGTGGTGCGGATCCGATATTGTGATGACCCACACTCCACTCTCTCTG
TCCGTCACCCCTGGACAGCCGGCCTCCATCTCCTGCAAGTCTAGTCAGAGCCTCCTG
CATAGTAATGGAAAGACCTATTTGTATTGGTACCTGCAGAAGCCAGGCCAGCCTCCA
CAGCTCCTGATCTATGGAGCTTCCAACCGGTTCTCTGGAGTGCCAGACAGGTTCAGT
GGCAGCGGGTCAGGGACAGATTTCACACTGAAAATCAGCCGGGTGGAGGCTGAGGA
TGTTGGGGTTTATTACTGCATGCAAAGTATACAGCTTCCTATCACCTTCGGCCAAGG
GACACGACTGGAGATTAAAGCGGCCGCAACTACCACCCCTGCCCCTCGGCCGCCGA
CTCCGGCCCCAACCATCGCAAGCCAACCCCTCTCCTTGCGCCCCGAAGCTTGCCGCC
CGGCCGCGGGTGGAGCCGTGCATACCCGGGGGCTGGACTTTGCCTGCGATATCTAC
ATTTGGGCCCCGCTGGCCGGCACTTGCGGCGTGCTCCTGCTGTCGCTGGTCATCACC
CTTTACTGCAAGAGGGGCCGGAAGAAGCTGCTTTACATCTTCAAGCAGCCGTTCATG
CGGCCCGTGCAGACGACTCAGGAAGAGGACGGATGCTCGTCGCAGATTCCCTGAGGA
GGAAGAGGGGGGATGCGAACTGCGCGTCAAGTTCTCACGGTCCGCCGACGCCCCCG
CATATCAACAGGGCCAGAATCAGCTCTACAACGAGCTGAACCTGGGAAGGAGAGAG
GAGTACGACGTGCTGGACAAGCGACGCGGACGCGACCCGGAGATGGGGGGGAAAC
CACGGCGGAAAAACCCTCAGGAAGGACTGTACAACGAACTCCAGAAAGACAAGAT
GGCGGAAGCCTACTCAGAAATCGGGATGAAGGGAGAGCGGAGGAGGGGAAAGGGT
CACGACGGGCTGTACCAGGGACTGAGCACCGCCACTAAGGATACCTACGATGCCTT
GCATATGCAAGCACTCCCACCCCGG
```

SEQ ID NO: 47 amino acid sequence of anti-CD33 CAR (LTG1936)
MLLLVTSLLLCELPHPAFLLIPQVQLVQSGAEVKKPGESLRISCKGSGFSFPTYWIGWVR
QMPGKGLEWMGIIYPGDSDTRYSPSFQGQVTISADKSISTAYLQWSSLKASDTAMYYCA
RLVGDGYNTGAFDIWQGTMVTVSSGGGGSGGGGSGGGGSDIVIVITHTPLSLSVTPGQP
ASISCKSSQSLLHSNGKTYLYWYLQKPGQPPQLLIYGASNRFSGVPDRFSGSGSGTDFTL
KISRVEAEDVGVYYCMQSIQLPITFGQGTRLEIKAAATTTPAPRPPTPAPTIASQPLSLRPE
ACRPAAGGAVHTRGLDFACDIYIWAPLAGTCGVLLLSLVITLYCKRGRKKLLYIFKQPF
MRPVQTTQEEDGCSCRFPEEEEGGCELRVKFSRSADAPAYQQGQNQLYNELNLGRREE
YDVLDKRRGRDPEMGGKPRRKNPQEGLYNELQKDKMAEAYSEIGMKGERRRGKGHD
GLYQGLSTATKDTYDALHMQALPP SEQ ID NO: 48 nucleotide sequence of anti-mesothelin CAR (LTG1904)
```
ATGCTGCTGCTGGTGACCAGCCTGCTGCTGTGCGAACTGCCGCATCCGGCGTTTCTG
CTGATTCCGGAGGTCCAGCTGGTACAGTCTGGGGGAGGCTTGGTACAGCCTGGGGG
GTCCCTGAGACTCTCCTGTGCAGCCTCTGGATTCACCTTTGATGATTATGCCATGCAC
TGGGTCCGGCAAGCTCCAGGGAAGGGCCTGGAGTGGGTCTCAGGTATTAGTTGGAA
TAGTGGTAGCATAGGCTATGCGGACTCTGTGAAGGGCCGATTCACCATCTCCAGAG
ACAACGCCAAGAACTCCCTGTATCTGCAAATGAACAGTCTGAGAGCTGAGGACACG
GCCTTGTATTACTGTGCAAAAGATTTATCGTCAGTGGCTGGACCCTTTAACTACTGG
GGCCAGGGCACCCTGGTCACCGTCTCCTCAGGAGGTGGCGGGTCTGGTGGAGGCGG
TAGCGGCGGTGGCGGATCCTCTTCTGAGCTGACTCAGGACCCTGCTGTGTCTGTGGC
CTTGGGACAGACAGTCAGGATCACATGCCAAGGAGACAGCCTCAGAAGCTATTATG
CAAGCTGGTACCAGCAGAAGCCAGGACAGGCCCCTGTACTTGTCATCTATGGTAAA
AACAACCGGCCCTCAGGGATCCCAGACCGATTCTCTGGCTCCAGCTCAGGAAACAC
AGCTTCCTTGACCATCACTGGGGCTCAGGCGGAGGATGAGGCTGACTATTACTGTAA
CTCCCGGGACAGCAGTGGTAACCATCTGGTATTCGGCGGAGGCACCCAGCTGACCG
TCCTCGGTGCGCCGCAACTACCACCCCTGCCCCTCGGCCGCCGACTCCGGCCCCAA
CCATCGCAAGCCAACCCCTCTCCTTGCGCCCCGAAGCTTGCCGCCCGGCCGCGGGTG
```

-continued

```
GAGCCGTGCATACCCGGGGGCTGGACTTTGCCTGCGATATCTACATTTGGGCCCCGC
TGGCCGGCACTTGCGGCGTGCTCCTGCTGTCGCTGGTCATCACCCTTTACTGCAAGA
GGGGCCGGAAGAAGCTGCTTTACATCTTCAAGCAGCCGTTCATGCGGCCCGTGCAG
ACGACTCAGGAAGAGGACGGATGCTCGTGCAGATTCCCTGAGGAGGAAGAGGGGG
GATGCGAACTGCGCGTCAAGTTCTCACGGTCCGCCGACGCCCCCGCATATCAACAG
GGCCAGAATCAGCTCTACAACGAGCTGAACCTGGGAAGGAGAGAGGAGTACGACG
TGCTGGACAAGCGACGCGGACGCGACCCGGAGATGGGGGGGAAACCACGGCGGAA
AAACCCTCAGGAAGGACTGTACAACGAACTCCAGAAAGACAAGATGGCGGAAGCC
TACTCAGAAATCGGGATGAAGGGAGAGCGGAGGAGGGGAAAGGGTCACGACGGC
TGTACCAGGGACTGAGCACCGCCACTAAGGATACCTACGATGCCTTGCATATGCAA
GCACTCCCACCCCGG
```

SEQ ID NO: 49 amino acid sequence of anti-mesothelin CAR (LTG1904)
```
MLLLVTSLLLCELPHPAFLLIPEVQLVQSGGGLVQPGGSLRLSCAASGFTFDDYAMHWV
RQAPGKGLEWVSGISWNSGSIGYADSVKGRFTISRDNAKNSLYLQMNSLRAEDTALYY
CAKDLSSVAGPFNYWGQGTLVTVSSGGGGSGGGGSGGGGSSSELTQDPAVSVALGQT
VRITCQGDSLRSYYASWYQQKPGQAPVLVIYGKNNRPSGIPDRFSGSSSGNTASLTITGA
QAEDEADYYCNSRDSSGNHLVFGGGTQLTVLGAAATTTPAPRPPTPAPTIASQPLSRPE
ACRPAAGGAVHTRGLDFACDIYIWAPLAGTCGVLLLSLVITLYCKRGRKKLLYIFKQPF
MRPVQTTQEEDGCSCRFPEEEEGGCELRVKFSRSADAPAYQQGQNQLYNELNLGRREE
YDVLDKRRGRDPEMGGKPRRKNPQEGLYNELQKDKMAEAYSEIGMKGERRRGKGHD
GLYQGLSTATKDTYDALHMQALPPR
```

What is claimed is:

1. An isolated nucleic acid molecule encoding a CD19/CD20 tandem chimeric antigen receptor (CAR) comprising the amino acid sequence of SEQ ID No: 2 or 4, wherein the nucleic acid sequence comprises SEQ ID NO: 1 or 3, or a sequence with 85%, 90%, 95%, 96%, 97%, 98% or 99% identity thereof.

2. The isolated nucleic acid molecule of claim 1, wherein the CAR further comprises at least one intracellular signaling domain comprising a costimulatory domain, a primary signaling domain, or any combination thereof.

3. The isolated nucleic acid molecule of claim 2, wherein the encoded at least one costimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), or any combination thereof.

4. A CAR encoded by an isolated nucleic acid molecule encoding a CD19/CD20 CAR comprising the amino acid sequence of SEQ ID NO: 2 or 4.

5. The CAR of claim 4, wherein the CAR further comprises at least one intracellular signaling domain comprising a costimulatory domain and a primary signaling domain.

6. The CAR of claim 5, wherein the at least one intracellular signaling domain comprises a costimulatory domain comprising a functional signaling domain of a protein selected from the group consisting of OX40, CD70, CD27, CD28, CD5, ICAM-1, LFA-1 (CD11a/CD18), ICOS (CD278), DAP10, DAP12, and 4-1BB (CD137).

* * * * *

SEQUENCE LISTING

<160> NUMBER OF SEQ ID NOS: 30

<210> SEQ ID NO 1
<211> LENGTH: 2283
<212> TYPE: DNA
<213> ORGANISM: Artificial
<220> FEATURE:
<223> OTHER INFORMATION: Leader-CD19 VL-Whitlow linker CD19 VH (GGGGS)-5
    CD20 VH (GGGGS)-3 CD20 VL CD8 hinge+TM-4-1BB- CD3z  (Construct CAR
    1920)

<400> SEQUENCE: 1
atgctccttc tcgtgacctc cctgcttctc tgcgaactgc ccatcctgc cttcctgctg      60 attcccgaca ttcagatgac tcagaccacc tcctccctgt ccgcctccct gggcgaccgc     120
gtgaccatct catgccgcgc cagccaggac atctcgaagt acctcaactg gtaccagcag     180
aagcccgacg gaaccgtgaa gctcctgatc taccacacct cccggctgca cagcggagtg     240
ccgtctagat tctcgggttc ggggtcggga actgactact cccttactat ttccaacctg     300
gagcaggagg atattgccac ctacttctgc caacaaggaa acaccctgcc gtacactttt     360 ggcggggggaa ccaagctgga aatcactggc agcacatccg gttccgggaa gcccggctcc     420
ggagagggca gcaccaaggg ggaagtcaag ctgcaggaat caggacctgg cctggtggcc     480
ccgagccagt cactgtccgt gacttgtact gtgtccggag tgtcgctccc ggattacgga     540
gtgtcctgga tcaggcagcc acctcggaaa ggattgaat ggctcggagt catctgggt     600 tccgaaacca cctattacaa ctcggcactg aaatccaggc tcaccattat caaggataac     660
tccaagtcac aagtgttcct gaagatgaat agcctgcaga ctgacgacac ggcgatctac     720
tattgcgcca agcactacta ctacggcgga tcctacgcta tggactactg gggccagggg     780
accagcgtga ccgtgtcatc cggaggcggc ggcagcggcg gggagggtc cggaggggt     840 ggttctggtg gaggaggatc gggaggcggt ggcagcgagg tgcagttgca acagtcagga     900
gctgaactgg tcaagccagg agccagcgtg aagatgagct gcaaggcctc cggttacacc     960
ttcacctcct acaacatgca ctgggtgaaa cagaccccgg acaagggct cgaatggatt    1020 ggcgccatct accccgggaa tggcgatact tcgtacaacc agaagttcaa gggaaaggcc    1080
accctgaccg ccgacaagag ctcctccacc gcgtatatgc agttgagctc cctgacctcc    1140
```

```
gaggactccg ccgactacta ctgcgcacgg tccaactact atggaagctc gtactggttc    1200
ttcgatgtct gggggccgg caccactgtg accgtcagct ccggggggcgg aggatccggt    1260 ggaggcggaa gcggggggtgg aggatccgac attgtgctga ctcagtcccc ggcaatcctg    1320
tcggcctcac cggggcgaaaa ggtcacgatg acttgtagag cgtcgtccag cgtgaactac    1380
atggattggt accaaaagaa gcctggatcg tcacccaagc cttggatcta cgctacatct    1440
aacctggcct ccggcgtgcc agcgcggttc agcgggtccg gctcgggcac ctcatactcg    1500
ctgaccatct cccgcgtgga ggctgaggac gccgcgacct actactgcca gcagtggtcc    1560
ttcaacccgc cgacttttgg aggcggtact aagctggaga tcaaagcggc cgcaactacc    1620 accctgccc ctcggccgcc gactccggcc ccaaccatcg caagccaacc cctctccttg    1680
cgccccgaag cttgccgccc ggccgcgggt ggagccgtgc ataccggggg ctggactttt    1740
gcctgcgata tctacatttg gccccgctg gccggcactt gcggcgtgct cctgctgtcg    1800
ctggtcatca cccttttactg caagagggggc cggaagaagc tgctttacat cttcaagcag    1860
ccgttcatgc ggcccgtgca gacgactcag gaagaggacg gatgctcgtg cagattccct    1920
gaggaggaag aggggggatg cgaactgcgc gtcaagttct cacggtccgc cgacgccccc    1980
gcatatcaac agggccagaa tcagctctac aacgagctga acctgggaag agagaggag    2040 tacgacgtgc tggacaagcg acgcggacgc gacccggaga tggggggggaa accacggcgg    2100 aaaaaccctc aggaaggact gtacaacgaa ctccagaaag acaagatggc ggaagcctac    2160
tcagaaatcg ggatgaaggg agagcggagg aggggaaagg gtcacgacgg gctgtaccag    2220
ggactgagca ccgccactaa ggatacctac gatgccttgc atatgcaagc actcccaccc    2280
cgg                                                                  2283
```

<210> SEQ ID NO 2
<211> LENGTH: 761
<212> TYPE: PRT
<213> ORGANISM: Artificial
<220> FEATURE:
<223> OTHER INFORMATION: Leader-CD19 VL-Whitlow linker CD19 VH (GGGGS)-5
    CD20 VH (GGGGS)-3 CD20 VL CD8 hinge+TM-4-1BB- CD3z (Construct CAR
    1920)

<400> SEQUENCE: 2

```
Met Leu Leu Leu Val Thr Ser Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140
```

-continued

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
            165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
    195                 200                 205

Ala Leu Lys Ser Arg Leu Thr Ile Ile Lys Asp Asn Ser Lys Ser Gln
210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Gly Gly Ser Tyr Ala Met Asp Tyr
            245                 250                 255

Trp Gly Gln Gly Thr Ser Val Thr Val Ser Ser Gly Gly Gly Gly Ser
            260                 265                 270

Gly Gly Gly Gly Ser Gly Gly Gly Gly Ser Gly Gly Gly Gly Ser Gly
            275                 280                 285

Gly Gly Gly Ser Glu Val Gln Leu Gln Gln Ser Gly Ala Glu Leu Val
    290                 295                 300

Lys Pro Gly Ala Ser Val Lys Met Ser Cys Lys Ala Ser Gly Tyr Thr
305                 310                 315                 320

Phe Thr Ser Tyr Asn Met His Trp Val Lys Gln Thr Pro Gly Gln Gly
            325                 330                 335

Leu Glu Trp Ile Gly Ala Ile Tyr Pro Gly Asn Gly Asp Thr Ser Tyr
            340                 345                 350

Asn Gln Lys Phe Lys Gly Lys Ala Thr Leu Thr Ala Asp Lys Ser Ser
            355                 360                 365

Ser Thr Ala Tyr Met Gln Leu Ser Ser Leu Thr Ser Glu Asp Ser Ala
    370                 375                 380

Asp Tyr Tyr Cys Ala Arg Ser Asn Tyr Tyr Gly Ser Ser Tyr Trp Phe
385                 390                 395                 400

Phe Asp Val Trp Gly Ala Gly Thr Thr Val Thr Val Ser Ser Gly Gly
            405                 410                 415

Gly Gly Ser Gly Gly Gly Gly Ser Gly Gly Gly Gly Ser Asp Ile Val
            420                 425                 430

Leu Thr Gln Ser Pro Ala Ile Leu Ser Ala Ser Pro Gly Glu Lys Val
            435                 440                 445

Thr Met Thr Cys Arg Ala Ser Ser Ser Val Asn Tyr Met Asp Trp Tyr
450                 455                 460

Gln Lys Lys Pro Gly Ser Ser Pro Lys Pro Trp Ile Tyr Ala Thr Ser
465                 470                 475                 480

Asn Leu Ala Ser Gly Val Pro Ala Arg Phe Ser Gly Ser Gly Ser Gly
            485                 490                 495

Thr Ser Tyr Ser Leu Thr Ile Ser Arg Val Glu Ala Glu Asp Ala Ala
            500                 505                 510

Thr Tyr Tyr Cys Gln Gln Trp Ser Phe Asn Pro Pro Thr Phe Gly Gly
            515                 520                 525

Gly Thr Lys Leu Glu Ile Lys Ala Ala Ala Thr Thr Thr Pro Ala Pro
    530                 535                 540

Arg Pro Pro Thr Pro Ala Pro Thr Ile Ala Ser Gln Pro Leu Ser Leu
545                 550                 555                 560

```
Arg Pro Glu Ala Cys Arg Pro Ala Ala Gly Ala Val His Thr Arg
            565                 570                 575

Gly Leu Asp Phe Ala Cys Asp Ile Tyr Ile Trp Ala Pro Leu Ala Gly
        580                 585                 590

Thr Cys Gly Val Leu Leu Leu Ser Leu Val Ile Thr Leu Tyr Cys Lys
        595                 600                 605

Arg Gly Arg Lys Lys Leu Leu Tyr Ile Phe Lys Gln Pro Phe Met Arg
        610                 615                 620

Pro Val Gln Thr Thr Gln Glu Glu Asp Gly Cys Ser Cys Arg Phe Pro
625                 630                 635                 640

Glu Glu Glu Glu Gly Gly Cys Glu Leu Arg Val Lys Phe Ser Arg Ser
                    645                 650                 655

Ala Asp Ala Pro Ala Tyr Gln Gln Gly Gln Asn Gln Leu Tyr Asn Glu
                660                 665                 670

Leu Asn Leu Gly Arg Arg Glu Glu Tyr Asp Val Leu Asp Lys Arg Arg
            675                 680                 685

Gly Arg Asp Pro Glu Met Gly Gly Lys Pro Arg Arg Lys Asn Pro Gln
        690                 695                 700

Glu Gly Leu Tyr Asn Glu Leu Gln Lys Asp Lys Met Ala Glu Ala Tyr
705                 710                 715                 720

Ser Glu Ile Gly Met Lys Gly Glu Arg Arg Arg Gly Lys Gly His Asp
                    725                 730                 735

Gly Leu Tyr Gln Gly Leu Ser Thr Ala Thr Lys Asp Thr Tyr Asp Ala
                740                 745                 750

Leu His Met Gln Ala Leu Pro Pro Arg
            755                 760

<210> SEQ ID NO 3
<211> LENGTH: 2283
<212> TYPE: DNA
<213> ORGANISM: Artificial
<220> FEATURE:
<223> OTHER INFORMATION: Leader-CD20 VH (GGGGS)3 - CD20 VL -(GGGGS)5
      -CD19 VL-Whitlow linker- CD19 VH CD8 hinge+TM-4-1BB- CD3z
      (Construct 2019)

<400> SEQUENCE: 3
atgctccttc tcgtgaccct cctgcttctc tgcgaactgc ccatcctgc cttcctgctg     60 attcccgagg tgcagttgca acagtcagga gctgaactgg tcaagccagg agccagcgtg    120
aagatgagct gcaaggcctc cggttacacc ttcacctcct acaacatgca ctgggtgaaa    180
cagaccccgg acaagggct cgaatggatt ggcgccatct accccgggaa tggcgatact     240
tcgtacaacc agaagttcaa gggaaaggcc accctgaccg ccgacaagag ctcctccacc    300
gcgtatatgc agttgagctc cctgacctcc gaggactccg ccgactacta ctgcgcacgg    360
tccaactact atggaagctc gtactggttc ttcgatgtct ggggggccgg caccactgtg    420
accgtcagct ccggggggcgg aggatccggt ggaggcggaa gcggggtgg aggatccgac    480 attgtgctga ctcagtcccc ggcaatcctg tcggcctcac cgggcgaaaa ggtcacgatg    540
acttgtagag cgtcgtccag cgtgaactac atggattggt accaaaagaa gcctggatcg    600
tcacccaagc cttggatcta cgctacatct aacctggcct ccggcgtgcc agcgcggttc    660
agcgggtccg gctcgggcac ctcatactcg ctgaccatct cccgcgtgga ggctgaggac    720
gccgcgacct actactgcca gcagtggtcc ttcaaccccg cgactttggg aggcggtact    780
aagctggaga tcaaaggagg cggcggcagc ggcggggag ggtccggagg gggtggttct    840
```

```
ggtggaggag gatcgggagg cggtggcagc gacattcaga tgactcagac cacctcctcc    900
ctgtccgcct ccctgggcga ccgcgtgacc atctcatgcc gcgccagcca ggacatctcg    960
aagtacctca actggtacca gcagaagccc gacggaaccg tgaagctcct gatctaccac   1020
acctcccggc tgcacagcgg agtgccgtct agattctcgg gttcggggtc gggaactgac   1080
tactccctta ctatttccaa cctggagcag gaggatattg ccacctactt ctgccaacaa   1140
ggaaacaccc tgccgtacac ttttggcggg ggaaccaagc tggaaatcac tggcagcaca   1200
tccggttccg ggaagcccgg ctccggagag ggcagcacca agggggaagt caagctgcag   1260
gaatcaggac ctggcctggt ggccccgagc cagtcactgt ccgtgacttg tactgtgtcc   1320
ggagtgtcgc tcccggatta cggagtgtcc tggatcaggc agccacctcg gaaaggattg   1380
gaatggctcg gagtcatctg gggttccgaa accaccatt acaactcggc actgaaatcc   1440
aggctcacca ttatcaagga taactccaag tcacaagtgt tcctgaagat aatagcctg   1500
cagactgacg acacggcgat ctactattgc gccaagcact actactacgg cggatcctac   1560
gctatggact actggggcca ggggaccagc gtgaccgtgt catccgcggc cgcaactacc   1620
accctgccc tcggccgcc gactccggcc ccaaccatcg caagccaacc cctctccttg   1680
cgccccgaag cttgccgccc ggccgcgggt ggagccgtgc ataccggggg ctggactttt   1740
gcctgcgata tctacatttg ggccccgctg gccggcactt gcggcgtgct cctgctgtcg   1800
ctggtcatca cccctttactg caagagggg cggaagaagc tgctttacat cttcaagcag   1860
ccgttcatgc ggcccgtgca gacgactcag gaagaggacg gatgctcgtg cagattccct   1920
gaggaggaag aggggggatg cgaactgcgc gtcaagttct cacggtccgc cgacgccccc   1980
gcatatcaac agggccagaa tcagctctac aacgagctga acctgggaag gagagaggag   2040
tacgacgtgc tggacaagcg cacgcggacg gaccccgaga tgggggggaa ccacggcgg   2100
aaaaaccctc aggaaggact gtacaacgaa ctccagaaag acaagatggc ggaagcctac   2160
tcagaaatcg ggatgaaggg agagcggagg agggaaagg gtcacgacgg gctgtaccag   2220
ggactgagca ccgccactaa ggatacctac gatgccttgc atatgcaagc actcccaccc   2280
cgg                                                                2283
```

<210> SEQ ID NO 4
<211> LENGTH: 761
<212> TYPE: PRT
<213> ORGANISM: Artificial
<220> FEATURE:
<223> OTHER INFORMATION: Leader-CD20 VH (GGGGS)3 - CD20 VL -(GGGGS)5
    -CD19 VL-Whitlow linker- CD19 VH CD8 hinge+TM-4-1BB- CD3z amino
    acid sequence (Construct CAR 2019)

<400> SEQUENCE: 4

Met Leu Leu Leu Val Thr Ser Leu Leu Leu Cys Glu Leu Pro His Pro
1               5                   10                  15

Ala Phe Leu Leu Ile Pro Glu Val Gln Leu Gln Gln Ser Gly Ala Glu
            20                  25                  30

Leu Val Lys Pro Gly Ala Ser Val Lys Met Ser Cys Lys Ala Ser Gly
        35                  40                  45

Tyr Thr Phe Thr Ser Tyr Asn Met His Trp Val Lys Gln Thr Pro Gly
    50                  55                  60

Gln Gly Leu Glu Trp Ile Gly Ala Ile Tyr Pro Gly Asn Gly Asp Thr
65                  70                  75                  80

Ser Tyr Asn Gln Lys Phe Lys Gly Lys Ala Thr Leu Thr Ala Asp Lys
                85                  90                  95

```
Ser Ser Ser Thr Ala Tyr Met Gln Leu Ser Ser Leu Thr Ser Glu Asp
            100                 105                 110

Ser Ala Asp Tyr Tyr Cys Ala Arg Ser Asn Tyr Tyr Gly Ser Ser Tyr
        115                 120                 125

Trp Phe Asp Val Trp Gly Ala Gly Thr Thr Val Thr Val Ser Ser
    130                 135                 140

Gly Gly Gly Gly Ser Gly Gly Gly Gly Ser Gly Gly Gly Gly Ser Asp
145                 150                 155                 160

Ile Val Leu Thr Gln Ser Pro Ala Ile Leu Ser Ala Ser Pro Gly Glu
                165                 170                 175

Lys Val Thr Met Thr Cys Arg Ala Ser Ser Ser Val Asn Tyr Met Asp
                180                 185                 190

Trp Tyr Gln Lys Lys Pro Gly Ser Ser Pro Lys Pro Trp Ile Tyr Ala
            195                 200                 205

Thr Ser Asn Leu Ala Ser Gly Val Pro Ala Arg Phe Ser Gly Ser Gly
            210                 215                 220

Ser Gly Thr Ser Tyr Ser Leu Thr Ile Ser Arg Val Glu Ala Glu Asp
225                 230                 235                 240

Ala Ala Thr Tyr Tyr Cys Gln Gln Trp Ser Phe Asn Pro Pro Thr Phe
                245                 250                 255

Gly Gly Gly Thr Lys Leu Glu Ile Lys Gly Gly Gly Ser Gly Gly
                260                 265                 270

Gly Gly Ser Gly Gly Gly Ser Gly Gly Gly Ser Gly Gly Gly
            275                 280                 285

Gly Ser Asp Ile Gln Met Thr Gln Thr Thr Ser Ser Leu Ser Ala Ser
290                 295                 300

Leu Gly Asp Arg Val Thr Ile Ser Cys Arg Ala Ser Gln Asp Ile Ser
305                 310                 315                 320

Lys Tyr Leu Asn Trp Tyr Gln Gln Lys Pro Asp Gly Thr Val Lys Leu
            325                 330                 335

Leu Ile Tyr His Thr Ser Arg Leu His Ser Gly Val Pro Ser Arg Phe
                340                 345                 350

Ser Gly Ser Gly Ser Gly Thr Asp Tyr Ser Leu Thr Ile Ser Asn Leu
            355                 360                 365

Glu Gln Glu Asp Ile Ala Thr Tyr Phe Cys Gln Gln Gly Asn Thr Leu
370                 375                 380

Pro Tyr Thr Phe Gly Gly Gly Thr Lys Leu Glu Ile Thr Gly Ser Thr
385                 390                 395                 400

Ser Gly Ser Gly Lys Pro Gly Ser Gly Glu Gly Ser Thr Lys Gly Glu
            405                 410                 415

Val Lys Leu Gln Glu Ser Gly Pro Gly Leu Val Ala Pro Ser Gln Ser
            420                 425                 430

Leu Ser Val Thr Cys Thr Val Ser Gly Val Ser Leu Pro Asp Tyr Gly
                435                 440                 445

Val Ser Trp Ile Arg Gln Pro Pro Arg Lys Gly Leu Glu Trp Leu Gly
            450                 455                 460

Val Ile Trp Gly Ser Glu Thr Thr Tyr Tyr Asn Ser Ala Leu Lys Ser
465                 470                 475                 480

Arg Leu Thr Ile Ile Lys Asp Asn Ser Lys Ser Gln Val Phe Leu Lys
                485                 490                 495

Met Asn Ser Leu Gln Thr Asp Asp Thr Ala Ile Tyr Tyr Cys Ala Lys
                500                 505                 510
```

His Tyr Tyr Tyr Gly Gly Ser Tyr Ala Met Asp Tyr Trp Gly Gln Gly
            515                 520                 525

Thr Ser Val Thr Val Ser Ser Ala Ala Thr Thr Thr Pro Ala Pro
        530                 535                 540

Arg Pro Pro Thr Pro Ala Pro Thr Ile Ala Ser Gln Pro Leu Ser Leu
545                 550                 555                 560

Arg Pro Glu Ala Cys Arg Pro Ala Ala Gly Gly Ala Val His Thr Arg
                565                 570                 575

Gly Leu Asp Phe Ala Cys Asp Ile Tyr Ile Trp Ala Pro Leu Ala Gly
            580                 585                 590

Thr Cys Gly Val Leu Leu Leu Ser Leu Val Ile Thr Leu Tyr Cys Lys
        595                 600                 605

Arg Gly Arg Lys Lys Leu Leu Tyr Ile Phe Lys Gln Pro Phe Met Arg
610                 615                 620

Pro Val Gln Thr Thr Gln Glu Glu Asp Gly Cys Ser Cys Arg Phe Pro
625                 630                 635                 640

Glu Glu Glu Glu Gly Gly Cys Glu Leu Arg Val Lys Phe Ser Arg Ser
                645                 650                 655

Ala Asp Ala Pro Ala Tyr Gln Gln Gly Gln Asn Gln Leu Tyr Asn Glu
            660                 665                 670

Leu Asn Leu Gly Arg Arg Glu Glu Tyr Asp Val Leu Asp Lys Arg Arg
        675                 680                 685

Gly Arg Asp Pro Glu Met Gly Gly Lys Pro Arg Arg Lys Asn Pro Gln
690                 695                 700

Glu Gly Leu Tyr Asn Glu Leu Gln Lys Asp Lys Met Ala Glu Ala Tyr
705                 710                 715                 720

Ser Glu Ile Gly Met Lys Gly Glu Arg Arg Gly Lys Gly His Asp
                725                 730                 735

Gly Leu Tyr Gln Gly Leu Ser Thr Ala Thr Lys Asp Thr Tyr Asp Ala
            740                 745                 750

Leu His Met Gln Ala Leu Pro Pro Arg
        755                 760

<210> SEQ ID NO 5
<211> LENGTH: 1491
<212> TYPE: DNA
<213> ORGANISM: Artificial
<220> FEATURE:
<223> OTHER INFORMATION: nucleotide sequence of CD19 LTG1494 (CAR 19A)

<400> SEQUENCE: 5
atggtcatgc ttctcctggt cacctccctg ctcctctgcg aactgcctca ccctgccttc      60
cttctgattc ctgacactga cattcagatg actcagacca cctcttcctt gtccgcgtca     120
ctgggagaca gagtgaccat ctcgtgtcgc gcaagccagg atatctccaa gtacctgaac     180
tggtaccaac agaagcccga cgggactgtg aagctgctga tctaccacac ctcacgcctg     240
cacagcggag tgccaagcag attctccggc tccggctcgg aaccgattac tcgcttacc      300 attagcaacc tcgagcagga ggacatcgct acctacttct gccagcaagg aaatacctg      360 ccctacacct cggcggagg aaccaaattg gaaatcaccg ctccacgag cggctccggg     420 aagcctggtt ccggggaagg ctccactaag ggtgaagtga agctccagga gtccggcccc     480
ggcctggtgg cgccgtcgca atcactctct gtgacctgta ccgtgtcggg agtgtccctg     540
cctgattacg gcgtgagctg gattcggcag ccgccgcgga agggcctgga atggctgggt     600
gtcatctggg gatccgagac tacctactac aactcggccc tgaagtcccg cctgactatc     660

```
atcaaagaca actcgaagtc ccaggtcttt ctgaagatga actccctgca aactgacgac    720
accgccatct attactgtgc taagcactac tactacggtg gaagctatgc tatggactac    780
tggggccagg ggacatccgt gacagtcagc tccgcggccg caactaccac ccctgcccct    840
cggccgccga ctccggcccc aaccatcgca agccaacccc tctccttgcg ccccgaagct    900
tgccgcccgg ccgcgggtgg agccgtgcat acccgggggc tggactttgc ctgcgatatc    960
tacatttggg ccccgctggc cggcacttgc ggcgtgctcc tgctgtcgct ggtcatcacc   1020
ctttactgca agagggccgg aagaagctg ctttacatct tcaagcagcc gttcatgcgg    1080
cccgtgcaga cgactcagga agaggacgga tgctcgtgca gattccctga ggaggaagag   1140
gggggatgcg aactgcgcgt caagttctca cggtccgccg acgcccccgc atatcaacag   1200
ggccagaatc agctctacaa cgagctgaac ctgggaagga gagaggagta cgacgtgctg   1260
gacaagcgac gcggacgcga cccggagatg ggggggaaac cacggcggaa aaaccctcag   1320
gaaggactgt acaacgaact ccagaaagac aagatggcgg aagcctactc agaaatcggg   1380 atgaaggag agcggaggag gggaaagggt cacgacgggc tgtaccaggg actgagcacc    1440
gccactaagg ataccctacga tgccttgcat atgcaagcac tcccaccccg g           1491

<210> SEQ ID NO 6
<211> LENGTH: 496
<212> TYPE: PRT
<213> ORGANISM: Artificial
<220> FEATURE:
<223> OTHER INFORMATION: amino acid sequence of CD19 LTG1494 (CAR 19A)

<400> SEQUENCE: 6

Met Val Met Leu Leu Val Thr Ser Leu Leu Cys Glu Leu Pro
1               5                   10                  15

His Pro Ala Phe Leu Leu Ile Pro Asp Thr Asp Ile Gln Met Thr Gln
            20                  25                  30

Thr Thr Ser Ser Leu Ser Ala Ser Leu Gly Asp Arg Val Thr Ile Ser
        35                  40                  45

Cys Arg Ala Ser Gln Asp Ile Ser Lys Tyr Leu Asn Trp Tyr Gln Gln
    50                  55                  60

Lys Pro Asp Gly Thr Val Lys Leu Leu Ile Tyr His Thr Ser Arg Leu
65                  70                  75                  80

His Ser Gly Val Pro Ser Arg Phe Ser Gly Ser Gly Ser Gly Thr Asp
                85                  90                  95

Tyr Ser Leu Thr Ile Ser Asn Leu Glu Gln Glu Asp Ile Ala Thr Tyr
            100                 105                 110

Phe Cys Gln Gln Gly Asn Thr Leu Pro Tyr Thr Phe Gly Gly Gly Thr
        115                 120                 125

Lys Leu Glu Ile Thr Gly Ser Thr Ser Gly Ser Gly Lys Pro Gly Ser
    130                 135                 140

Gly Glu Gly Ser Thr Lys Gly Glu Val Lys Leu Gln Glu Ser Gly Pro
145                 150                 155                 160

Gly Leu Val Ala Pro Ser Gln Ser Leu Ser Val Thr Cys Thr Val Ser
                165                 170                 175

Gly Val Ser Leu Pro Asp Tyr Gly Val Ser Trp Ile Arg Gln Pro Pro
            180                 185                 190

Arg Lys Gly Leu Glu Trp Leu Gly Val Ile Trp Gly Ser Glu Thr Thr
        195                 200                 205

Tyr Tyr Asn Ser Ala Leu Lys Ser Arg Leu Thr Ile Ile Lys Asp Asn
    210                 215                 220
```

Ser Lys Ser Gln Val Phe Leu Lys Met Asn Ser Leu Gln Thr Asp Asp
225                 230                 235                 240

Thr Ala Ile Tyr Tyr Cys Ala Lys His Tyr Tyr Gly Gly Ser Tyr
        245                 250                 255

Ala Met Asp Tyr Trp Gly Gln Gly Thr Ser Val Thr Val Ser Ser Ala
            260                 265                 270

Ala Ala Thr Thr Thr Pro Ala Pro Arg Pro Pro Thr Pro Ala Pro Thr
        275                 280                 285

Ile Ala Ser Gln Pro Leu Ser Leu Arg Pro Glu Ala Cys Arg Pro Ala
    290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
                325                 330                 335

Leu Val Ile Thr Leu Tyr Cys Lys Arg Gly Arg Lys Lys Leu Leu Tyr
            340                 345                 350

Ile Phe Lys Gln Pro Phe Met Arg Pro Val Gln Thr Thr Gln Glu Glu
        355                 360                 365

Asp Gly Cys Ser Cys Arg Phe Pro Glu Glu Glu Glu Gly Gly Cys Glu
    370                 375                 380

Leu Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
    450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495

<210> SEQ ID NO 7
<211> LENGTH: 1470
<212> TYPE: DNA
<213> ORGANISM: Artificial
<220> FEATURE:
<223> OTHER INFORMATION: nucleotide sequence of CD19 LTG1538 (CAR 19B)

<400> SEQUENCE: 7
atgcttctcc tggtcaccctc cctgctcctc tgcgaactgc ctcaccctgc cttccttctg       60
attcctgaca ttcagatgac tcagaccacc tcttccttgt ccgcgtcact gggagacaga      120
gtgaccatct cgtgtcgcgc aagccaggat atctccaagt acctgaactg gtaccaacag      180
aagcccgacg ggactgtgaa gctgctgatc taccacacct cacgcctgca cagcggagtg      240
ccaagcagat tctccggctc cggctcggga accgattact cgcttaccat tagcaacctc      300
gagcaggagg acatcgctac ctacttctgc cagcaaggaa ataccctgcc ctacaccttc      360
ggcggaggaa ccaaattgga aatcaccggc ggaggaggct ccggggggag aggttccggg      420
ggcgggggtt ccgaagtgaa gctccaggag tccggccccg gctggtggc gccgtcgcaa       480 tcactctctg tgacctgtac cgtgtcggga gtgtccctgc ctgattacgg cgtgagctgg      540

```
attcggcagc cgccgcggaa gggcctggaa tggctgggtg tcatctgggg atccgagact    600
acctactaca actcggccct gaagtcccgc ctgactatca tcaaagacaa ctcgaagtcc    660
caggtctttc tgaagatgaa ctccctgcaa actgacgaca ccgccatcta ttactgtgct    720
aagcactact actacggtgg aagctatgct atggactact gggggcaagg cacttcggtg    780
actgtgtcaa gcgcggccgc aactaccacc cctgcccctc ggccgccgac tccggcccca    840
accatcgcaa gccaacccct ctccttgcgc cccgaagctt gccgcccggc cgcgggtgga    900
gccgtgcata cccgggggct ggactttgcc tgcgatatct acatttgggc cccgctggcc    960
ggcacttgcg gcgtgctcct gctgtcgctg gtcatcaccc tttactgcaa gaggggccgg   1020
aagaagctgc tttacatctt caagcagccg ttcatgcggc ccgtgcagac gactcaggaa   1080
gaggacggat gctcgtgcag attccctgag gaggaagagg ggggatgcga actgcgcgtc   1140
aagttctcac ggtccgccga cgcccccgca tatcaacagg gccagaatca gctctacaac   1200
gagctgaacc tgggaaggag agaggagtac gacgtgctgg acaagcgacg cggacgcgac   1260
ccggagatgg gggggaaacc acggcggaaa aaccctcagg aaggactgta caacgaactc   1320
cagaaagaca agatggcgga agcctactca gaaatcggga tgaagggaga gcggaggagg   1380
ggaaagggtc acgacgggct gtaccaggga ctgagcaccg ccactaagga tacctacgat   1440
gccttgcata tgcaagcact cccaccccgg                                    1470
```

<210> SEQ ID NO 8
<211> LENGTH: 489
<212> TYPE: PRT
<213> ORGANISM: Artificial
<220> FEATURE:
<223> OTHER INFORMATION: amino acid sequence of CD19 LTG1538 (CAR 19B)

<400> SEQUENCE: 8

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
                20                  25                  30

Leu Ser Ala Ser Leu Gly Asp Arg Val Thr Ile Ser Cys Arg Ala Ser
            35                  40                  45

Gln Asp Ile Ser Lys Tyr Leu Asn Trp Tyr Gln Gln Lys Pro Asp Gly
        50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
                100                 105                 110

Gly Asn Thr Leu Pro Tyr Thr Phe Gly Gly Gly Thr Lys Leu Glu Ile
            115                 120                 125

Thr Gly Gly Gly Gly Ser Gly Gly Gly Gly Ser Gly Gly Gly Gly Ser
        130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190
```

Gly Val Ile Trp Gly Ser Glu Thr Thr Tyr Tyr Asn Ser Ala Leu Lys
            195                 200                 205

Ser Arg Leu Thr Ile Ile Lys Asp Asn Ser Lys Ser Gln Val Phe Leu
    210                 215                 220

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
                245                 250                 255

Gly Thr Ser Val Thr Val Ser Ser Ala Ala Thr Thr Thr Pro Ala
            260                 265                 270

Pro Arg Pro Pro Thr Pro Ala Pro Thr Ile Ala Ser Gln Pro Leu Ser
    275                 280                 285

Leu Arg Pro Glu Ala Cys Arg Pro Ala Ala Gly Gly Ala Val His Thr
290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
    355                 360                 365

Pro Glu Glu Glu Glu Gly Gly Cys Glu Leu Arg Val Lys Phe Ser Arg
370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
    435                 440                 445

Tyr Ser Glu Ile Gly Met Lys Gly Glu Arg Arg Arg Gly Lys Gly His
450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro
                485

<210> SEQ ID NO 9
<211> LENGTH: 1473
<212> TYPE: DNA
<213> ORGANISM: Artificial
<220> FEATURE:
<223> OTHER INFORMATION: nucleotide sequence of CD20A LTG1495 (CAR 20A)

<400> SEQUENCE: 9
atgctccttc tcgtgacctc cctgcttctc tgcgaactgc ccatcctgc cttcctgctg      60 attcccgagg tgcagttgca acagtcagga gctgaactgg tcaagccagg agccagcgtg     120
aagatgagct gcaaggcctc cggttacacc ttcacctcct acaacatgca ctgggtgaaa     180
cagaccccgg gacaagggct cgaatggatt ggcgccatct accccgggaa tggcgatact     240
tcgtacaacc agaagttcaa gggaaaggcc accctgaccg ccgacaagag ctcctccacc     300
gcgtatatgc agttgagctc cctgacctcc gaggactccg ccgactacta ctgcgcacgg     360

-continued

```
tccaactact atggaagctc gtactggttc ttcgatgtct ggggggccgg caccactgtg      420
accgtcagct ccgggggcgg aggatccggt ggaggcggaa gcggggggtgg aggatccgac     480 attgtgctga ctcagtcccc ggcaatcctg tcggcctcac cgggcgaaaa ggtcacgatg     540
acttgtagag cgtcgtccag cgtgaactac atggattggt accaaaagaa gcctggatcg     600
tcacccaagc cttggatcta cgctacatct aacctggcct ccggcgtgcc agcgcggttc     660
agcgggtccg gctcgggcac ctcatactcg ctgaccatct cccgcgtgga ggctgaggac     720
gccgcgacct actactgcca gcagtggtcc ttcaacccgc cgacttttgg aggcggtact     780
aagctggaga tcaaagcggc cgcaactacc accctgccc ctcggccgcc gactccggcc     840
ccaaccatcg caagccaacc cctctccttg cgccccgaag cttgccgccc ggccgcgggt     900
ggagccgtgc ataccgggg gctggacttt gcctgcgata tctacatttg gcccccgctg     960
gccggcactt gcggcgtgct cctgctgtcg ctggtcatca cccctttactg caagagggc     1020 cggaagaagc tgctttacat cttcaagcag ccgttcatgc ggcccgtgca gacgactcag     1080
gaagaggacg gatgctcgtg cagattccct gaggaggaag aggggggatg cgaactgcgc     1140
gtcaagttct cacggtccgc cgacgccccc gcatatcaac agggccagaa tcagctctac     1200
aacgagctga acctgggaag gagagaggag tacgacgtgc tggacaagcg acgcggacgc     1260
gacccggaga tggggggaa accacggcgg aaaaaccctc aggaaggact gtacaacgaa     1320
ctccagaaag acaagatggc ggaagcctac tcagaaatcg gatgaaggg agagcggagg     1380 aggggaaagg gtcacgacgg gctgtaccag ggactgagca ccgccactaa ggatacctac     1440
gatgccttgc atatgcaagc actcccaccc cgg                                  1473
```

<210> SEQ ID NO 10
<211> LENGTH: 491
<212> TYPE: PRT
<213> ORGANISM: Artificial
<220> FEATURE:
<223> OTHER INFORMATION: amino acid sequence of CD20A 1495 (CAR 20A)

<400> SEQUENCE: 10

```
Met Leu Leu Leu Val Thr Ser Leu Leu Cys Glu Leu Pro His Pro
1               5                   10                  15

Ala Phe Leu Leu Ile Pro Glu Val Gln Leu Gln Gln Ser Gly Ala Glu
            20                  25                  30

Leu Val Lys Pro Gly Ala Ser Val Lys Met Ser Cys Lys Ala Ser Gly
        35                  40                  45

Tyr Thr Phe Thr Ser Tyr Asn Met His Trp Val Lys Gln Thr Pro Gly
    50                  55                  60

Gln Gly Leu Glu Trp Ile Gly Ala Ile Tyr Pro Gly Asn Gly Asp Thr
65                  70                  75                  80

Ser Tyr Asn Gln Lys Phe Lys Gly Lys Ala Thr Leu Thr Ala Asp Lys
                85                  90                  95

Ser Ser Ser Thr Ala Tyr Met Gln Leu Ser Ser Leu Thr Ser Glu Asp
            100                 105                 110

Ser Ala Asp Tyr Tyr Cys Ala Arg Ser Asn Tyr Tyr Gly Ser Ser Tyr
        115                 120                 125

Trp Phe Phe Asp Val Trp Gly Ala Gly Thr Thr Val Thr Val Ser Ser
    130                 135                 140

Gly Gly Gly Gly Ser Gly Gly Gly Gly Ser Gly Gly Gly Gly Ser Asp
145                 150                 155                 160
```

```
Ile Val Leu Thr Gln Ser Pro Ala Ile Leu Ser Ala Ser Pro Gly Glu
                165                 170                 175

Lys Val Thr Met Thr Cys Arg Ala Ser Ser Val Asn Tyr Met Asp
        180                 185                 190

Trp Tyr Gln Lys Lys Pro Gly Ser Ser Pro Lys Pro Trp Ile Tyr Ala
        195                 200                 205

Thr Ser Asn Leu Ala Ser Gly Val Pro Ala Arg Phe Ser Gly Ser Gly
        210                 215                 220

Ser Gly Thr Ser Tyr Ser Leu Thr Ile Ser Arg Val Glu Ala Glu Asp
225                 230                 235                 240

Ala Ala Thr Tyr Tyr Cys Gln Gln Trp Ser Phe Asn Pro Pro Thr Phe
                245                 250                 255

Gly Gly Gly Thr Lys Leu Glu Ile Lys Ala Ala Ala Thr Thr Thr Pro
                260                 265                 270

Ala Pro Arg Pro Pro Thr Pro Ala Pro Thr Ile Ala Ser Gln Pro Leu
            275                 280                 285

Ser Leu Arg Pro Glu Ala Cys Arg Pro Ala Ala Gly Gly Ala Val His
        290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
                340                 345                 350

Met Arg Pro Val Gln Thr Thr Gln Glu Glu Asp Gly Cys Ser Cys Arg
                355                 360                 365

Phe Pro Glu Glu Glu Glu Gly Gly Cys Glu Leu Arg Val Lys Phe Ser
            370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
                420                 425                 430

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Arg Gly Lys Gly
        450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```

<210> SEQ ID NO 11
<211> LENGTH: 66
<212> TYPE: DNA
<213> ORGANISM: Artificial
<220> FEATURE:
<223> OTHER INFORMATION: nucleotide sequence of leader/signal peptide
      sequence (LP)

<400> SEQUENCE: 11
atgctgctgc tggtgaccag cctgctgctg tgcgaactgc cgcatccggc gtttctgctg    60
attccg    66

<210> SEQ ID NO 12
<211> LENGTH: 22
<212> TYPE: PRT
<213> ORGANISM: Artificial
<220> FEATURE:
<223> OTHER INFORMATION: nucleotide sequence of leader/signal peptide
      sequence (LP)

<400> SEQUENCE: 12

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 13
<211> LENGTH: 15
<212> TYPE: PRT
<213> ORGANISM: Artificial
<220> FEATURE:
<223> OTHER INFORMATION: (GGGGS)3 linker

<400> SEQUENCE: 13

Gly Gly Gly Gly Ser Gly Gly Gly Gly Ser Gly Gly Gly Gly Ser
1               5                   10                  15

<210> SEQ ID NO 14
<211> LENGTH: 25
<212> TYPE: PRT
<213> ORGANISM: Artificial
<220> FEATURE:
<223> OTHER INFORMATION: (GGGGS)5 linker

<400> SEQUENCE: 14

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 15
<211> LENGTH: 5
<212> TYPE: PRT
<213> ORGANISM: Artificial
<220> FEATURE:
<223> OTHER INFORMATION: GGGGS linker

<400> SEQUENCE: 15

Gly Gly Gly Gly Ser
1               5

<210> SEQ ID NO 16
<211> LENGTH: 66
<212> TYPE: DNA
<213> ORGANISM: Homo sapiens

<400> SEQUENCE: 16
atttgggccc cgctggccgg cacttgcggc gtgctcctgc tgtcgctggt catcacccttt      60 tactgc                                                                  66

<210> SEQ ID NO 17
<211> LENGTH: 22
<212> TYPE: PRT
<213> ORGANISM: Homo sapiens

<400> SEQUENCE: 17

Ile Trp Ala Pro Leu Ala Gly Thr Cys Gly Val Leu Leu Ser Leu
1               5                   10                  15

Val Ile Thr Leu Tyr Cys
            20

<210> SEQ ID NO 18
<211> LENGTH: 141
<212> TYPE: DNA
<213> ORGANISM: Homo sapiens

<400> SEQUENCE: 18
actaccaccc ctgcccctcg gccgccgact ccggccccaa ccatcgcaag ccaacccctc    60
tccttgcgcc ccgaagcttg ccgcccggcc gcgggtggag ccgtgcatac ccgggggctg    120
gactttgcct gcgatatcta c                                               141

<210> SEQ ID NO 19
<211> LENGTH: 47
<212> TYPE: PRT
<213> ORGANISM: Homo sapiens

<400> SEQUENCE: 19

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45

<210> SEQ ID NO 20
<211> LENGTH: 69
<212> TYPE: PRT
<213> ORGANISM: Homo sapiens

<400> SEQUENCE: 20

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 21
<211> LENGTH: 126
<212> TYPE: DNA
<213> ORGANISM: Homo sapiens

<400> SEQUENCE: 21
aagaggggcc ggaagaagct gctttacatc ttcaagcagc cgttcatgcg gcccgtgcag    60
acgactcagg aagaggacgg atgctcgtgc agattccctg aggaggaaga gggggatgc    120 gaactg                                                               126

<210> SEQ ID NO 22
<211> LENGTH: 42
<212> TYPE: PRT
<213> ORGANISM: Homo sapiens

<400> SEQUENCE: 22

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 23
<211> LENGTH: 336
<212> TYPE: DNA
<213> ORGANISM: Homo sapiens

<400> SEQUENCE: 23
cgcgtcaagt tctcacggtc cgccgacgcc cccgcatatc aacagggcca gaatcagctc      60
tacaacgagc tgaacctggg aaggagagag gagtacgacg tgctggacaa gcgacgcgga     120
cgcgaccccg agatggggg gaaaccacgc cggaaaaacc ctcaggaagg actgtacaac      180
gaactccaga agacaagat ggcggaagcc tactcagaaa tcgggatgaa gggagagcgg      240
aggaggggaa agggtcacga cgggctgtac cagggactga gcaccgccac taaggatacc      300
tacgatgcct tgcatatgca agcactccca ccccgg                                336

<210> SEQ ID NO 24
<211> LENGTH: 112
<212> TYPE: PRT
<213> ORGANISM: Homo sapiens

<400> SEQUENCE: 24

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 25
<211> LENGTH: 726
<212> TYPE: DNA
<213> ORGANISM: Artificial
<220> FEATURE:
<223> OTHER INFORMATION: nucleotide sequence of ScFv CD19 (FMC63)

<400> SEQUENCE: 25
gacattcaga tgactcagac cacctcttcc ttgtccgcgt cactgggaga cagagtgacc      60
atctcgtgtc gcgcaagcca ggatatctcc aagtacctga actggtacca acagaagccc     120

```
gacgggactg tgaagctgct gatctaccac acctcacgcc tgcacagcgg agtgccaagc    180
agattctccg gctccggctc gggaaccgat tactcgctta ccattagcaa cctcgagcag    240
gaggacatcg ctacctactt ctgccagcaa ggaaataccc tgccctacac cttcggcgga    300
ggaaccaaat tggaaatcac cggcggagga ggctccgggg aggaggttc cggggggcggg    360 ggttccgaag tgaagctcca ggagtccggc cccggcctgg tggcgccgtc gcaatcactc    420
tctgtgacct gtaccgtgtc gggagtgtcc ctgcctgatt acggcgtgag ctggattcgg    480
cagccgccgc ggaagggcct ggaatggctg ggtgtcatct ggggatccga gactacctac    540
tacaactcgg ccctgaagtc ccgcctgact atcatcaaag acaactcgaa gtcccaggtc    600
tttctgaaga tgaactccct gcaaactgac gacaccgcca tctattactg tgctaagcac    660
tactactacg gtggaagcta tgctatggac tactgggggc aaggcacttc ggtgactgtg    720
tcaagc                                                              726
```

<210> SEQ ID NO 26
<211> LENGTH: 242
<212> TYPE: PRT
<213> ORGANISM: Artificial
<220> FEATURE:
<223> OTHER INFORMATION: amino acid sequence of ScFv CD19 (FMC63)

<400> SEQUENCE: 26

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser
```

<210> SEQ ID NO 27
<211> LENGTH: 1491
<212> TYPE: DNA
<213> ORGANISM: Artificial
<220> FEATURE:
<223> OTHER INFORMATION: nucleotide sequence of anti-CD33 CAR (LTG1936)

<400> SEQUENCE: 27

```
atgctgctgc tggtgaccag cctgctgctg tgcgaactgc cgcatccggc gtttctgctg      60
attccgcagg tgcagctggt gcaatctggg gcagaggtga aaaagcccgg ggagtctctg     120
aggatctcct gtaagggttc tggattcagt tttcccacct actggatcgg ctgggtgcgc     180
cagatgcccg gaaaggcct ggagtggatg gggatcatct atcctggtga ctctgatacc      240
agatacagcc cgtccttcca aggccaggtc accatctcag ccgacaagtc catcagcacc     300
gcctacctgc agtggagcag cctgaaggcc tcggacaccg ccatgtatta ctgtgcgaga     360
ctagttggag atggctacaa tacgggggct tttgatatct ggggccaagg gacaatggtc     420
accgtctctt caggaggtgg cgggtctggt ggtggcggta cggtggtgg cggatccgat      480
attgtgatga cccacactcc actctctctg tccgtcaccc ctggacagcc ggcctccatc     540
tcctgcaagt ctagtcagag cctcctgcat agtaatggaa agacctattt gtattggtac     600
ctgcagaagc caggccagcc tccacagctc ctgatctatg agcttccaa ccggttctct      660
ggagtgccag acaggttcag tggcagcggg tcagggacag atttcacact gaaaatcagc     720
cgggtggagg ctgaggatgt tgggggttat tactgcatgc aaagtataca gcttcctatc     780
accttcggcc aagggacacg actggagatt aaagcggccg caactaccac ccctgcccct     840
cggccgccga ctccggcccc aaccatcgca agccaacccc tctccttgcg ccccgaagct     900
tgccgcccgg ccgcgggtgg agccgtgcat acccgggggc tggactttgc ctgcgatatc     960
tacatttggg ccccgctggc cggcacttgc ggcgtgctcc tgctgtcgct ggtcatcacc    1020
ctttactgca gaggggccg aagaagctg ctttacatct tcaagcagcc gttcatgcgg      1080
cccgtgcaga cgactcagga agaggacgga tgctcgtgca gattccctga ggaggaagag    1140
gggggatgcg aactgcgcgt caagttctca cggtccgccg acgcccccgc atatcaacag    1200
ggccagaatc agctctacaa cgagctgaac ctgggaagga gaggagta cgacgtgctg      1260
gacaagcgac gcggacgcga cccggagatg gggggaaac acggcggaa aaaccctcag      1320
gaaggactgt acaacgaact ccagaaagac aagatggcgg aagcctactc agaaatcggg    1380
atgaagggag agcggaggag gggaaagggt cacgacgggc tgtaccaggg actgagcacc    1440
gccactaagg atacctacga tgccttgcat atgcaagcac tcccaccccg g             1491
```

<210> SEQ ID NO 28
<211> LENGTH: 496
<212> TYPE: PRT
<213> ORGANISM: Artificial
<220> FEATURE:
<223> OTHER INFORMATION: amino acid sequence of anti-CD33 CAR (LTG1936)

<400> SEQUENCE: 28

Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Ala Glu
            20                  25                  30

Val Lys Lys Pro Gly Glu Ser Leu Arg Ile Ser Cys Lys Gly Ser Gly
        35                  40                  45

```
Phe Ser Phe Pro Thr Tyr Trp Ile Gly Trp Val Arg Gln Met Pro Gly
 50                  55                  60

Lys Gly Leu Glu Trp Met Gly Ile Ile Tyr Pro Gly Asp Ser Asp Thr
 65                  70                  75                  80

Arg Tyr Ser Pro Ser Phe Gln Gly Gln Val Thr Ile Ser Ala Asp Lys
                 85                  90                  95

Ser Ile Ser Thr Ala Tyr Leu Gln Trp Ser Ser Leu Lys Ala Ser Asp
            100                 105                 110

Thr Ala Met Tyr Tyr Cys Ala Arg Leu Val Gly Asp Gly Tyr Asn Thr
        115                 120                 125

Gly Ala Phe Asp Ile Trp Gly Gln Gly Thr Met Val Thr Val Ser Ser
130                 135                 140

Gly Gly Gly Gly Ser Gly Gly Gly Ser Gly Gly Gly Gly Ser Asp
145                 150                 155                 160

Ile Val Met Thr His Thr Pro Leu Ser Leu Ser Val Thr Pro Gly Gln
                165                 170                 175

Pro Ala Ser Ile Ser Cys Lys Ser Gln Ser Leu Leu His Ser Asn
                180                 185                 190

Gly Lys Thr Tyr Leu Tyr Trp Tyr Leu Gln Lys Pro Gly Gln Pro Pro
        195                 200                 205

Gln Leu Leu Ile Tyr Gly Ala Ser Asn Arg Phe Ser Gly Val Pro Asp
210                 215                 220

Arg Phe Ser Gly Ser Gly Ser Gly Thr Asp Phe Thr Leu Lys Ile Ser
225                 230                 235                 240

Arg Val Glu Ala Glu Asp Val Gly Val Tyr Tyr Cys Met Gln Ser Ile
                245                 250                 255

Gln Leu Pro Ile Thr Phe Gly Gln Gly Thr Arg Leu Glu Ile Lys Ala
                260                 265                 270

Ala Ala Thr Thr Thr Pro Ala Pro Arg Pro Pro Thr Pro Ala Pro Thr
            275                 280                 285

Ile Ala Ser Gln Pro Leu Ser Leu Arg Pro Glu Ala Cys Arg Pro Ala
        290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
                325                 330                 335

Leu Val Ile Thr Leu Tyr Cys Lys Arg Gly Arg Lys Lys Leu Leu Tyr
                340                 345                 350

Ile Phe Lys Gln Pro Phe Met Arg Pro Val Gln Thr Thr Gln Glu Glu
            355                 360                 365

Asp Gly Cys Ser Cys Arg Phe Pro Glu Glu Glu Glu Gly Gly Cys Glu
        370                 375                 380

Leu Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
                420                 425                 430

Lys Pro Arg Arg Lys Asn Pro Gln Glu Gly Leu Tyr Asn Glu Leu Gln
            435                 440                 445

Lys Asp Lys Met Ala Glu Ala Tyr Ser Glu Ile Gly Met Lys Gly Glu
450                 455                 460
```

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
            485                 490                 495

<210> SEQ ID NO 29
<211> LENGTH: 1476
<212> TYPE: DNA
<213> ORGANISM: Artificial
<220> FEATURE:
<223> OTHER INFORMATION: nucleotide sequence of anti-mesothelin CAR
      (LTG1904)

<400> SEQUENCE: 29

| | | | | | | |
|---|---|---|---|---|---|---|
| atgctgctgc | tggtgaccag | cctgctgctg | tgcgaactgc | cgcatccggc | gtttctgctg | 60 |
| attccggagg | tccagctggt | acagtctggg | ggaggcttgg | tacagcctgg | ggggtccctg | 120 |
| agactctcct | gtgcagcctc | tggattcacc | tttgatgatt | atgccatgca | ctgggtccgg | 180 |
| caagctccag | ggaagggcct | ggagtgggtc | tcaggtatta | gttggaatag | tggtagcata | 240 |
| ggctatgcgg | actctgtgaa | gggccgattc | accatctcca | gagacaacgc | caagaactcc | 300 |
| ctgtatctgc | aaatgaacag | tctgagagct | gaggacacgg | ccttgtatta | ctgtgcaaaa | 360 |
| gatttatcgt | cagtggctgg | acctttaac | tactggggcc | agggcaccct | ggtcaccgtc | 420 |
| tcctcaggag | gtggcgggtc | tggtggaggc | ggtagcggcg | gtggcggatc | ctcttctgag | 480 |
| ctgactcagg | accctgctgt | gtctgtggcc | ttgggacaga | cagtcaggat | cacatgccaa | 540 |
| ggagacagcc | tcagaagcta | ttatgcaagc | tggtaccagc | agaagccagg | acaggcccct | 600 |
| gtacttgtca | tctatggtaa | aaacaaccgg | ccctcaggga | tcccagaccg | attctctggc | 660 |
| tccagctcag | gaaacacagc | ttccttgacc | atcactgggg | ctcaggcgga | ggatgaggct | 720 |
| gactattact | gtaactcccg | ggacagcagt | ggtaaccatc | tggtattcgg | cggaggcacc | 780 |
| cagctgaccg | tcctcggtgc | ggccgcaact | accacccctg | ccctcggcc | gccgactccg | 840 |
| gccccaacca | tcgcaagcca | accctctcc | ttgcgcccg | aagcttgccg | ccggccgcg | 900 |
| ggtggagccg | tgcatacccg | ggggctggac | tttgcctgcg | atatctacat | ttgggccccg | 960 |
| ctggccggca | cttgcggcgt | gctcctgctg | tcgctggtca | tcacccttta | ctgcaagagg | 1020 |
| ggccggaaga | agctgcttta | catcttcaag | cagccgttca | tgcggcccgt | gcagacgact | 1080 |
| caggaagagg | acggatgctc | gtgcagattc | cctgaggagg | aagaggggg | atgcgaactg | 1140 |
| cgcgtcaagt | tctcacggtc | cgccgacgcc | ccgcatatc | aacagggcca | gaatcagctc | 1200 |
| tacaacgagc | tgaacctggg | aaggagagag | gagtacgacg | tgctggacaa | gcgacgcgga | 1260 |
| cgcgaccegg | agatgggggg | gaaaccacgg | cggaaaaacc | ctcaggaagg | actgtacaac | 1320 |
| gaactccaga | aagacaagat | ggcggaagcc | tactcagaaa | tcgggatgaa | gggagagcgg | 1380 |
| aggaggggaa | agggtcacga | cgggctgtac | cagggactga | gcaccgccac | taaggatacc | 1440 |
| tacgatgcct | tgcatatgca | agcactccca | ccccgg | | | 1476 |

<210> SEQ ID NO 30
<211> LENGTH: 492
<212> TYPE: PRT
<213> ORGANISM: Artificial
<220> FEATURE:
<223> OTHER INFORMATION: amino acid sequence of anti-mesothelin CAR
      (LTG1904)

<400> SEQUENCE: 30

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Gly Gly
                20                  25                  30

Leu Val Gln Pro Gly Gly Ser Leu Arg Leu Ser Cys Ala Ala Ser Gly
            35                  40                  45

Phe Thr Phe Asp Asp Tyr Ala Met His Trp Val Arg Gln Ala Pro Gly
    50                  55                  60

Lys Gly Leu Glu Trp Val Ser Gly Ile Ser Trp Asn Ser Gly Ser Ile
65                  70                  75                  80

Gly Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Leu Tyr Tyr Cys Ala Lys Asp Leu Ser Ser Val Ala Gly Pro
        115                 120                 125

Phe Asn Tyr Trp Gly Gln Gly Thr Leu Val Thr Val Ser Ser Gly Gly
    130                 135                 140

Gly Gly Ser Gly Gly Gly Gly Ser Gly Gly Gly Gly Ser Ser Ser Glu
145                 150                 155                 160

Leu Thr Gln Asp Pro Ala Val Ser Val Ala Leu Gly Gln Thr Val Arg
                165                 170                 175

Ile Thr Cys Gln Gly Asp Ser Leu Arg Ser Tyr Tyr Ala Ser Trp Tyr
            180                 185                 190

Gln Gln Lys Pro Gly Gln Ala Pro Val Leu Val Ile Tyr Gly Lys Asn
        195                 200                 205

Asn Arg Pro Ser Gly Ile Pro Asp Arg Phe Ser Gly Ser Ser Ser Gly
    210                 215                 220

Asn Thr Ala Ser Leu Thr Ile Thr Gly Ala Gln Ala Glu Asp Glu Ala
225                 230                 235                 240

Asp Tyr Tyr Cys Asn Ser Arg Asp Ser Ser Gly Asn His Leu Val Phe
                245                 250                 255

Gly Gly Gly Thr Gln Leu Thr Val Leu Gly Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415
```

-continued

```
Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
        450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490
```